United States Patent
Kato et al.

(10) Patent No.: US 11,174,274 B2
(45) Date of Patent: Nov. 16, 2021

(54) NAPHTHALOCYANINE COMPOUND, METHOD FOR PRODUCING SAME, AND USE THEREOF

(71) Applicant: YAMAMOTO CHEMICALS, INC., Yao (JP)

(72) Inventors: Kenichi Kato, Yao (JP); Akihiro Kohsaka, Yao (JP); Hiroyuki Sasaki, Yao (JP)

(73) Assignee: YAMAMOTO CHEMICALS, INC., Yao (JP)

( * ) Notice: Subject to any disclaimer, the term of this patent is extended or adjusted under 35 U.S.C. 154(b) by 32 days.

(21) Appl. No.: 16/603,088

(22) PCT Filed: Apr. 6, 2018

(86) PCT No.: PCT/JP2018/014747
§ 371 (c)(1),
(2) Date: Oct. 4, 2019

(87) PCT Pub. No.: WO2018/186490
PCT Pub. Date: Oct. 11, 2018

(65) Prior Publication Data
US 2021/0107924 A1    Apr. 15, 2021

(30) Foreign Application Priority Data
Apr. 7, 2017 (JP) .............................. JP2017-076480

(51) Int. Cl.
*C07F 1/08* (2006.01)

(52) U.S. Cl.
CPC ....................... *C07F 1/08* (2013.01)

(58) Field of Classification Search
None
See application file for complete search history.

(56) References Cited

U.S. PATENT DOCUMENTS 5,438,135 A * 8/1995 Tai ........................ C07F 5/069
540/128
5,618,929 A * 4/1997 Harrison ............ C09K 19/3488
540/139
(Continued)

FOREIGN PATENT DOCUMENTS

JP    63191690 A * 8/1988 ............. G11B 7/248
JP    1-108264 A    4/1989
(Continued)

OTHER PUBLICATIONS

Compounds Indexed by CAS in WO 2018186490 (2018) (Year: 2018).*

(Continued)

*Primary Examiner* — Alexander R Pagano
(74) *Attorney, Agent, or Firm* — Birch, Stewart, Kolasch & Birch, LLP

(57) ABSTRACT

Provided are a novel naphthalocyanine compound, which has strong absorption in a near-infrared range, extremely weak absorption in a visible range, and high resistance such as light resistance and heat resistance, and exhibits excellent solubility in an organic solvent or a resin, a heat ray shielding material, and uses of the naphthalocyanine compound such as a heat ray shielding material and the like.
The naphthalocyanine compound is represented by General Formula (1).

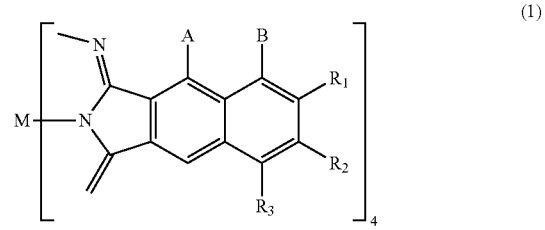

(1)

wherein, in Formula (1), M represents two hydrogen atoms, a divalent metal, or a derivative of a trivalent or tetravalent metal, $R_1$ to $R_3$ each independently represent a hydrogen atom, a halogen atom, or a linear, branched, or cyclic alkyl group, A represents Formula (2), and B represents Formula (3),

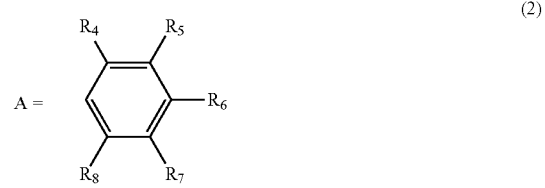
(2)

wherein, in Formula (2), $R_4$ to $R_8$ each independently represent a hydrogen atom, a halogen atom, an alkyl group, an alkoxy group, an alkylthio group, an aryloxy group, or an arylthio group, and

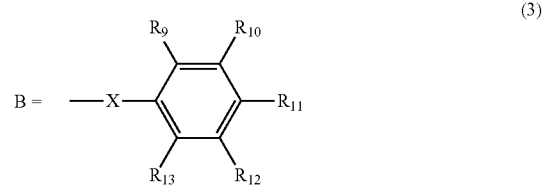
(3)

wherein, in Formula (3), X represents an oxygen atom, a sulfur atom, and or an imino group, $R_9$ to $R_{13}$ each independently represent a hydrogen atom, a halogen (Continued)

atom, an alkyl group, an alkoxy group, an ester group, an amide group, or a sulfonamide group.

13 Claims, 7 Drawing Sheets

(56) References Cited

U.S. PATENT DOCUMENTS

| | | | |
|---|---|---|---|
| 5,804,102 A | 9/1998 | Oi et al. | |
| 6,232,038 B1 | 5/2001 | Takasaki et al. | |
| 6,323,340 B1* | 11/2001 | Masuda | C09B 47/063 540/128 |
| 6,468,713 B1* | 10/2002 | Terao | C07D 487/22 252/587 |
| 6,544,720 B2 | 4/2003 | Takasaki et al. | |
| 6,780,515 B2 | 8/2004 | Döbler | |
| 7,470,315 B2 | 12/2008 | Vonwiller et al. | |
| 7,579,064 B2 | 8/2009 | Vonwiller et al. | |
| 8,346,024 B2 | 1/2013 | Vonwiller et al. | |
| 10,370,464 B2 | 8/2019 | Tone et al. | |
| 2001/0007736 A1 | 7/2001 | Takasaki et al. | |
| 2002/0182389 A1 | 12/2002 | Döbler | |
| 2003/0234995 A1* | 12/2003 | Masuda | C09B 47/10 359/885 |
| 2007/0008393 A1 | 1/2007 | Vonwiller et al. | |
| 2009/0061179 A1 | 3/2009 | Vonwiller et al. | |
| 2009/0284809 A1 | 11/2009 | Vonwiller et al. | |
| 2010/0048902 A1* | 2/2010 | Kang | C07F 15/025 546/12 |
| 2011/0311911 A1* | 12/2011 | Kimura | C09B 47/00 430/108.21 |
| 2014/0264202 A1* | 9/2014 | Nagaya | C09B 47/04 252/587 |
| 2018/0179306 A1 | 6/2018 | Tone et al. | |
| 2019/0163053 A1* | 5/2019 | Nakamura | C09B 67/0033 |
| 2020/0032066 A1* | 1/2020 | Kohsaka | C09B 47/0671 |

FOREIGN PATENT DOCUMENTS

| | | | | |
|---|---|---|---|---|
| JP | 01105788 A | * | 4/1989 | ............ G11B 7/248 |
| JP | 2-43091 A | | 2/1990 | |
| JP | 02043091 A | * | 2/1990 | ............ G11B 7/248 |
| JP | 2-134386 A | | 5/1990 | |
| JP | 02244061 A | * | 9/1990 | |
| JP | 3-79683 A | | 4/1991 | |
| JP | 7-216275 A | | 8/1995 | |
| JP | 08009714 A | * | 1/1996 | |
| JP | 10-78509 A | | 3/1998 | |
| JP | 2000-187322 A | | 7/2000 | |
| JP | 2002-264203 A | | 9/2002 | |
| JP | 2004-231832 A | | 8/2004 | |
| JP | 2004-525802 A | | 8/2004 | |
| JP | 2005-105190 A | | 4/2005 | |
| JP | 2009-500460 A | | 1/2009 | |
| JP | 2009-29955 A | | 2/2009 | |
| JP | 2009029955 A | * | 2/2009 | |
| JP | 6015670 B2 | * | 10/2016 | ............ G06T 5/50 |
| JP | 2018053135 A | * | 4/2018 | |
| WO | WO-0142368 A1 | * | 6/2001 | ............ A61P 13/08 |
| WO | WO 2014/208484 A1 | | 12/2014 | |
| WO | WO 2017/002920 A1 | | 1/2017 | |

OTHER PUBLICATIONS

CAS Abstract and Indexed Compounds T Kashima et al., JP 02043091 (1991) (Year: 1991).*
W. Lv et al., 49 Inorganic Chemistry, 6628-6635 (2010) (Year: 2010).*
https://www.ebi.ac.uk/chebi/searchld.do?chebild=CHEBI:29342 (downloaded May 19, 2021) (Year: 2021).*
International Search Report (PCT/ISA/210) issued in PCT/JP2018/014747, dated May 1, 2018.
Written Opinion (PCT/ISA/237) issued in PCT/JP2018/014747, dated May 1, 2018.

* cited by examiner

NAPHTHALOCYANINE COMPOUND, METHOD FOR PRODUCING SAME, AND USE THEREOF

TECHNICAL FIELD

The present invention relates to a novel phthalocyanine compound which exhibits excellent transparency to visible light and has high durability and uses of the phthalocyanine compound.

Specifically, the present invention relates to a novel phthalocyanine compound, which has strong absorption in a near-infrared range, is hardly colored due to extremely weak absorption the compound has in a visible range, exhibits high durability against light or heat, is soluble in an organic solvent, and can be widely used in near-infrared absorbing materials such as a near-infrared absorbing filter, a security ink, a heat ray shielding film, an interlayer for laminated glass, and an infrared thermosensitive recording material, and uses of the phthalocyanine compound, particularly, a heat ray shielding material.

BACKGROUND ART

In recent years, a near-infrared absorbing material has been widely used in the field of an optical recording medium, a near-infrared photosensitizer, a photothermal conversion agent, a near-infrared cut-off filter, a near-infrared absorbing ink, a heat ray shielding material, and the like.

Particularly, for the uses such as a near-infrared cut-off filter used in a plasma display or the like, a transparent ink used for security, a heat ray shielding material used in windows of automobiles or buildings, and laser welding of plastics, there has been an increasing demand for the development of a near-infrared absorbing material which has a high ability to absorb near-infrared, has a high visible light transmittance which is in other words that the material is hardly colored and has high transparency, exhibits high durability against light or heat, and dissolves in an organic solvent or a resin.

As such a near-infrared absorbing material, various organic colorants have been examined, and an aminium compound, an immonium compound, a phthalocyanine compound, a naphthalocyanine compound, and the like have been partially put to practical use. Particularly, since a phthalocyanine compound has high ability to absorb near-infrared and relatively excellent transparency to visible light, a phthalocyanine compound is being examined in various ways as a near-infrared absorbing material for the uses described above.

Patent Documents 1 and 2 disclose a near-infrared absorbing ink using a naphthalocyanine compound in which a substituent is coordinated to a central metal in a direction (axial position) perpendicular to the plane of a naphthalocyanine skeleton, a method of joining plastic materials, and the like. Although the documents described that the used naphthalocyanine compound absorbs the near-infrared but little visible light, this compound is defective because of low durability.

Patent Document 3 discloses a near-infrared absorbing ink composition containing a near-infrared absorber, an ultraviolet absorber, and a polyester resin, in which palladium naphthalocyanine having eight isopentyloxy groups in α-position is used as a naphthalocyanine compound-based near-infrared absorber.

Patent Document 4 discloses a method of crystallizing polyester, which has a specific polymerization catalyst and an infrared absorber, within a short period of time by means of heating by using an infrared heater, in which vanadyl naphthalocyanine having eight butoxy groups in α-position is used as the infrared absorber. These naphthalocyanine compounds having alkoxy groups in α-position have weak absorption in a visible range. Accordingly, articles containing these compounds are hardly colored and have high transparency, but are defective because of low durability. Furthermore, the transparency of these articles to visible light is insufficient.

Patent Document 5 discloses a heat absorbing layer system which is used as heat shielding thermoplastic plastic or the like as a substitute for window glass of automobiles and the like and contains naphthalocyanine or the like as an infrared absorber. As the naphthalocyanine-based infrared absorber, vanadyl-5,14,23,32-tetraphenyl-2,3-naphthalocyanine (vanadyl naphthalocyanine having four phenyl groups in α-position) is used. This naphthalocyanine compound has an excellent ability to absorb near-infrared and excellent transparency (visible light transmitting properties), but light resistance thereof is insufficient.

Patent Document 6 discloses a naphthalocyanine colorant compound having four substituted phenyl groups in α-position. Specifically, the document discloses a vanadyl naphthalocyanine compound having phenyl groups, which have a nitro group or an acetamide group as a substituent, in α-position. The document describes that the naphthalocyanine compound has excellent light stability while maintaining invisibility. However, according to the follow-up study conducted by the inventors of the present invention, unfortunately, the compound is poorly soluble in a solvent, poorly compatible with a resin, and has poor processability, and invisibility thereof is insufficient. In Patent Document 6, as substituents that the phenyl groups may have, a halogen group and the like are formally incorporated into a compound represented by a general structural formula depicted by the Markush method. However, the document does not specifically describe compounds having a combination of the substituents.

Patent Document 7 discloses a tatraazaporphyrin compound obtained by adding one or two naphthalene derivative molecules to a naphthalocyanine compound having four substituted phenyl groups in α-position. The document describes that the tatraazaporphyrin compound has characteristic absorption around 750 to 850 nm and is soluble in a solvent and stable against heat or light. However, unfortunately, because the added naphthalene derivatives are easily oxidized and deteriorate, the compound is easily discolored.

RELATED DOCUMENT

Patent Document

[Patent Document 1] Japanese Unexamined Patent Publication No. 3-079683

[Patent Document 2] Japanese Unexamined Patent Publication No. 2004-231832

[Patent Document 3] Japanese Unexamined Patent Publication No. 7-216275

[Patent Document 4] Japanese Unexamined Patent Publication No. 2005-105190

[Patent Document 5] PCT Japanese Translation Patent Publication No. 2004-525802

[Patent Document 6] Japanese Unexamined Patent Publication No. 2009-29955

[Patent Document 7] Japanese Unexamined Patent Publication No. 2-134386

SUMMARY OF THE INVENTION

Technical Problem

An object of the present invention is to provide a novel naphthalocyanine compound, which has strong absorption in an infrared range, extremely weak absorption in a visible range, and high resistance such as light resistance and heat resistance, and exhibits excellent solubility in an organic solvent or a resin, and uses of the naphthalocyanine compound such as a heat ray shielding material.

Solution to Problem

Regarding the above object, the inventors of the present invention conducted intensive examinations. As a result, the inventors have found that a naphthalocyanine compound having a specific structure satisfies the characteristics described above, and have accomplished the present invention. That is, the present invention relates to the following.

(i) A naphthalocyanine compound represented by General Formula (1),

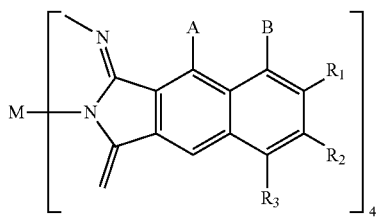

(1)

in which, Formula (1), M represents two hydrogen atoms, a divalent metal, or a derivative of a trivalent or tetravalent metal, $R_1$ to $R_3$ each independently represent a hydrogen atom, a halogen atom, or a linear, branched, or cyclic alkyl group, A represents Formula (2), and B represents Formula (3),

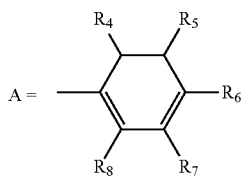

(2)

in which, Formula (2), $R_4$ to $R_8$ each independently represent a hydrogen atom, a halogen atom, a substituted or unsubstituted linear, branched, or cyclic alkyl group, a substituted or unsubstituted linear, branched, or cyclic alkoxy group, a substituted or unsubstituted linear, branched, or cyclic alkylthio group, an aryloxy group which optionally have a substituent, an arylthio group which optionally have a substituent, and $R_4$ to $R_8$ do not simultaneously represent a hydrogen atom, and

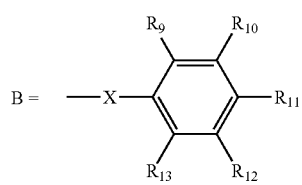

(3)

in which, Formula (3), X represents an oxygen atom, a sulfur atom, or a substituted or unsubstituted imino group, $R_9$ to $R_{13}$ each independently represent a hydrogen atom, a halogen atom, a substituted or unsubstituted alkyl group, a substituted or unsubstituted alkoxy group, an ester group ($COOX_1$ in which $X_1$ represents a hydrogen atom, a substituted or unsubstituted alkyl group, or a substituted or unsubstituted aryl group), an amide group ($CONX_2X_3$ in which $X_2$ and $X_3$ each independently represent a hydrogen atom, a substituted or unsubstituted alkyl group, or a substituted or unsubstituted aryl group), or a sulfonamide group ($SO_2NX_4X_5$ in which $X_4$ and $X_5$ each independently represent a hydrogen atom, a substituted or unsubstituted alkyl group, or a substituted or unsubstituted aryl group), and $R_9$ to $R_{13}$ do not simultaneously represent a hydrogen atom.

(ii) The naphthalocyanine compound of (i) that is at least one kind selected from compounds represented by General Formulae (1)-a to (1)-d,

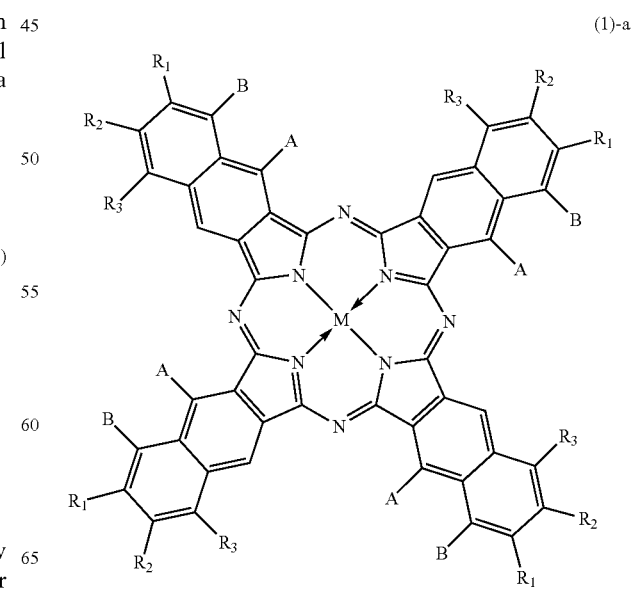

(1)-a (1)-b

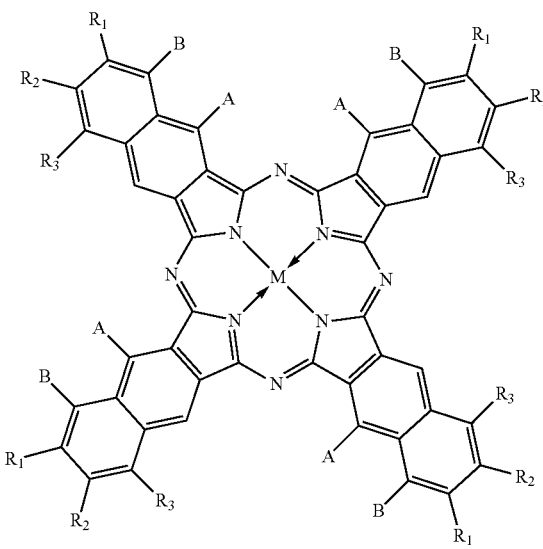

(1)-d

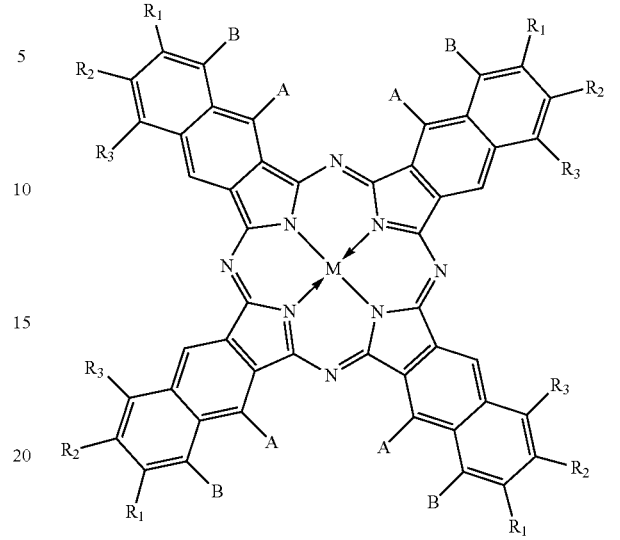

in which, Formulae (1)-a to (1)-d, M, $R_1$ to $R_3$, A, and B have the same definition as M, $R_1$ to $R_3$, A, and B in General Formula (1).

(iii) The naphthalocyanine compound described in (ii) or (iii) that is represented by General Formula (1)-a, (1)-a

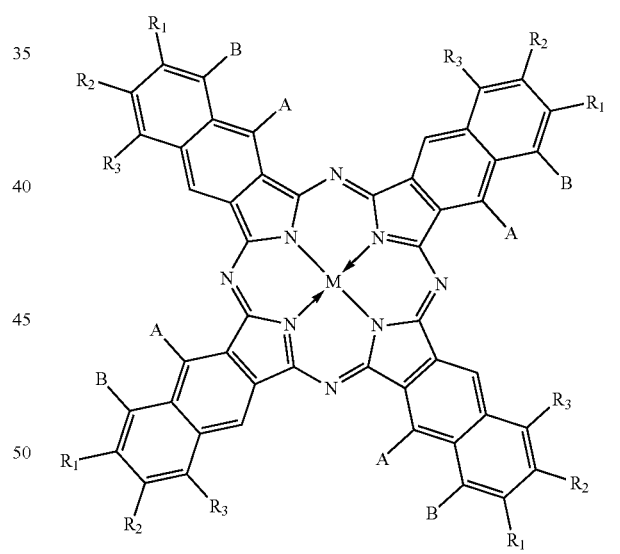

in which, Formula (1)-a, M, $R_1$ to $R_3$, A, and B have the same definition as M, $R_1$ to $R_3$, A, and B in General Formula (1).

(iv) The naphthalocyanine compound of any one of (i) to (iii), in which M represents two hydrogen atoms, Pd, Cu, Zn, Pt, Ni, TiO, Co, Fe, Mn, Sn, Al—Cl, VO, or In—Cl.

(v) The naphthalocyanine compound of anyone of (i) to (iv) that is produced by reacting at least one kind of compounds selected from a naphthalene-2,3-dicarbonitrile compound represented by General Formula (4) and a 1,3-diiminobenzisoindoline compound represented by General Formula (5) with a metal or a metal derivative, (1)-c

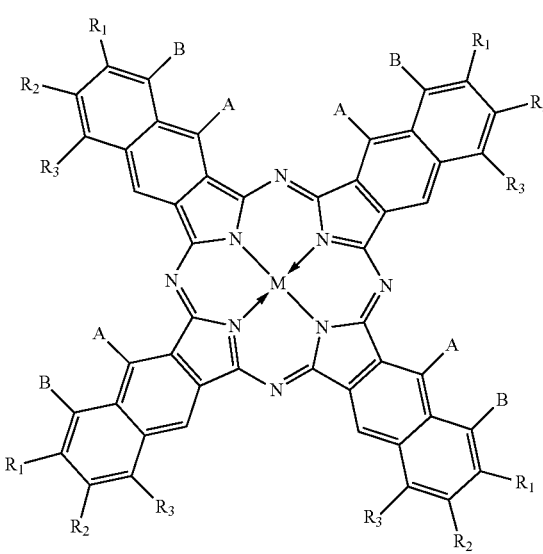

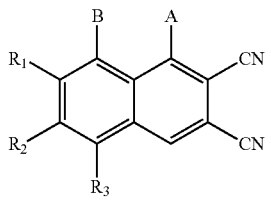

(4)

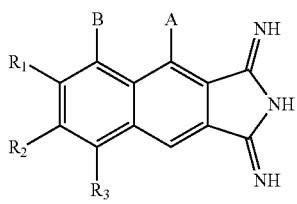

(5)

in which, Formulae (4) and (5), $R_1$ to $R_3$, A, and B have the same definition as $R_1$ to $R_3$, A, and B in General Formula (1).

(vi) A naphthalene-2,3-dicarbonitrile compound represented by General Formula (4),

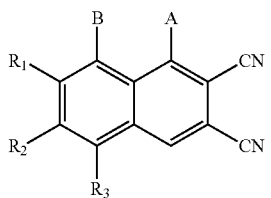

(4)

in which, Formula (4), $R_1$ to $R_3$, A, and B have the same definition as $R_1$ to $R_3$, A, and B in General Formula (1).

(vii) A 1,3-diiminobenzisoindoline compound represented by General Formula (5),

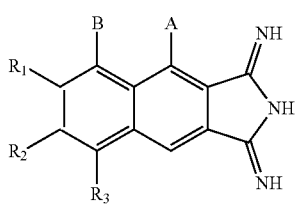

(5)

in which, Formula (5), $R_1$ to $R_3$, A, and B have the same definition as $R_1$ to $R_3$, A, and B in General Formula (1).

(viii) A near-infrared absorbing material containing the naphthalocyanine compound of any one of (i) to (iv).

(ix) A heat ray shielding material containing the naphthalocyanine compound of any one of (i) to (iv).

(x) The heat ray shielding material of (ix) that is a heat ray shielding film.

(xi) The heat ray shielding material of (ix) that is an interlayer for laminated glass.

Advantageous Effects of Invention

According to the present invention, it is possible to provide a naphthalocyanine compound, which has strong absorption in a near-infrared range and, extremely weak absorption in a visible range, and excellent durability and exhibits excellent solubility in an organic solvent or a resin, and uses of the naphthalocyanine compound such as a near-infrared absorbing material and a heat ray shielding material having the characteristics described above.

DESCRIPTION OF EMBODIMENTS

Figure 1:
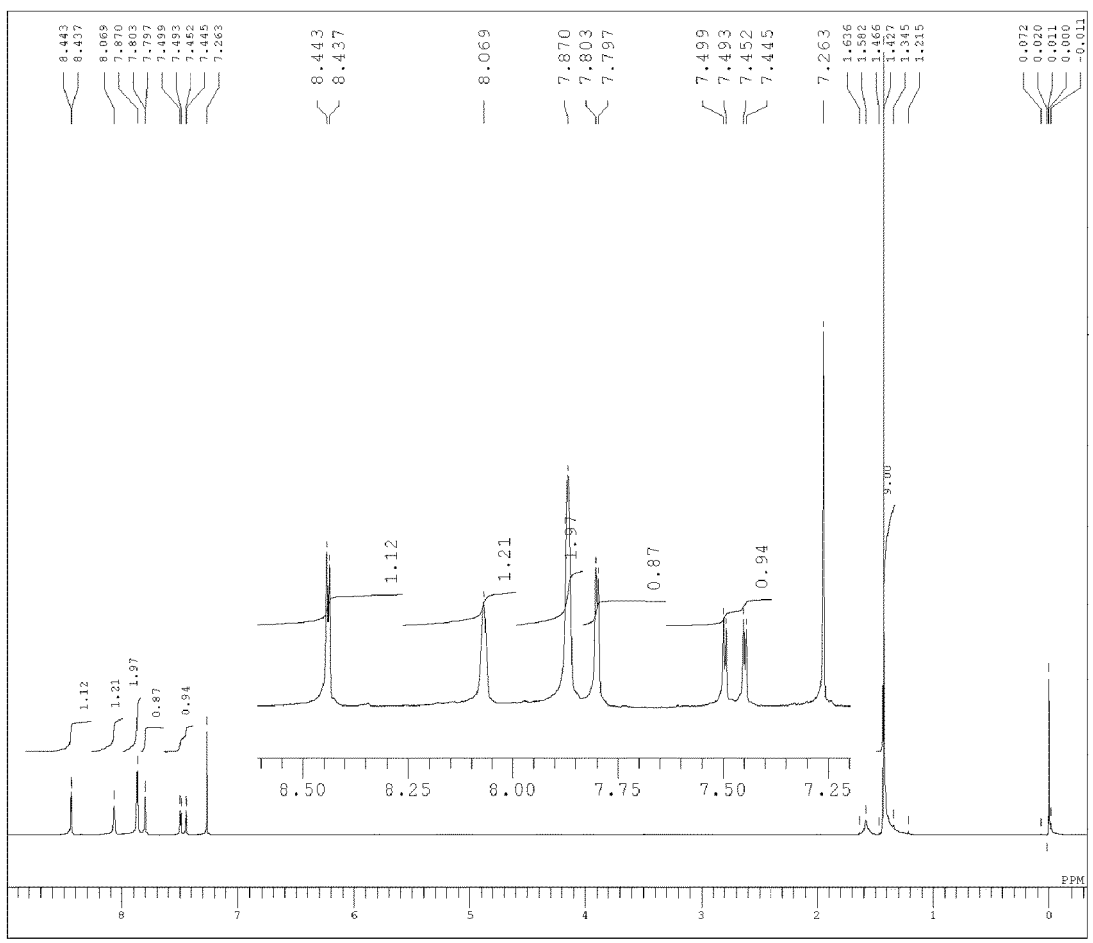
FIG. 1 is a H-NMR spectrum of a compound produced in Example 1.

Hereinafter, the present invention will be specifically described.

[Naphthalocyanine Compound]

A first invention of the present invention is a naphthalocyanine compound represented by General Formula (1).

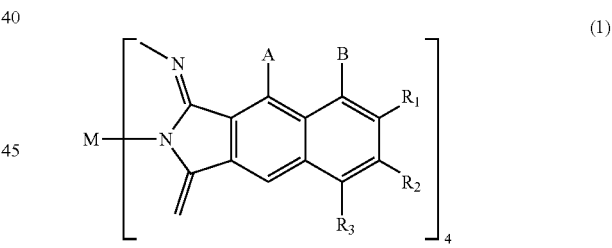

(1)

In Formula (1), M represents two hydrogen atoms, a divalent metal, or a derivative of a trivalent or tetravalent metal, $R_1$ to $R_3$ each independently represent a hydrogen atom, a halogen atom, or a linear, branched, or cyclic alkyl group, A represents Formula (2), and B represents Formula (3).

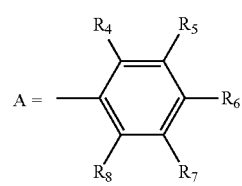

(2)

In Formula (2), $R_4$ to $R_e$ each independently represent a hydrogen atom, a halogen atom, a substituted or unsubstituted linear, branched, or cyclic alkyl group, a substituted or unsubstituted linear, branched, or cyclic alkoxy group, a substituted or unsubstituted linear, branched, or cyclic alkylthio group, an aryloxy group which optionally have a substituent, an arylthio group which optionally have a substituent, and $R_4$ to $R_8$ do not simultaneously represent a hydrogen atom.

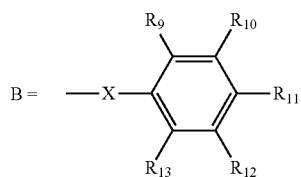

(3)

In Formula (3), X represents an oxygen atom, a sulfur atom, or a substituted or unsubstituted imino group, $R_9$ to $R_{13}$ each independently represent a hydrogen atom, a halogen atom, a substituted or unsubstituted alkyl group, a substituted or unsubstituted alkoxy group, an ester group ($COOX_1$ in which $X_1$ represents a hydrogen atom, a substituted or unsubstituted alkyl group, or a substituted or unsubstituted aryl group), an amide group ($CONX_2X_3$ in which $X_2$ and $X_3$ each independently represent a hydrogen atom, a substituted or unsubstituted alkyl group, or a substituted or unsubstituted aryl group), or a sulfonamide group ($SO_2NX_4X_5$ in which $X_4$ and $X_5$ each independently represent a hydrogen atom, a substituted or unsubstituted alkyl group, or a substituted or unsubstituted aryl group), and $R_9$ to $R_{13}$ do not simultaneously represent a hydrogen atom.

More specifically, the naphthalocyanine compound represented by General Formula (1) is at least one kind selected from compounds represented by General Formulae (1)-a to (1)-d. That is, the naphthalocyanine compound is one kind of isomer represented by any of General Formulae (1)-a to (1)-d or any mixture of these.

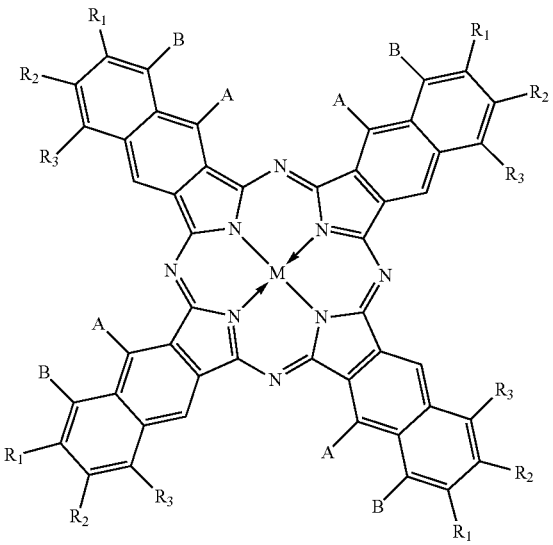

(1)-b

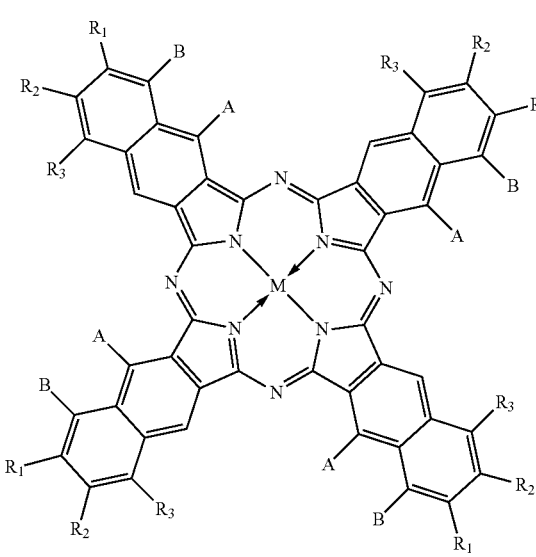

(1)-a

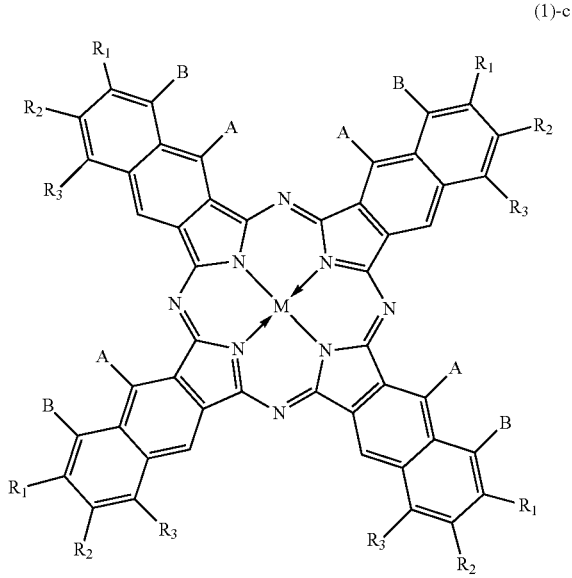

(1)-c

-continued

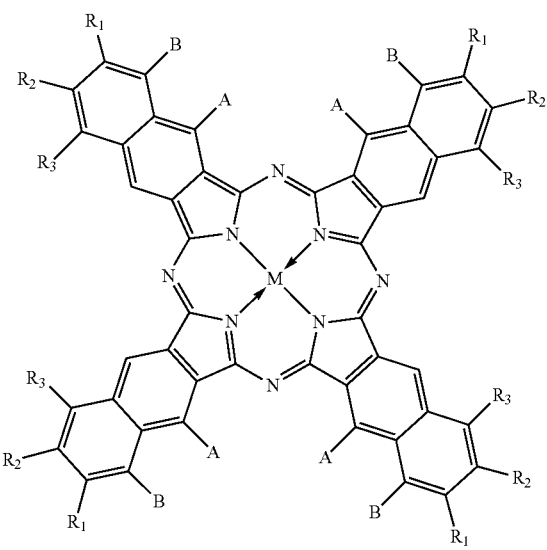

(1)-d

In General Formulae (1)-a to (1)-d, M, $R_1$ to $R_3$, A, and B have the same definition as M, $R_1$ to $R_3$, A, and in General Formula (1).

Among the isomers (1)-a to (1)-d, the isomer represented by (1)-a is preferable, because this isomer has particularly high durability such as light resistance and heat resistance.

In General Formula (1) and Formulae (1)-a to (1)-d, M represents two hydrogen atoms, Pd, Cu, Zn, Pt, Ni, TiO, Co, Fe, Mn, Sn, Al—Cl, VO, or In—Cl. M preferably represents two hydrogen atoms, Pd, Cu, Zn, or VO, and more preferably represents Cu.

In General Formula (1) and Formulae (1)-a to (1)-d, each of $R_1$ to $R_3$ more preferably represents a hydrogen atom, a halogen atom, or a substituted or unsubstituted linear, branched, or cyclic alkyl group.

Examples of the halogen atom of $R_1$ to $R_3$ include a fluorine atom, a chlorine atom, a bromine atom, and an iodine atom. Among these, a fluorine atom and a chlorine atom are preferable, and a fluorine atom is more preferable.

The substituted or unsubstituted alkyl group of $R_1$ to $R_3$ is preferably a substituted or unsubstituted alkyl group having 1 to 18 carbon atoms, and more preferably a substituted or unsubstituted alkyl group having 1 to 12 carbon atoms.

Examples of the unsubstituted alkyl group include linear, branched, or cyclic unsubstituted alkyl groups such as a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a cyclopentyl group, a n-hexyl group, a cyclohexyl group, a 1-methylpentyl group, a 4-methyl-2-pentyl group, a 2-ethylbutyl group, a n-heptyl group, a 1-methylhexyl group, a n-octyl group, a 1-methylheptyl group, and a 2-ethylhexyl group.

Examples of the substituted alkyl group include an alkyl group having an alkyloxy group or an alkenyloxy group such as a methoxymethyl group, an ethoxymethyl group, a n-butoxymethyl group, a n-hexyloxymethyl group, a (2-ethylbutyloxy) methyl group, or a 2-(4'-pentenyloxy) ethyl group, an alkyl group having an aralkyloxy group such as a benzyloxymethyl group or a 2-(benzyloxymethoxy) ethyl group, an alkyl group having an aryloxy group such as a phenyloxymethyl group, a 4-chlorophenyloxymethyl group, or a 4-(2'-phenyloxyethoxy) butyl group, an alkyl group having a thioalkyl group such as a n-butylthiomethyl group or a 2-n-octylthioethyl group, and an alkyl group having a halogen atom such as a fluoromethyl group, a trifluoromethyl group, a perfluoroethyl group, a 4-fluorocyclohexyl group, a dichloromethyl group, a 4-chlorocyclohexyl group, or a 7-chloroheptyl group.

In General Formula (1) and General Formulae (1)-a to (1)-d, A represents Formula (2).

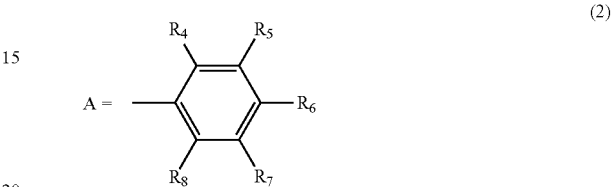

(2)

In Formula (2), $R_4$ to $R_8$ each independently represent a hydrogen atom, a halogen atom, a substituted or unsubstituted linear, branched, or cyclic alkyl group, a substituted or unsubstituted linear, branched, or cyclic alkoxy group, a substituted or unsubstituted linear, branched, or cyclic alkylthio group, an aryloxy group which optionally have a substituent, or an arylthio group which optionally have a substituent, and $R_4$ to $R_8$ do not simultaneously represent a hydrogen atom.

In Formula (2), each of $R_4$ to $R_8$ preferably represents a hydrogen atom, a fluorine atom, a chlorine atom, a bromine atom, a substituted or unsubstituted linear, branched, or cyclic alkyl group having 1 to 12 carbon atoms, a substituted or unsubstituted linear, branched, or cyclic alkoxy group having 1 to 12 carbon atoms, a substituted or unsubstituted linear, branched, or cyclic alkylthio group having 1 to 12 carbon atoms, a substituted or unsubstituted aryloxy group having 6 to 20 carbon atoms, or a substituted or unsubstituted arylthio group having 6 to 20 carbon atoms, and more preferably represents a substituted or unsubstituted linear, branched, or cyclic alkyl group having 1 to 8 carbon atoms, a substituted or unsubstituted linear, branched, or cyclic alkoxy group having 1 to 8 carbon atoms, a substituted or unsubstituted linear, branched, or cyclic alkylthio group having 1 to 8 carbon atoms, a substituted or unsubstituted aryloxy group having 6 to 16 carbon atoms, or a substituted or unsubstituted arylthio group having 6 to 16 carbon atoms.

As the substituent of the aryloxy group or the arylthio group which optionally have a substituent, a halogen atom, a substituted or unsubstituted linear, branched, or cyclic alkyl group having 1 to 12 carbon atoms, and a substituted or unsubstituted linear, branched, or cyclic alkoxy group having 1 to 12 carbon atoms are preferable. These substituents optionally be monosubstituted or polysubstituted for the aryl group.

Examples of the halogen atom and the substituted or unsubstituted linear, branched, or cyclic alkyl group of $R_4$ to $R_1$ are the same exemplified in $R_1$ to $R_3$.

Examples of the linear, branched, or cyclic alkoxy group of $R_4$ to R include a methoxy group, an ethoxy group, a n-propyloxy group, an isopropyloxy group, a n-butyloxy group, an isobutyloxy group, a tert-butyloxy group, a sec-butyloxy group, a n-pentyloxy group, an isopentyloxy group, a n-hexyloxy group, a 2-methylpentyloxy group, a 1,1-dimethylbutyloxy group, a 1,2,2-trimethylpropyloxy group, a 2-ethylbutyloxy group, a 1,3-dimethylhexyloxy group, a cyclohexyloxy group, a methyl cyclopentyloxy group, a n-heptyloxy group, a n-heptyloxy group, a n-octyloxy group, a 3,5,5-trimethylhexyloxy group, a n-decyloxy group, a n-undecyloxy group, a n-dodecyloxy group, a 1-adamantyloxy group, a n-pentadecyloxy group, and the like.

Examples of the linear, branched, or cyclic alkylthio group represented by $R_4$ to $R_8$ include a methylthio group, an ethylthio group, a n-propylthio group, an isopropylthio group, a n-butylthio group, an isobutylthio group, a tert-butylthio group, a sec-butylthio group, a n-pentylthio group, an isopentylthio group, a n-hexylthio group, a 2-methylpentylthio group, a 1,1-dimethylbutylthio group, a 1,2,2-trimethylpropylthio group, a 2-ethylbutylthio group, a 1,3-dimethylhexylthio group, a cyclohexylthio group, a methyl cyclopentylthio group, a n-heptylthio group, a n-heptylthio group, a n-octylthio group, a 3,5,5-trimethylhexylthio group, a n-decylthio group, a n-undecylthio group, a n-dodecylthio group, a 1-adamantylthio group, a n-pentadecylthio group, and the like.

Examples of the aryloxy group having a substituent represented by $R_4$ to $R_8$ include a phenyloxy group, a 2-methylphenyloxy group, a 4-methylphenyloxy group, a 4-ethylphenyloxy group, a 4-isopropylphenyloxy group, a 4-isobutylphenyloxy group, a 4-n-pentylphenyloxy group, a 4-tert-pentylphenyloxy group, a 4-cyclohexylphenyloxy group, a 4-n-octylphenyloxy group, a 4-n-decylphenyloxy group, a 4-n-dodecylphenyloxy group, a 4-n-hexadecylphenyloxy group, a 2,3-dimethylphenyloxy group, a 2,5-dimethylphenyloxy group, a 3,4-dimethylphenyloxy group, a 3,4,5-trimethylphenyloxy group, a 5-indanyloxy group, a 1,2,3,4-tetrahydro-6-naphthyloxy group, a 3-methoxyphenyloxy group, a 3-ethoxyphenyloxy group, a 4-n-propoxyphenyloxy group, a 4-n-butoxyphenyloxy group, a 4-n-pentyloxyphenyloxy group, a 4-cyclohexyloxyphenyloxy group, a 4-n-octyloxyphenyloxy group, a 4-n-decyloxyphenyloxy group, a 4-n-dodecyloxyphenyloxy group, a 4-n-hexadecyloxyphenyloxy group, a 2,3-dimethoxyphenyloxy group, a 2,5-dimethoxyphenyloxy group, a 3,5-dimethoxyphenyloxy group, a 2-methoxy-4-methylphenyloxy group, a 3-methoxy-4-methylphenyloxy group, a 3-methyl-4-methoxyphenyloxy group, a 2-flurophenyloxy group, a 4-fluorophenyloxy group, a 3-chlorophenyloxy group, a 4-bromophenyloxy group, a 3-trifluoromethylphenyloxy group, a 3,5-difluorophonyloxy group, a 3,4-dichlorophenyloxy group, a 2-methyl-4-chlorophenyloxy group, a 3-chloro-4-methylphenyloxy group, a 3-methoxy-4-fluorophenyloxy group, a 3-fluoro-4-methoxyphenyloxy group, a 1-naphthyloxy group, a 4-methyl-1-naphthyloxy group, a 6-n-butyl-2-naphthyloxy group, a 7-ethoxy-2-naphthyloxy group, a 2-thienyloxy group, a 2-pyridyloxy group, a 4-pyridyloxy group, and the like.

Examples of the arylthio group having a substituent represented by $R_4$ to $R_8$ include a phenylthio group, a 2-methylphenylthio group, a 4-methylphenylthio group, a 3-ethylphenylthio group, a 4-n-propylphenylthio group, a 4-n-butylphenylthio group, a 4-isobutylphenylthio group, a 4-tert-butylphenylthio group, a 4-n-pentylphenylthio group, a 4-n-hexylphenylthio group, a 4-cyclohexylphenylthio group, a 4-n-octylphenylthio group, a 4-n-dodecylphenylthio group, a 4-n-octadecylphenylthio group, a 2,5-dimethylphenylthio group, a 3,4-dimethylphenylthio group, a 5-indanylthio group, a 1,2,3,4-tetrahydro-6-naphthylthio group, a 2-methoxyphenylthio group, a 3-methoxyphenylthio group, a 4-ethoxyphenylthio group, a 4-n-propoxyphenylthio group, a 2,4-dimethoxyphenylthio group, a 3,5-diethoxyphenylthio group, a 2-methoxy-4-methylphenylthio group, a 2-methyl-4-methoxyphenylthio group, a 2-fluorophenylthio group, a 4-fluorophenylthio group, a 2-chlorophenylthio group, a 4-bromophenylthio group, a 4-trifluoromethylphenylthio group, a 3-trifluoromethylphenylthio group, a 2,4-difluorophenylthio group, a 2,4-dichlorophenylthio group, a 2-chloro-4-methoxyphenylthio group, a 2-naphthylthio group, a 4-methyl-1-naphthylthio group, a 4-ethoxy-1-naphthylthio group, a 2-pyridylthio group, and the like.

In General Formula (1) and General Formulae (1)-a to (1)-d, B represents Formula (3).

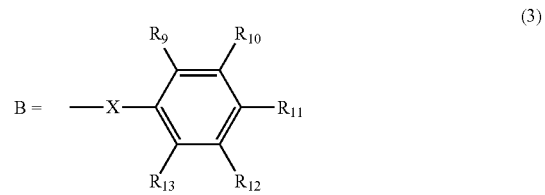

In Formula (3), X represents an oxygen atom, a sulfur atom, or a substituted or unsubstituted imino group, $R_9$ to $R_{13}$ each independently represent a hydrogen atom, a halogen atom, a substituted or unsubstituted alkyl group, a substituted or unsubstituted alkoxy group, an ester group ($COOX_1$ in which $X_1$ represents a hydrogen atom, a substituted or unsubstituted alkyl group, or a substituted or unsubstituted aryl group), an amide group ($CONX_2X_3$ in which $X_2$ and $X_3$ each independently represent a hydrogen atom, a substituted or unsubstituted alkyl group, or a substituted or unsubstituted aryl group), or a sulfonamide group ($SO_2NX_4X_5$ in which $X_4$ and $X_5$ each independently represent a hydrogen atom, a substituted or unsubstituted alkyl group, or a substituted or unsubstituted aryl group), and $R_9$ to $R_{13}$ do not simultaneously represent a hydrogen atom.

In Formula (3), X preferably represents an oxygen atom, a sulfur atom, or an imino group, and more preferably represents an oxygen atom.

Specific examples of the imino group include an imino group, a methylimino group, an ethylimino group, a n-propylimino group, a n-butylimino group, an isobutylimino group, a n-pentylimino group, an isopentylimino group, a n-heptylimino group, an isoheptylimino group, a n-octylimino group, an isooctylimino group, and the like.

Each of $R_9$ to $R_{13}$ preferably represents a fluorine atom, a chlorine atom, a bromine atom, a linear, branched, or cyclic alkyl group having 1 to 12 carbon atoms, a linear, branched, or cyclic alkoxy group having 1 to 12 carbon atoms, a linear, branched, or cyclic ester group having 1 to 12 carbon atoms, a linear, branched, or cyclic amide group having 1 to 24 carbon atoms, or a linear, branched, or cyclic sulfonamide group having 1 to 12 carbon atoms, and more preferably represents a fluorine atom, a chlorine atom, a linear, branched, or cyclic alkyl group having 1 to 8 carbon atoms, a linear, branched, or cyclic alkoxy group having 1 to 8 carbon atoms, a linear, branched, or cyclic ester group having 1 to 8 carbon atoms, a linear, branched, or cyclic amide group having 1 to 16 carbon atoms, or a linear, branched, or cyclic sulfonamide group having 1 to 8 carbon atoms. The alkyl group may be substituted with an alkyloxy group.

Specific examples of the halogen atom, the substituted or unsubstituted linear, branched, or cyclic alkyl group, and the substituted or unsubstituted linear, branched, or cyclic alkoxy group represented by $R_9$ to $R_{13}$ are the same exemplified in $R_4$ to $R_8$.

Examples of the substituted alkyl group represented by $R_9$ to $R_{13}$ include a methyl carbonyl methyl group, a methyl carbonyl ethyl group, a methyl carbonyl propyl group, a methyl carbonyl butyl group, a methyl carbonyl pentyl group, an ethyl carbonyl methyl group, an ethyl carbonyl ethyl group, an ethyl carbonyl propyl group, an ethyl carbonyl butyl group, an ethyl carbonyl pentyl group, a n-propyl carbonyl methyl group, a n-propyl carbonyl ethyl group, a n-propyl carbonyl propyl group, a n-propyl carbonyl butyl group, a n-propyl carbonyl pentyl group, an isopropyl carbonyl methyl group, a n-butyl carbonyl ethyl group, an isobutyl carbonyl propyl group, a sec-butyl carbonyl butyl group, a t-butyl carbonyl pentyl group, a n-pentyl carbonyl methyl group, an isopentyl carbonyl ethyl group, a neopentyl carbonyl propyl group, a methoxymethyl carbonyl methyl group, an ethoxymethyl carbonyl methyl group, a n-propoxymethyl carbonyl methyl group, a n-butoxymethyl carbonyl methyl group, a phenyl carbonyl butyl group, a 4-methylphenyl carbonyl pentyl group, a 4-chlorophenyl carbonyl ethyl group, and the like.

Specific examples of the amide group include a methylamide group, an ethyl amid group, a n-propylamide group, an isopropylamide group, a n-butylamide group, an isobutylamide group, a t-butylamide group, a sec-butyl amide group, a n-pentyl amide group, an isopentyl amide group, a t-pentylamide group, a neopentyl amide group, a cyclopentyl amide group, a n-hexyl amide group, an isohexyl amide group, a cyclohexyl amide group, a 4-methylcyclohexyl amide group, a n-octyl amide group, a 2-ethylhexyl amide group, a N,N-dimethyl amide group, a N,N-diethyl amide group, a N,N-di-n-propyl amide group, a N,N-di-n-butyl amide group, a N,N-ethylmethyl amide group, a N,N-ethylbutyl amide group, a N,N-ethylisopentyl amide group, a N,N-di-n-penthyl amide group, a N,N-di-n-hexyl amide group, a N,N-methylcyclohexylamide group, a N,N-dimethoxyethyl amide group, a N,N-di-ethoxyethyl amide group, a N,N-di-n-propoxyethyl amide group, a N,N-di-n-butoxyethyl amide group, a phenyl amide group, a 4-methylphenyl amide group, a 4-fluorophenyl amide group, a 4-methoxyphenyl amide group, a N,N-methylphenyl amide group, and the like.

Specific examples of the ester group include a methyl ester group, an ethyl ester group, a n-propyl ester group, an isopropyl ester group, a n-butyl ester group, an isobutyl ester group, a sec-butyl ester group, a t-butyl ester group, a n-pentyl ester group, an isopentyl ester group, a neopentyl ester group, a cyclopentyl ester group, a n-hexyl ester group, an isohexyl ester group, a cyclohexyl ester group, a n-octyl ester group, an isooctyl ester group, a 2-ethylhexyl ester group, a phenyl ester group, a 4-methylphenyl ester group, a 4-fluorophenyl ester group, a 4-methoxyphenyl ester group, and the like.

Specific examples of the sulfonamide group include a methyl sulfonamide group, an ethyl sulfonamide group, a n-propyl sulfonamide group, an isopropyl sulfonamide group, a n-butyl sulfonamide group, an isobutyl sulfonamide group, a t-butyl sulfonamide group, a sec-butyl sulfonamide group, a n-pentyl sulfonamide group, an isopentyl sulfonamide group, a t-pentyl sulfonamide group, a neopentyl sulfonamide group, a cyclopentyl sulfonamide group, a n-hexyl sulfonamide group, an isohexyl sulfonamide group, a cyclohexyl sulfonamide group, a 4-methylcyclohexyl sulfonamide group, a n-octyl sulfonamide group, a 2-ethylhexyl sulfonamide group, a methoxyethyl sulfonamide group, an ethoxyethyl sulfonamide group, an ethoxypropyl sulfonamide group, a n-propoxyethyl sulfonamide group, n-propoxypropyl sulfonamide group, a n-butoxyethyl sulfonamide group, a n-butoxypropyl sulfonamide group, a N,N-dimethyl sulfonamide group, a N,N-diethyl sulfonamide group, a N,N-di-n-propyl sulfonamide group, a N,N-di-n-butyl sulfonamide group, a N,N-ethylmethyl sulfonamide group, a N,N-ethylbutyl sulfonamide group, a N,N-ethylisopentyl sulfonamide group, a N,N-di-n-pentyl sulfonamide group, a N,N-di-n-hexyl sulfonamide group, a N,N-methylcyclohexyl sulfonamide group, a phenyl sulfonamide group, a 4-methylphenyl sulfonamide group, a 4-fluorophenyl sulfonamide group, a 4-methoxyphenyl sulfonamide group, a N,N-methylphenyl sulfonamide group, and the like.

Specific examples of the naphthalocyanine compound represented by General Formula (1) of the present invention will be shown in the following Table 1, but the present invention is not limited thereto.

As described above, the naphthalocyanine compound represented by General Formula (1) is one kind of isomer represented by any of General Formulae (1)-a to (1)-d or a mixture of two or more kinds of isomers represented by General Formulae (1)-a to (1)-d. In a case where the naphthalocyanine compound is a mixture of isomers, the absorption band of the compound in a near-infrared range broadens further than in a case where the naphthalocyanine compound is a single isomer. Depending on the use of the compound such as a heat ray shielding resin, a mixture of isomers having a broad absorption band is preferable.

Specific examples shown in the following Table 1 include isomers described above and a mixture of two or more kinds of isomers described above.

TABLE 1

| Specific example | M | $R_1$ | $R_2$ | $R_3$ | $R_4$ | $R_5$ | $R_6$ | $R_7$ |
|---|---|---|---|---|---|---|---|---|
| (1)-1 | Cu | H | t-$C_4H_9$ | H | H | H | H | F |
| (1)-2 | VO | H | t-$C_4H_9$ | H | H | H | H | F |
| (1)-3 | Zn | H | t-$C_4H_9$ | H | H | H | H | F |
| (1)-4 | VO | H | t-$C_4H_9$ | H | H | H | H | H |
| (1)-5 | $H_2$ | H | t-$C_4H_9$ | H | H | H | H | H |
| (1)-6 | Cu | H | t-$C_4H_9$ | H | H | H | H | H |
| (1)-7 | In—Cl | H | t-$C_4H_9$ | H | H | H | H | H |
| (1)-8 | Cu | H | t-$C_4H_9$ | H | H | H | H | H |
| (1)-9 | VO | H | t-$C_4H_9$ | H | H | $CF_3$ | H | $CF_3$ |
| (1)-10 | Pd | H | t-$C_4H_9$ | H | H | H | H | H |
| (1)-11 | Cu | H | t-$C_4H_9$ | H | H | $CF_3$ | H | $CF_3$ |
| (1)-12 | VO | H | t-$C_4H_9$ | H | H | $CF_3$ | H | $CF_3$ |
| (1)-13 | Fe | Cl | Cl | H | H | H | H | H |
| (1)-14 | Co | Cl | Cl | H | H | H | H | H |

TABLE 1-continued

| | | | | | | | | |
|---|---|---|---|---|---|---|---|---|
| (1)-15 | Ni | t-C$_4$H$_9$ | Cl | H | H | H | H | OC$_2$H$_5$ |
| (1)-16 | Pt | t-C$_4$H$_9$ | Cl | H | H | H | n-C$_5$H$_{11}$ | H |
| (1)-17 | Cu | H | iso-C$_5$H$_{11}$ | H | H | H | H | H |
| (1)-18 | TiO | H | iso-C$_5$H$_{11}$ | H | H | H | H | H |
| (1)-19 | Mn | H | iso-C$_5$H$_{11}$ | H | H | H | H | H |
| (1)-20 | Sn | H | t-C$_4$H$_9$ | H | H | 4-F-cyclohexyl | H | 4-F-cyclohexyl |
| (1)-21 | Cu | H | t-C$_4$H$_9$ | H | H | 4-F-cyclohexyl | H | 4-F-cyclohexyl |
| (1)-22 | Al—Cl | H | t-C$_4$H$_9$ | H | H | H | H | 3-OCH$_3$-phenoxy |
| (1)-23 | VO | H | t-C$_4$H$_9$ | H | H | H | H | 3-C$_2$H$_5$-phenoxy |
| (1)-24 | Pd | H | t-C$_8$H$_{17}$ | H | H | H | H | H |
| (1)-25 | Co | H | t-C$_8$H$_{17}$ | H | H | H | H | H |
| (1)-26 | Fe | H | t-C$_4$H$_9$ | H | H | H | H | CF$_3$ |
| (1)-27 | Ni | Cl | Cl | H | H | H | H | H |
| (1)-28 | Cu | H | t-C$_4$H$_9$ | H | H | CF$_3$ | H | CF$_3$ |
| (1)-29 | VO | H | t-C$_4$H$_9$ | H | H | CF$_3$ | H | CF$_3$ |
| (1)-30 | Cu | H | t-C$_4$H$_9$ | H | H | H | H | H |
| (1)-31 | Cu | t-C$_4$H$_9$ | Cl | H | H | H | H | n-C$_4$H$_9$ |
| (1)-32 | VO | H | t-C$_4$H$_9$ | H | H | CF$_3$ | H | CH$_2$CF$_3$ |
| (1)-33 | Zn | H | t-C$_4$H$_9$ | H | H | CF$_3$ | H | CH$_2$CF$_3$ |
| (1)-34 | H$_2$ | H | t-C$_5$H$_{11}$ | H | H | H | H | H |
| (1)-35 | Pt | Cl | Cl | H | H | OCH$_3$ | H | OCH$_3$ |
| (1)-36 | TiO | Cl | Cl | H | H | H | OC$_2$H$_5$ | H |
| (1)-37 | Cu | H | n-C$_4$H$_9$ | H | H | F | H | 4-F-cyclohexyl |
| (1)-38 | Mn | n-C$_4$H$_9$ | H | H | H | F | H | 4-F-cyclohexyl |
| (1)-39 | Pd | H | n-C$_4$H$_9$ | H | H | H | H | 2-(OC$_2$H$_5$)-phenylthio |

TABLE 1-continued

| | | | | | | | | |
|---|---|---|---|---|---|---|---|---|
| (1)-40 | Fe | t-C$_4$H$_9$ | H | H | H | H | H | 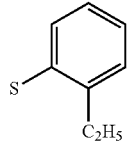 |
| (1)-41 | Al—Cl | H |  | H | H | H | H | SC$_2$H$_5$ |
| (1)-42 | Cu | H | t-C$_4$H$_9$ | H | H | CF$_3$ | H | CF$_3$ |
| (1)-43 | VO | H | Cl | H | H | H | H | CF$_3$ |
| (1)-44 | Zn | Cl | Cl | H | H | H | H | H |
| (1)-45 | Co | t-C$_4$H$_9$ | Cl | H | H | H | H | n-C$_4$H$_9$ |
| (1)-46 | Pd | H | t-C$_4$H$_9$ | H | H | F | H | 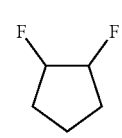 |
| (1)-47 | Cu | H | t-C$_4$H$_9$ | H | H | CF$_3$ | H | CH$_3$CF$_3$ |
| (1)-48 | VO | H | t-C$_8$H$_{17}$ | H | H | H | H | H |
| (1)-49 | Ni | H | t-C$_4$H$_9$ | H | H | H | H | CF$_3$ |
| (1)-50 | Cu | H | t-C$_4$H$_9$ | H | H | CF$_3$ | H | CF$_3$ |
| (1)-51 | VO | H | t-C$_4$H$_9$ | H | H | CF$_3$ | H | CF$_3$ |
| (1)-52 | Cu | H | t-C$_4$H$_9$ | H | H | H | H | H |
| (1)-53 | Zn | t-C$_4$H$_9$ | Cl | H | H | H | H | CH$_2$CF$_3$ |
| (1)-54 | VO | H | t-C$_5$H$_{11}$ | H | H | H | H | H |
| (1)-55 | Pd | t-C$_4$H$_9$ | Cl | H | H | H | CF$_3$ | H |
| (1)-56 | Pt | t-C$_4$H$_9$ | H | H | H | H | H | CF$_3$ |
| (1)-57 | Co |  | H | H | H | H | H | H |
| (1)-58 | Cu |  | H | H | H | H | H | H |
| (1)-59 | Zn | H | t-C$_4$H$_9$ | H | H | F | H | F |
| (1)-60 | VO | t-C$_4$H$_9$ | H | H | H | CF$_3$ | H | CF$_3$ |
| (1)-61 | Cu | H | t-C$_4$H$_9$ | H | H | H | H | H |
| (1)-62 | VO | H | t-C$_4$H$_9$ | H | H | H | H | H |
| (1)-63 | Co | H | t-C$_8$H$_{17}$ | H | H | H | H | F |
| (1)-64 | Zn | Cl | Cl | H | H | H | H | H |
| (1)-65 | Cu | H | t-C$_4$H$_9$ | H | H | CF$_3$ | H | CF$_3$ |
| (1)-66 | VO | H | t-C$_4$H$_9$ | H | H | CF$_3$ | H | CF$_3$ |
| (1)-67 | Pd | Cl | Cl | H | H | H | H | CF$_3$ |
| (1)-68 | Fe | Cl | Cl | H | H | CF$_3$ | H | CF$_3$ |
| (1)-69 | Ni | H | t-C$_5$H$_{11}$ | H | H | H | H | H |
| (1)-70 | Cu | H | t-C$_5$H$_{11}$ | H | H | OCH$_3$ | H | OCH$_3$ |
| (1)-71 | Co | H | t-C$_4$H$_9$ | H | H | CF$_3$ | H | 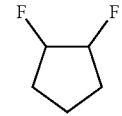 |
| (1)-72 | Pt | H |  | H | H | H | H | H |
| (1)-73 | VO | t-C$_4$H$_9$ | H | H | H | H | H | CH$_2$CF$_2$H |
| (1)-74 | Zn | t-C$_4$H$_9$ | Cl | H | H | H | H | CH$_2$CF$_2$H |
| (1)-75 | Cu | t-C$_4$H$_9$ | Cl | H | H | H | H | CH$_2$CF$_2$H |
| (1)-76 | VO | Cl | t-C$_4$H$_9$ | H | H | CH$_2$CF$_3$ | H | CH$_2$CF$_3$ |
| (1)-77 | Cu | H | t-C$_4$H$_9$ | H | H | H | H | H |

TABLE 1-continued

| Specific example | | | | | | | | |
|---|---|---|---|---|---|---|---|---|
| (1)-78 | Co | H | n-$C_4H_9$ | H | H | $CF_3$ | H | $CF_3$ |
| (1)-79 | Fe | t-$C_4H_9$ | H | H | H | H | H | $CH_2CF_2H$ |
| (1)-80 | Ni | Cl | Cl | H | H | $OCH_3$ | H | $OCH_3$ |

| Specific example | $R_8$ | X | $R_9$ | $R_{10}$ | $R_{11}$ | $R_{12}$ | $R_{13}$ |
|---|---|---|---|---|---|---|---|
| (1)-1 | H | O | H | H | $C_2H_4COCH_3$ | H | H |
| (1)-2 | H | O | H | H | $C_2H_4COCH_3$ | H | H |
| (1)-3 | H | O | H | H | $C_2H_4COCH_3$ | H | H |
| (1)-4 | F | O | H | H | $C_2H_4COCH_3$ | H | H |
| (1)-5 | F | O | H | H | $C_2H_4COCH_3$ | H | H |
| (1)-6 | F | O | H | H | $C_2H_4COCH_3$ | H | H |
| (1)-7 | F | O | H | H | $C_2H_4COCH_3$ | H | H |
| (1)-8 | F | O | H | H | H | $C_2H_4COCH_3$ | H |
| (1)-9 | H | O | H | H | H | OCH3 | H |
| (1)-10 | F | O | H | H | H | $C_2H_4COCH_3$ | H |
| (1)-11 | H | O | H | H | $C_2H_4COCH_3$ | H | H |
| (1)-12 | H | O | H | H | $C_2H_4COCH_3$ | H | H |
| (1)-13 | F | O | H | H | H | $C_2H_4COCH_3$ | H |
| (1)-14 | F | O | H | H | H | $C_2H_4COCH_3$ | H |
| (1)-15 | H | O | H | H | $COCH_2OC_2H_5$ | H | H |
| (1)-16 | H | O | H | H | $COCH_2OC_2H_5$ | H | H |
| (1)-17 | $CH_2CF_3$ | S | $CH_2COC_2H_5$ | H | H | H | H |
| (1)-18 | $CH_2CF_3$ | S | $CH_2COC_2H_5$ | H | H | H | H |
| (1)-19 | $CH_2CF_3$ | S | $CH_2COC_2H_5$ | H | H | H | H |
| (1)-20 | H | O | H | H | H | $C_3H_6COCH_3$ | H |
| (1)-21 | H | O | H | H | H | $C_3H_6COCH_3$ | H |
| (1)-22 | H | NH | H | H | $CH_2COC_2H_5$ | H | H |
| (1)-23 | H | NH | H | H | $CH_2COC_2H_5$ | H | H |
| (1)-24 | Cl | O | H | H | H | $CO_2C_6H_5$ | H |
| (1)-25 | Cl | O | H | H | H | $CO_2C_4H_9$ | H |
| (1)-26 | H | S | $CO_2C_5H_{11}$ | H | H | H | H |
| (1)-27 | $CF_3$ | O | H | H | H | $CO_2C_4H_9$ | H |
| (1)-28 | H | O | H | H | $CO_2C_4H_9$ | H | H |
| (1)-29 | H | O | H | H | $CO_2C_4H_9$ | H | H |
| (1)-30 | F | O | H | H | $CO_2C_4H_9$ | H | H |
| (1)-31 | H | O | H | H | $CO_2C_5H_{11}$ | H | H |
| (1)-32 | H | O | H | H | $CO_2C_6H_{13}$ | H | H |
| (1)-33 | H | O | H | H | $CO_2C_6H_{13}$ | H | H |
| (1)-34 | $CH_2CF_3$ | S | $CO_2C_4H_9$ | H | H | H | H |
| (1)-35 | H | O | H | H | $CO_2C_6H_{13}$ | H | H |
| (1)-36 | H | O | H | H | $CO_2C_6H_{13}$ | H | H |
| (1)-37 | H | O | H | H | H | $CO_2C_4H_9$ | H |
| (1)-38 | H | O | H | H | $CO_2C_4H_9$ | H | H |
| (1)-39 | H | O | H | H | H | $CO_2C_5H_{11}$ | H |
| (1)-40 | H | O | H | H | H | $CO_2C_5H_{11}$ | H |
| (1)-41 | H | O | H | H | $CO_2C_4H_9$ | H | H |
| (1)-42 | H | O | H | H | H | $CO_2C_2H_4OC_2H_5$ | H |
| (1)-43 | H | NH | H | H | $CO_2C_2H_4OC_2H_5$ | H | H |
| (1)-44 | $CF_3$ | O | H | H | H | $CO_2C_2H_4OC_2H_5$ | H |
| (1)-45 | H | O | H | H | H | $CO_2C_3H_6OC_2H_5$ | H |
| (1)-46 | H | O | H | H | H | $CO_2C_2H_4OC_2H_5$ | H |
| (1)-47 | H | O | H | H | $CO_2C_2H_4OC_2H_5$ | H | H |
| (1)-48 | Cl | O | H | H | $CONHC_4H_9$ | H | H |
| (1)-49 | H | S | H | H | H | $CON(C_4H_9)_2$ | H |
| (1)-50 | H | O | H | H | $CON(C_6H_{13})_2$ | H | H |
| (1)-51 | H | O | H | H | $CON(C_6H_{13})_2$ | H | H |
| (1)-52 | F | O | H | H | $CON(C_6H_{13})_2$ | H | H |
| (1)-53 | H | O | H | H | $CONHC_6H_5$ | H | H |
| (1)-54 | $CH_2CF_3$ | S | H | H | H | $CON(C_5H_{11})_2$ | H |
| (1)-55 | H | O | H | H | $CON(C_3H_6OC_2H_5)_2$ | H | H |
| (1)-56 | H | O | H | H | H | $CON(C_3H_6OC_2H_5)_2$ | H |
| (1)-57 | $CH_2CF_2H$ | O | H | H | $CON(C_6H_{13})_2$ | H | H |
| (1)-58 | F | O | H | H | $CON(C_6H_{13})_2$ | H | H |
| (1)-59 | H | O | $CON(C_2H_4OC_2H_5)_2$ | H | H | H | H |
| (1)-60 | H | O | H | H | H | $CON(C_2H_4OC_2H_5)_2$ | H |
| (1)-61 | F | O | H | H | $SO_2NHC_3H_6OC_2H_5$ | H | H |
| (1)-62 | F | O | H | H | $SO_2NHC_3H_6OC_2H_5$ | H | H |
| (1)-63 | H | O | H | H | H | $SO_2NHC_2H_4OC_2H_9$ | H |
| (1)-64 | $CF_3$ | O | H | H | $SO_2NHC_3H_6OC_2H_5$ | H | H |
| (1)-65 | H | O | H | H | $SO_2NHC_3H_6OC_2H_5$ | H | H |
| (1)-66 | H | O | H | H | $SO_2N(C_2H_5)_2$ | H | H |
| (1)-67 | H | S | $SO_2NHC_2H_4OC_2H_5$ | H | H | H | H |
| (1)-68 | H | NH | H | H | $SO_2NHC_6H_{13}$ | H | H |
| (1)-69 | $CH_2CF_3$ | S | H | H | $SO_2NHC_2H_4OC_2H_5$ | H | H |
| (1)-70 | H | O | H | H | $SO_2NHC_6H_4$ | H | H |
| (1)-71 | H | O | H | H | $SO_2NHC_2H_4OC_2H_5$ | H | H |
| (1)-72 | $CH_2CF_2H$ | O | H | H | $SO_2NHC_5H_{11}$ | H | H |
| (1)-73 | H | O | $SO_2NHC_2H_4OC_2H_5$ | H | H | H | H |

TABLE 1-continued

| | | | | | | | |
|---|---|---|---|---|---|---|---|
| (1)-74 | H | O | H | H | H | $SO_2NHC_2H_4OC_2H_5$ | H |
| (1)-75 | H | NH | H | H | H | $SO_2NHC_2H_4OC_2H_5$ | H |
| (1)-76 | H | O | H | H | $SO_2NHC_3H_6OC_2H_5$ | H | H |
| (1)-77 | F | S | H | H | H | $SO_2NHC_3H_6OC_2H_5$ | H |
| (1)-78 | H | O | H | H | H | $SO_2NHC_2H_4OC_2H_5$ | H |
| (1)-79 | H | O | $SO_2NHC_2H_4OC_2H_5$ | H | H | H | H |
| (1)-80 | H | O | H | H | H | $SO_2NHC_3H_6OC_2H_5$ | H |

[Process for Producing Naphthalocyanine Compound]

A second invention of the present invention is a process for producing a naphthalocyanine compound represented by any of General Formula (1) and General Formulae (1)-a to (1)-d by causing a reaction between a metal or a metal derivative and at least one kind of compounds selected from naphthalene-2,3-dicarbonitrile compound represented by General Formula (4) and a 1,3-diiminobenzisoindoline compound represented by General Formula (5).

The naphthalocyanine compound represented by any of General Formula (1) and General Formulae (1)-a to (1)-d can also be produced by forming a naphthalocyanine compound and then introducing a substituent B into the compound.

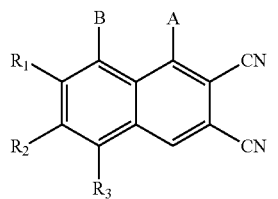

(4)

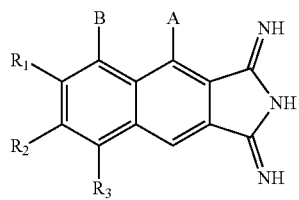

(5)

In Formulae (4) and (5), $R_1$ to $R_3$, A, and B have the same definition as $R_1$ to $R_3$, A, and B in General Formula (1).

Each of the naphthalene-2,3-dicarbonitrile compound represented by General Formula (4) and the 1,3-diiminobenzisoindoline compound represented by General Formula (5) will be described later.

Examples of the metal or the metal derivative include Al, Si, Ti, V, Mn, Fe, Co, Ni, Cu, Zn, Ge, Ru, Rh, Pd, In, Sn, Pt and Pb, and a halide, a carboxylate, a sulfate, a nitrate, a carbonyl compound, an oxide, and a complex of the metals listed above, and the like.

Particularly, a metal halide or a metal carboxylate is preferably used, and examples thereof include a copper chloride, copper bromide, copper iodide, nickel chloride, nickel bromide, nickel acetate, cobalt chloride, iron chloride, zinc chloride, zinc bromide, zinc iodide, zinc acetate, vanadium chloride, vanadium oxychloride, palladium chloride, palladium acetate, aluminum chloride, manganese chloride, lead chloride, lead acetate, indium chloride, titanium chloride, tin chloride, and the like.

The used amount of the metal or the metal derivative is 0.1 to 0.6 mol, and preferably 0.2 to 0.5 mol with respect to 1 mol of the naphthalene-2,3-dicarbonitrile compound represented by General Formula (4) or with respect to 1 mol of the 1,3-diiminobenzisoindoline compound represented by General Formula (5).

The reaction temperature is 60° C. to 300° C., and preferably 100° C. to 220° C.

The reaction time is 30 minutes to 72 hours, and preferably 1 to 48 hours.

It is preferable to use a solvent in the reaction. As the solvent used in the reaction, an organic solvent having a boiling point which is equal to or higher than 60° C. and preferably equal to or higher than 80° C. is preferable. Examples thereof include an alcohol solvent such as methanol, ethanol, n-propyl alcohol, n-butyl alcohol, isobutyl alcohol, n-amyl alcohol, n-hexanol, 1-heptanol, 1-octanol, 1-dodecanol, benzyl alcohol, ethylene glycol, propylene glycol, ethoxyethanol, propoxyethanol, butoxyethanol, dimethyl ethanol, or diethyl ethanol, and a solvent of high boiling point such as dichlorobenzene, trichlorobenzene, chloronaphthalene, sulfolane, nitrobenzene, quinoline, 1,3-dimethyl-2-imidazolidinone (DMI), or urea. The volume of the solvent is 0.5 to 50 times, and preferably 1 to 15 times with respect to the used volume of the naphthalene-2,3-dicarbonitrile compound represented by General Formula (4) or the 1,3-diiminobenzisoindoline compound represented by General Formula (5).

The reaction is performed in the presence or absence of a catalyst. It is preferable that the reaction is performed in the presence of a catalyst. As the catalyst, it is possible to use an inorganic catalyst such as ammonium molybdate or a basic organic catalyst such as 1,8-diazabicyclo[5.4.0]-7-undecene (DBU) or 1,5-diazabicyclo[4.3.0]-5-nonene (DBN). The molar quantity of the catalyst is 0.01 to 10 times, and preferably 1 to 2 times with respect to 1 mol of the naphthalene-2,3-dicarbonitrile compound or 1 mol of the 1,3-diiminobenzisoindoline compound.

The naphthalocyanine compound in which M represents two hydrogen atoms can be produced by causing a reaction between metallic sodium or metallic potassium and at least one kind of compounds selected from the naphthalene-2,3-dicarbonitrile compound represented by General Formula (4) and the 1,3-diiminobenzisoindoline compound represented by General Formula (5) under the reaction conditions described above, and then treating the reaction solution with hydrochloric acid, sulfuric acid, and the like such that the sodium or the potassium as a central metal.

After the reaction ends, by distilling the solvent or adding the reaction solution to a poor solvent of a naphthalocyanine compound such that a target substance is precipitated, and filtering the precipitate, the naphthalocyanine compound represented by General Formula (1) can be obtained.

Generally, the naphthalocyanine compound is obtained as a mixture of the isomers represented by General Formulae (1)-a to (1)-d.

By purifying the compound by a known purification method such as recrystallization or column chromatography according to the purpose, a target substance with higher purity can be obtained. Furthermore, from the mixture of the isomers represented by General Formulae (1)-a to (1)-d, an intended single compound can be isolated by the purification method described above.

Naphthalene-2,3-dicarbonitrile Compound

A third invention of the present invention is a naphthalene-2,3-dicarbonitrile compound represented by General Formula (4).

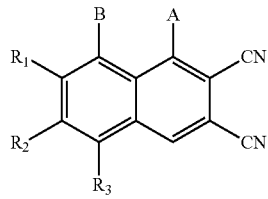

(4)

In Formula (4), $R_1$ to $R_3$, A, and B have the same definition as $R_1$ to $R_3$, A, and B in General Formula (1).

The naphthalene-2,3-dicarbonitrile compound represented by General Formula (4) is an intermediate used for producing the naphthalocyanine compound represented by any of General Formula (1) and General Formulae (1)-a to (1)-d.

In General Formula (4), preferred ranges and specific examples of $R_4$ to $R_8$ as substituents of A, $R_9$ to $R_{13}$ as substituents of B, and $R_1$ to $R_3$ are the same as the preferred ranges and specific examples of $R_4$ to $R_8$, $R_9$ to $R_{13}$, and $R_1$ to $R_3$ shown in General Formula (1) and General Formulae (1)-a to (1)-d.

Specific examples of the naphthalene-2,3-dicarbonitrile compound represented by General Formula (4) are shown in the following Table 2, but the present invention is not limited thereto.

TABLE 2

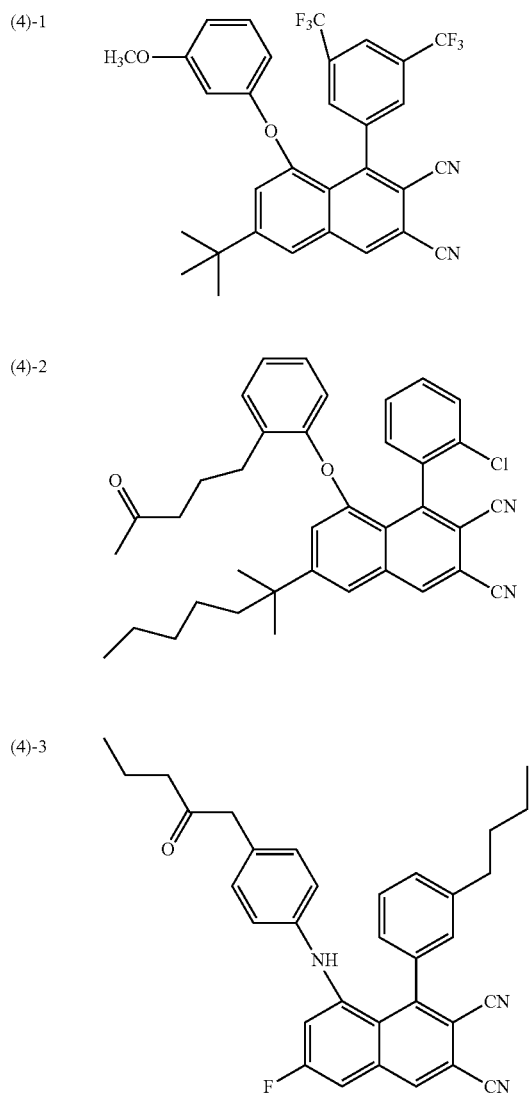

TABLE 2-continued
(4)-4
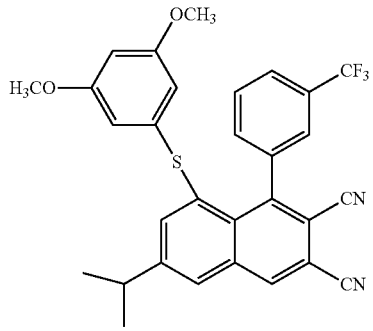 [SMILES: COc1cc(OC)cc(Sc2cc(C(C)C)cc3cc(C#N)c(C#N)c(-c4cccc(C(F)(F)F)c4)c23)c1]
(4)-5
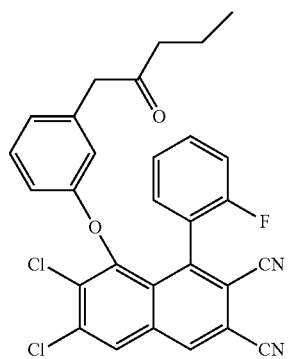 [SMILES: CCCC(=O)Cc1cccc(Oc2c(Cl)c(Cl)cc3cc(C#N)c(C#N)c(-c4ccccc4F)c23)c1]
(4)-6
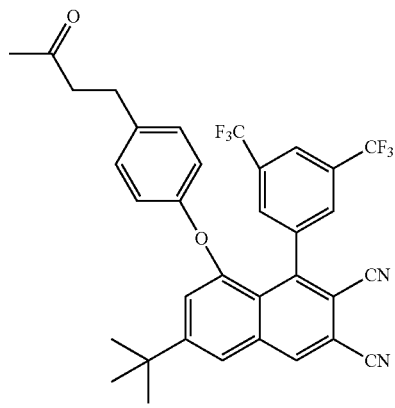 [SMILES: CC(=O)CCc1ccc(Oc2cc(C(C)(C)C)cc3cc(C#N)c(C#N)c(-c4cc(C(F)(F)F)cc(C(F)(F)F)c4)c23)cc1]
(4)-7
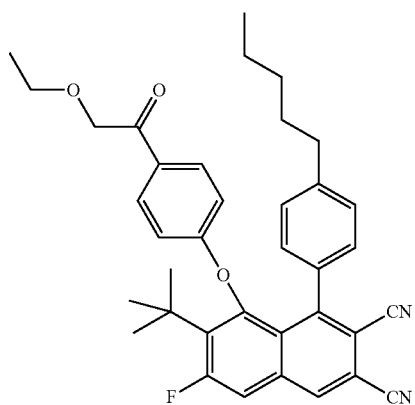 [SMILES: CCCCCc1ccc(-c2c(C#N)c(C#N)cc3cc(F)c(C(C)(C)C)c(Oc4ccc(C(=O)COCC)cc4)c23)cc1]

TABLE 2-continued
(4)-8 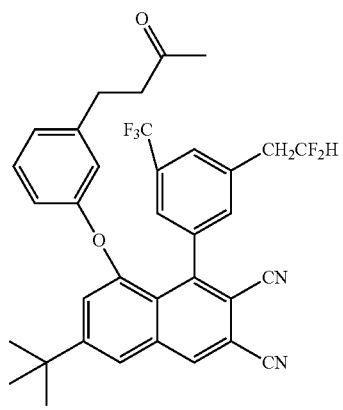
(4)-9 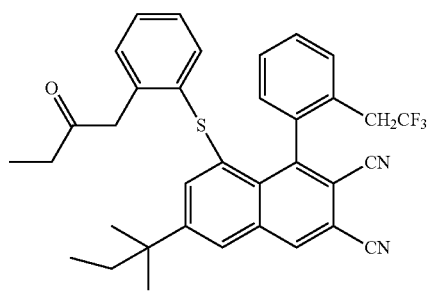
(4)-10 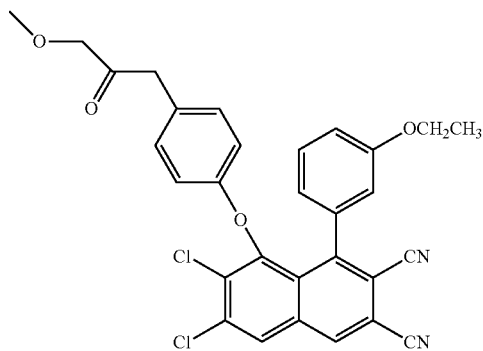 [SMILES: CCOc1cccc(-c2c(C#N)c(C#N)cc3cc(Cl)c(Cl)c(Oc4ccc(CC(=O)COC)cc4)c23)c1]
(4)-11 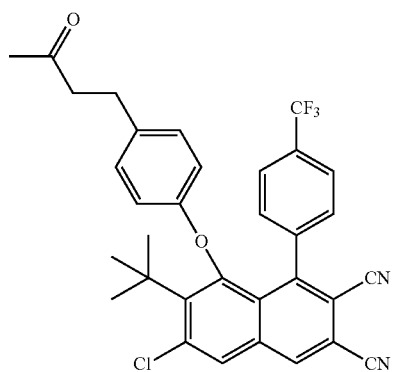 [SMILES: CC(=O)CCc1ccc(Oc2c(C(C)(C)C)c(Cl)cc3cc(C#N)c(C#N)c(-c4ccc(C(F)(F)F)cc4)c23)cc1]

TABLE 2-continued
(4)-12
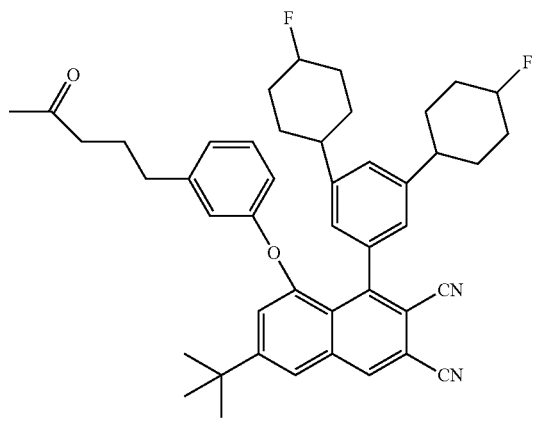 [SMILES: CC(=O)CCCc1cccc(Oc2cc(C(C)(C)C)cc3cc(C#N)c(C#N)c(-c4cc(C5CCC(F)CC5)cc(C5CCC(F)CC5)c4)c23)c1]
(4)-13
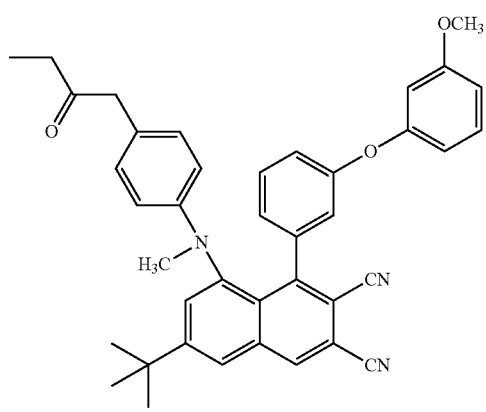 [SMILES: CCC(=O)Cc1ccc(N(C)c2cc(C(C)(C)C)cc3cc(C#N)c(C#N)c(-c4cccc(Oc5cccc(OC)c5)c4)c23)cc1]
(4)-14
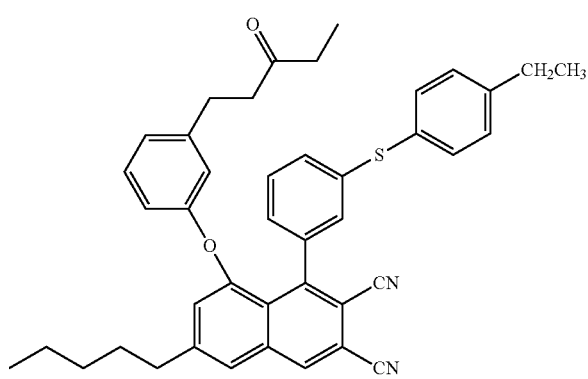 [SMILES: CCCCCc1cc(Oc2cccc(CCC(=O)CC)c2)c2c(-c3cccc(Sc4ccc(CC)cc4)c3)c(C#N)c(C#N)cc2c1]
(4)-15
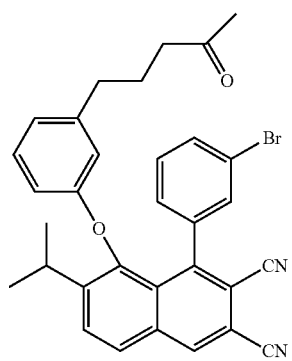 [SMILES: CC(=O)CCCc1cccc(Oc2c(C(C)C)ccc3cc(C#N)c(C#N)c(-c4cccc(Br)c4)c23)c1]

TABLE 2-continued
(4)-16
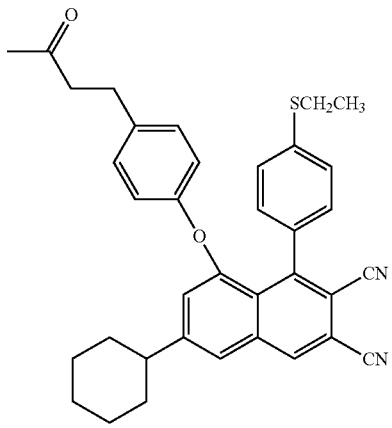
(4)-17
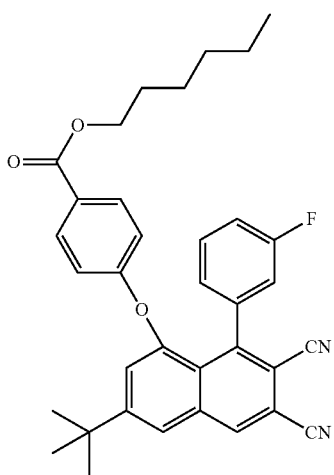 [SMILES: CCCCCCOC(=O)c1ccc(Oc2cc(C(C)(C)C)cc3cc(C#N)c(C#N)c(-c4cccc(F)c4)c23)cc1]
(4)-18
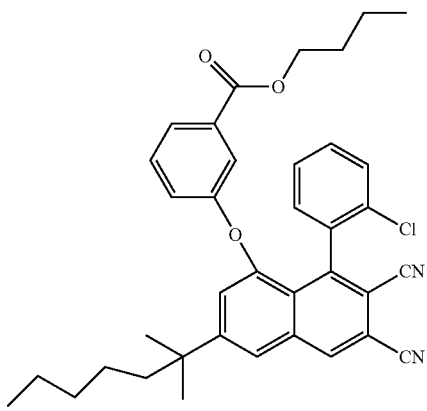 [SMILES: CCCCCC(C)(C)c1cc(Oc2cccc(C(=O)OCCCC)c2)c2c(-c3ccccc3Cl)c(C#N)c(C#N)cc2c1]

TABLE 2-continued
(4)-19
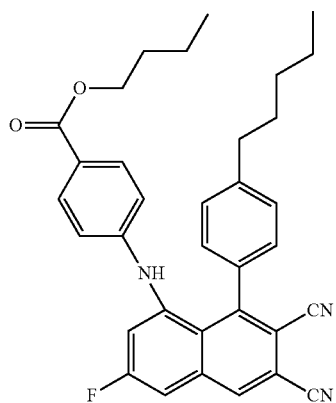 [SMILES: CCCCCc1ccc(-c2c(C#N)c(C#N)cc3cc(F)cc(Nc4ccc(C(=O)OCCCC)cc4)c23)cc1]
(4)-20
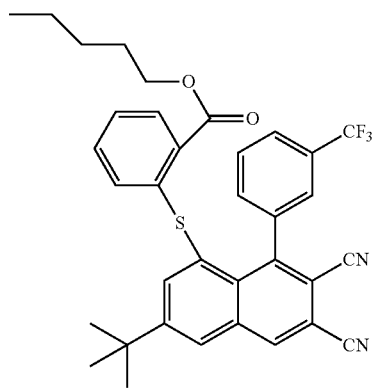 [SMILES: CCCCCOC(=O)c1ccccc1Sc1cc(C(C)(C)C)cc2cc(C#N)c(C#N)c(-c3cccc(C(F)(F)F)c3)c12]
(4)-21
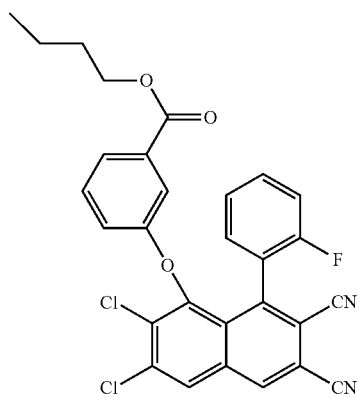 [SMILES: CCCCOC(=O)c1cccc(Oc2c(Cl)c(Cl)cc3cc(C#N)c(C#N)c(-c4ccccc4F)c23)c1]
(4)-22
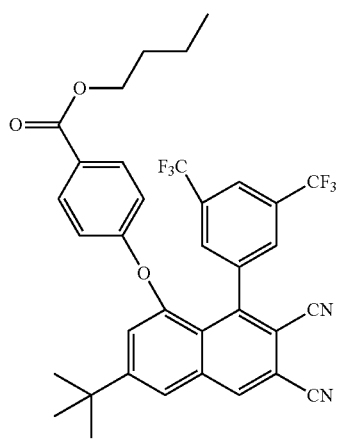 [SMILES: CCCCOC(=O)c1ccc(Oc2cc(C(C)(C)C)cc3cc(C#N)c(C#N)c(-c4cc(C(F)(F)F)cc(C(F)(F)F)c4)c23)cc1]

TABLE 2-continued
(4)-23
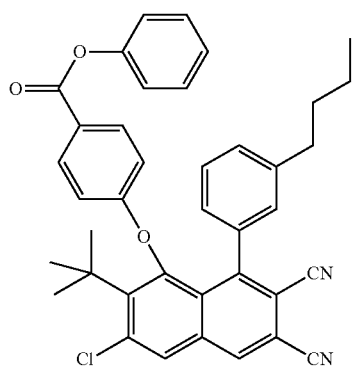 [SMILES: CCCCc1cccc(-c2c(C#N)c(C#N)cc3cc(Cl)c(C(C)(C)C)c(Oc4ccc(C(=O)Oc5ccccc5)cc4)c23)c1]
(4)-24
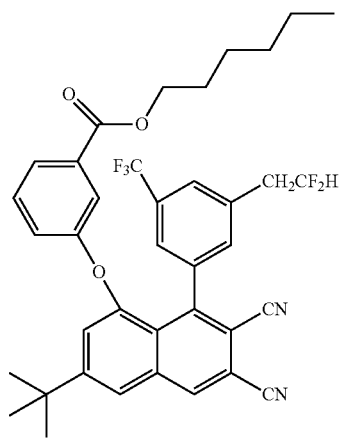
(4)-25
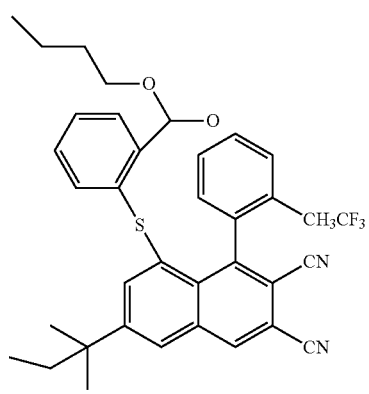
(4)-26
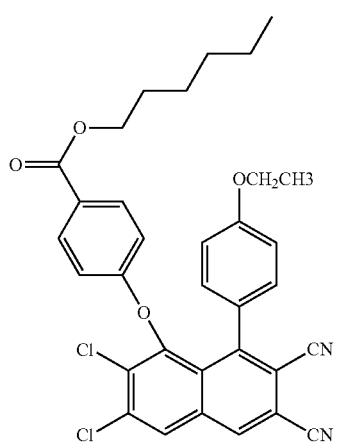 [SMILES: CCCCCCOC(=O)c1ccc(Oc2c(Cl)c(Cl)cc3cc(C#N)c(C#N)c(-c4ccc(OCC)cc4)c23)cc1]

TABLE 2-continued
(4)-27
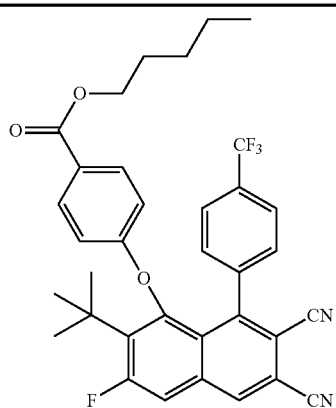
(4)-28
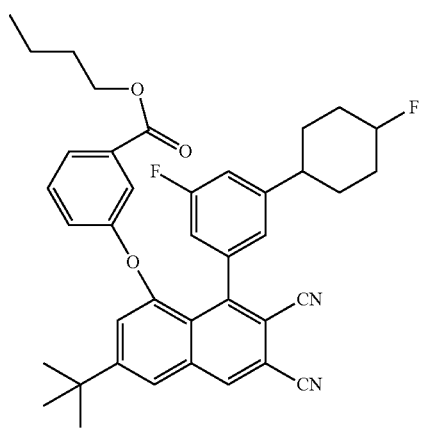 [SMILES: CCCCOC(=O)c1cccc(Oc2cc(C(C)(C)C)cc3cc(C#N)c(C#N)c(-c4cc(F)cc(C5CCC(F)CC5)c4)c23)c1]
(4)-29
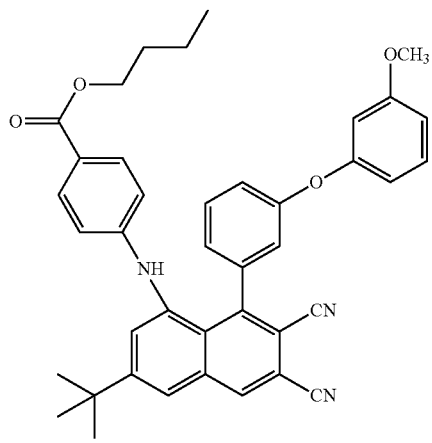 [SMILES: CCCCOC(=O)c1ccc(Nc2cc(C(C)(C)C)cc3cc(C#N)c(C#N)c(-c4cccc(Oc5cccc(OC)c5)c4)c23)cc1]
(4)-30
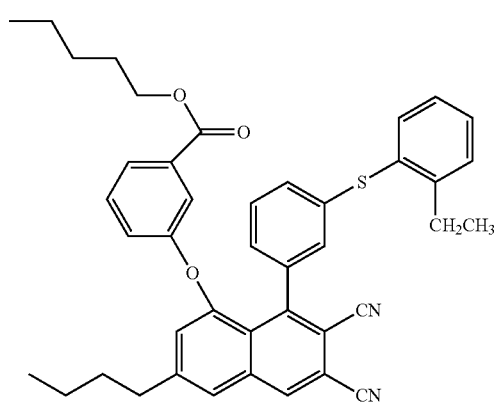 [SMILES: CCCCCOC(=O)c1cccc(Oc2cc(CCCC)cc3cc(C#N)c(C#N)c(-c4cccc(Sc5ccccc5CC)c4)c23)c1]

TABLE 2-continued
(4)-31
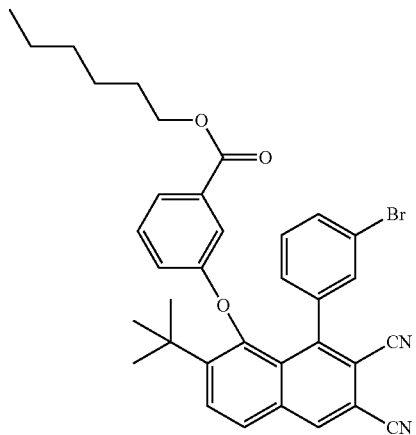 [SMILES: CCCCCCOC(=O)c1cccc(Oc2c(C(C)(C)C)ccc3cc(C#N)c(C#N)c(-c4cccc(Br)c4)c23)c1]
(4)-32
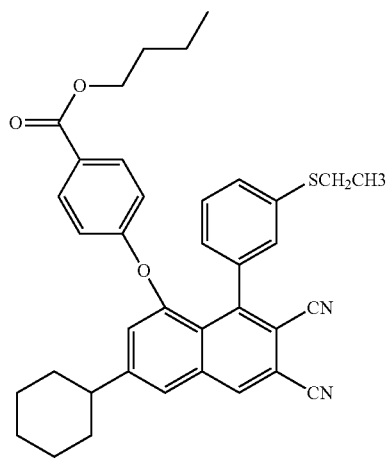
(4)-33
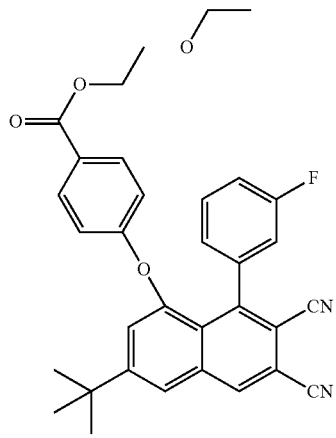

TABLE 2-continued
(4)-34
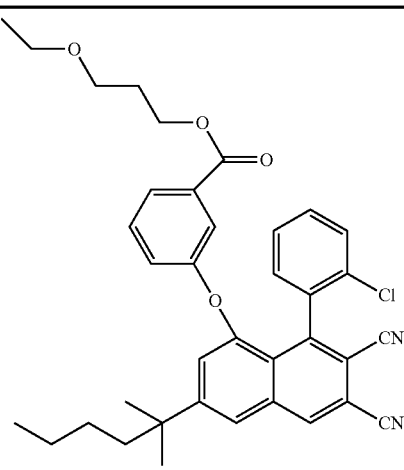
(4)-35
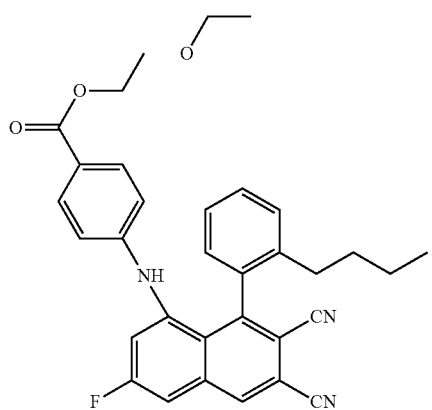
(4)-36
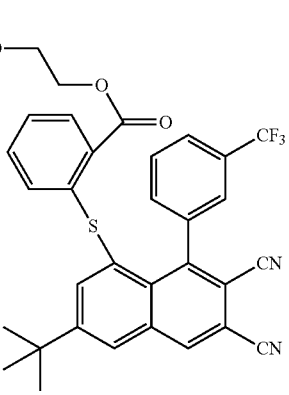
(4)-37
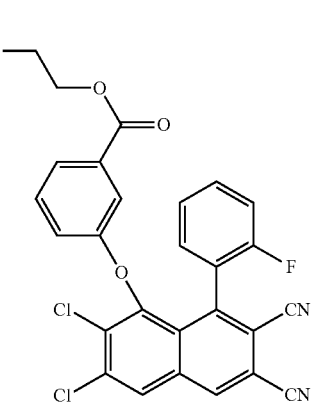

TABLE 2-continued
(4)-38
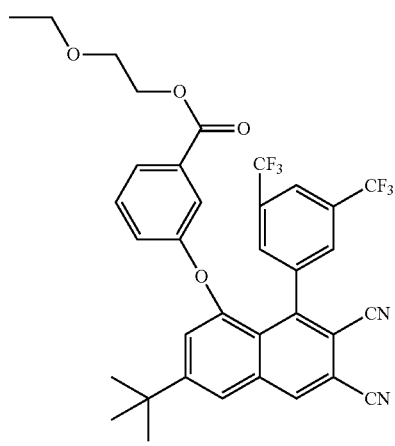 [SMILES: CCOCCOC(=O)c1cccc(Oc2cc(C(C)(C)C)cc3cc(C#N)c(C#N)c(-c4cc(C(F)(F)F)cc(C(F)(F)F)c4)c23)c1]
(4)-39
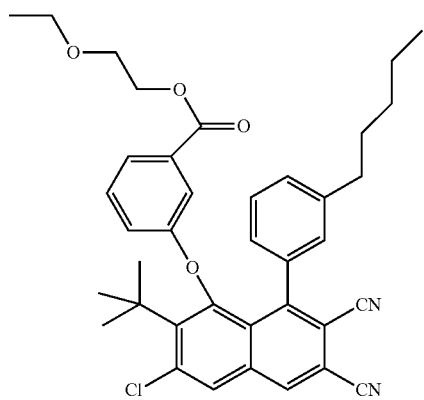 [SMILES: CCCCCc1cccc(-c2c(C#N)c(C#N)cc3cc(Cl)c(C(C)(C)C)c(Oc4cccc(C(=O)OCCOCC)c4)c23)c1]
(4)-40
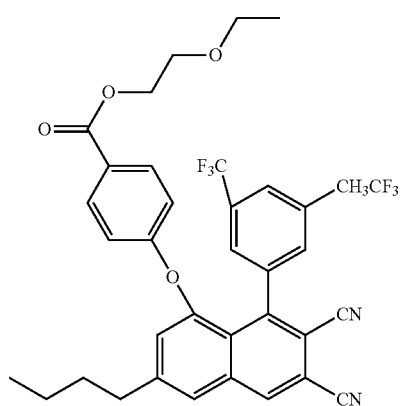

TABLE 2-continued
(4)-41
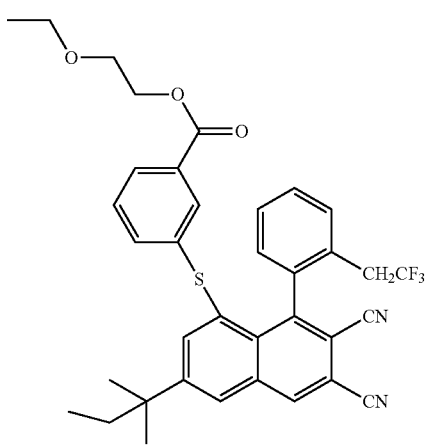
(4)-42
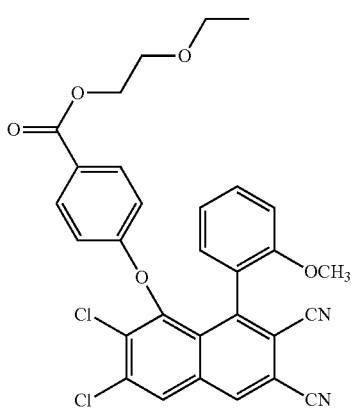 [SMILES: CCOCCOC(=O)c1ccc(Oc2c(Cl)c(Cl)cc3cc(C#N)c(C#N)c(-c4ccccc4OC)c23)cc1]
(4)-43
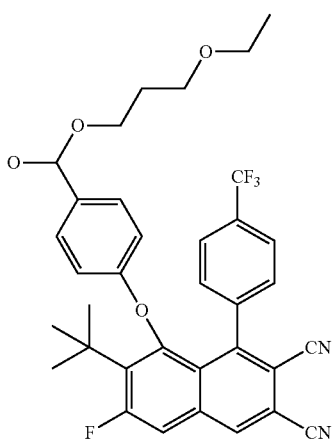 [SMILES: CCOCCCOC(O)c1ccc(Oc2c(C(C)(C)C)c(F)cc3cc(C#N)c(C#N)c(-c4ccc(C(F)(F)F)cc4)c23)cc1]

TABLE 2-continued
(4)-44
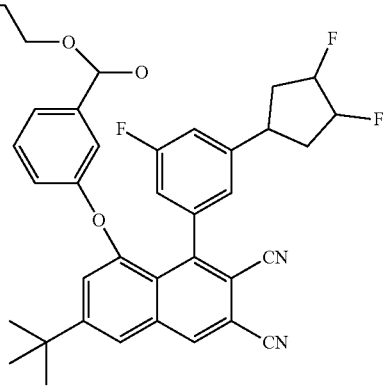
(4)-45
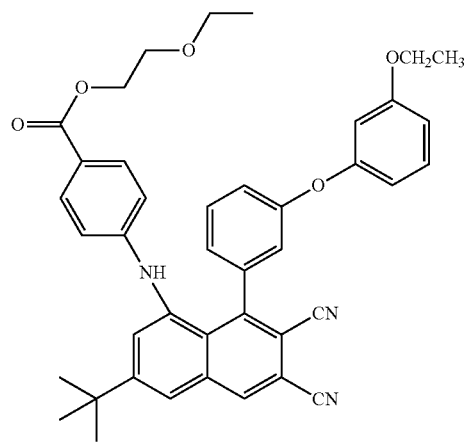 [SMILES: CCOCCOC(=O)c1ccc(Nc2cc(C(C)(C)C)cc3cc(C#N)c(C#N)c(-c4cccc(Oc5cccc(OCC)c5)c4)c23)cc1]
(4)-46
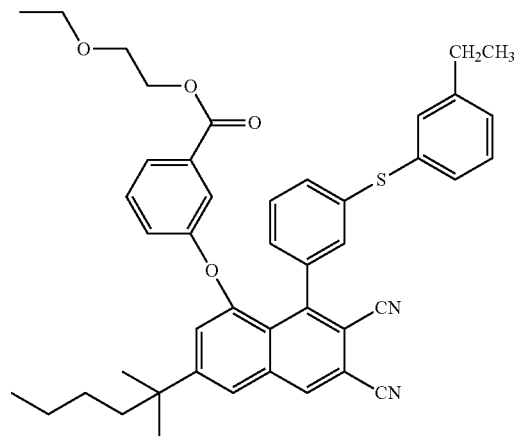 [SMILES: CCCCC(C)(C)c1cc(Oc2cccc(C(=O)OCCOCC)c2)c2c(-c3cccc(Sc4cccc(CC)c4)c3)c(C#N)c(C#N)cc2c1]

TABLE 2-continued
(4)-47
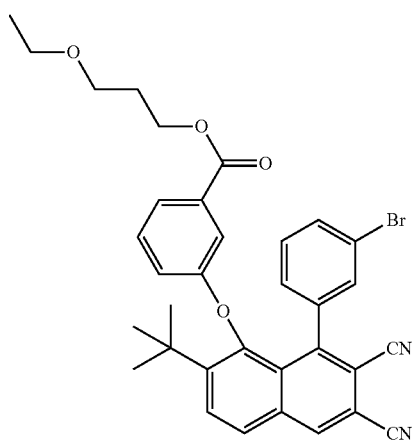
(4)-48
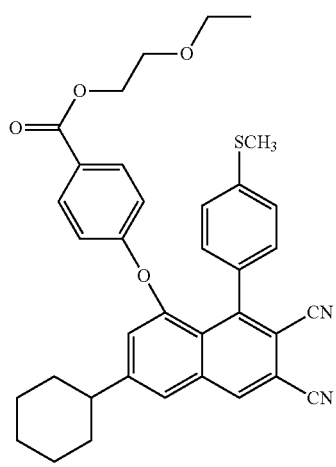 [SMILES: CCOCCOC(=O)c1ccc(Oc2cc(C3CCCCC3)cc3cc(C#N)c(C#N)c(-c4ccc(SC)cc4)c23)cc1]
(4)-49
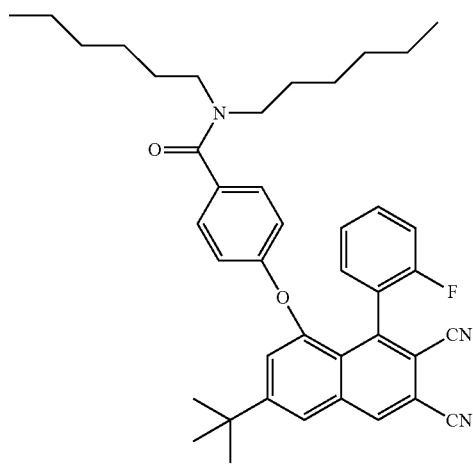 [SMILES: CCCCCCN(CCCCCC)C(=O)c1ccc(Oc2cc(C(C)(C)C)cc3cc(C#N)c(C#N)c(-c4ccccc4F)c23)cc1]

TABLE 2-continued
(4)-50
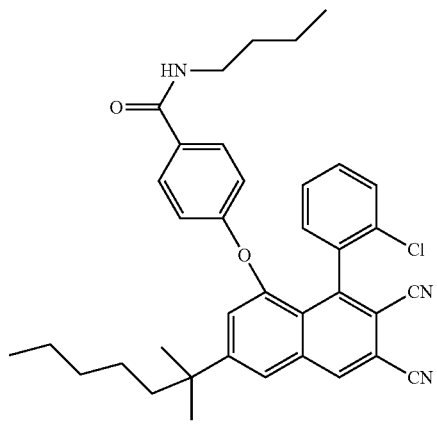 [SMILES: CCCCCC(C)(C)c1cc(Oc2ccc(C(=O)NCCCC)cc2)c2c(-c3ccccc3Cl)c(C#N)c(C#N)cc2c1]
(4)-51
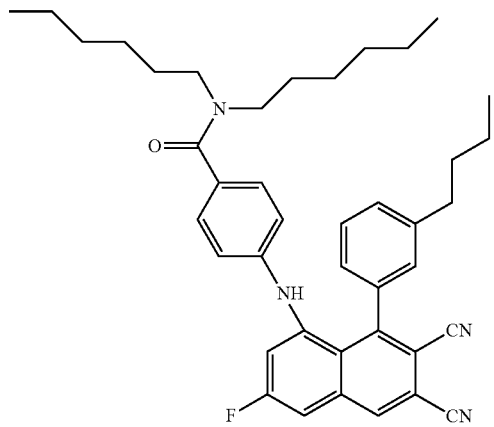 [SMILES: CCCCCCN(CCCCCC)C(=O)c1ccc(Nc2cc(F)cc3cc(C#N)c(C#N)c(-c4cccc(CCCC)c4)c23)cc1]
(4)-52
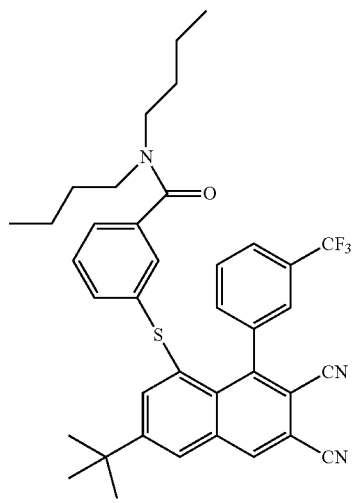 [SMILES: CCCCN(CCCC)C(=O)c1cccc(Sc2cc(C(C)(C)C)cc3cc(C#N)c(C#N)c(-c4cccc(C(F)(F)F)c4)c23)c1]

TABLE 2-continued
(4)-53
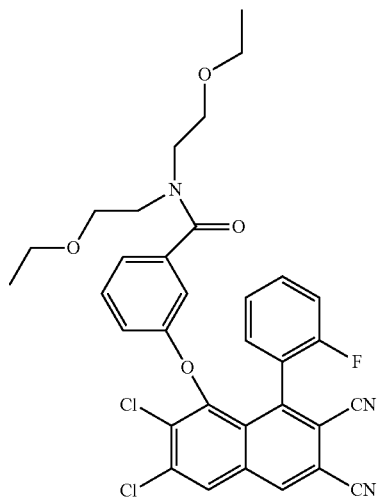 [SMILES: CCOCCN(CCOCC)C(=O)c1cccc(Oc2c(Cl)c(Cl)cc3cc(C#N)c(C#N)c(-c4ccccc4F)c23)c1]
(4)-54
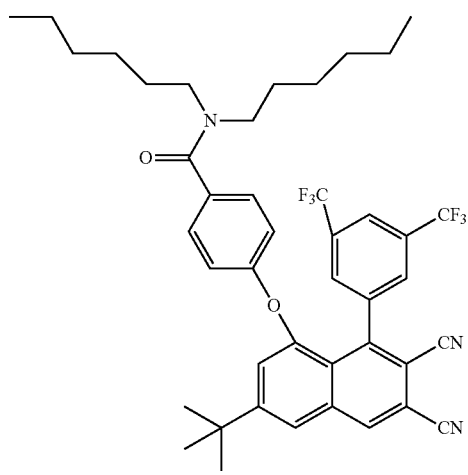 [SMILES: CCCCCCN(CCCCCC)C(=O)c1ccc(Oc2cc(C(C)(C)C)cc3cc(C#N)c(C#N)c(-c4cc(C(F)(F)F)cc(C(F)(F)F)c4)c23)cc1]
(4)-55
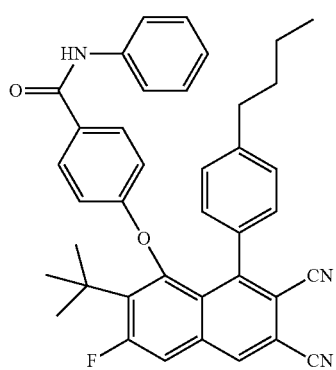 [SMILES: CCCCc1ccc(-c2c(C#N)c(C#N)cc3cc(F)c(C(C)(C)C)c(Oc4ccc(C(=O)Nc5ccccc5)cc4)c23)cc1]

TABLE 2-continued
(4)-56
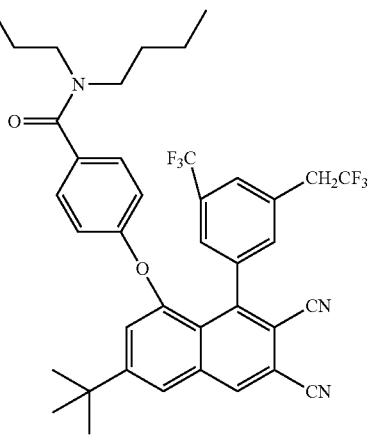
(4)-57
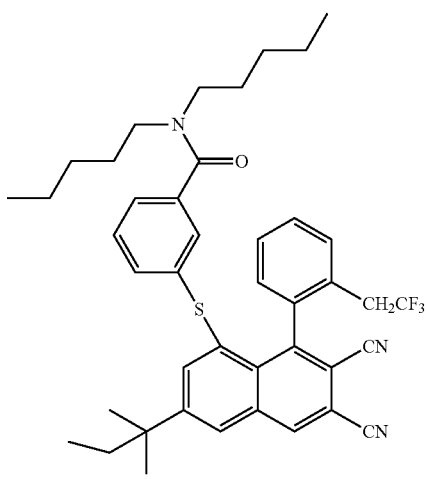
(4)-58
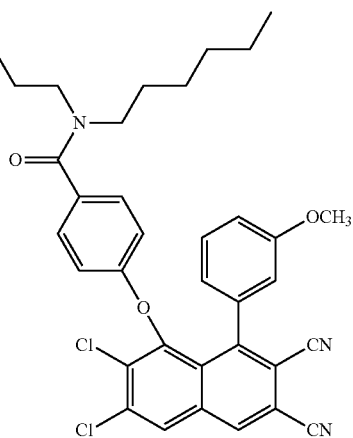

TABLE 2-continued
(4)-59
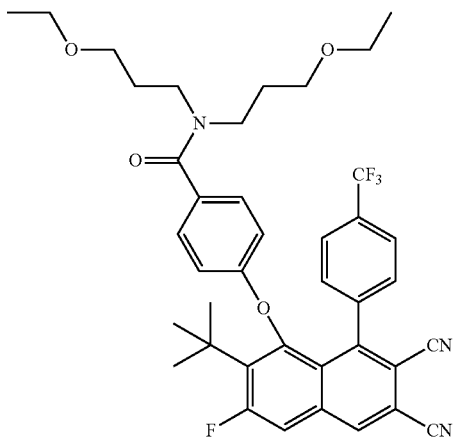 [SMILES: CCOCCCN(CCCOCC)C(=O)c1ccc(Oc2c(C(C)(C)C)c(F)cc3cc(C#N)c(C#N)c(-c4ccc(C(F)(F)F)cc4)c23)cc1]
(4)-60
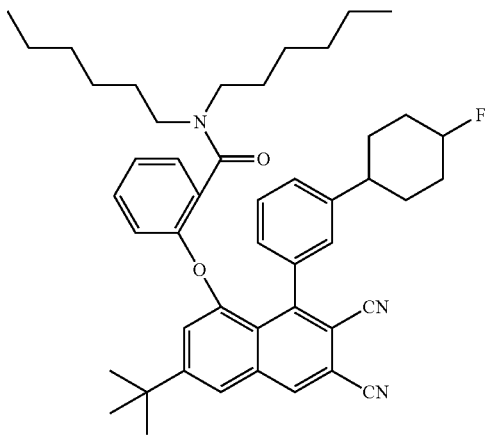 [SMILES: CCCCCCN(CCCCCC)C(=O)c1ccccc1Oc1cc(C(C)(C)C)cc2cc(C#N)c(C#N)c(-c3cccc(C4CCC(F)CC4)c3)c12]
(4)-61
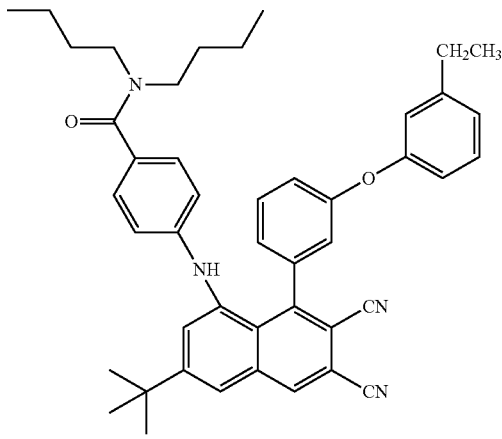 [SMILES: CCCCN(CCCC)C(=O)c1ccc(Nc2cc(C(C)(C)C)cc3cc(C#N)c(C#N)c(-c4cccc(Oc5cccc(CC)c5)c4)c23)cc1]

TABLE 2-continued
(4)-62
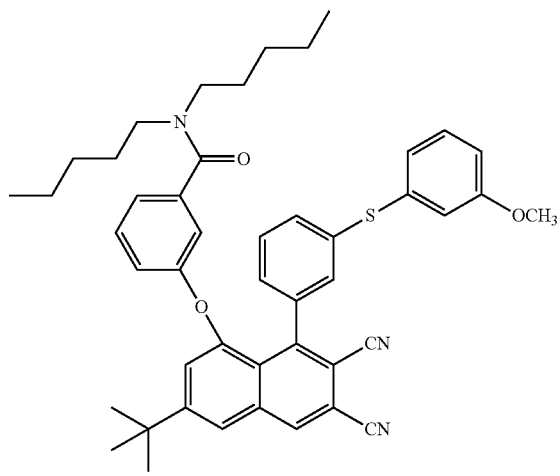 [SMILES: CCCCCN(CCCCC)C(=O)c1cccc(Oc2cc(C(C)(C)C)cc3cc(C#N)c(C#N)c(-c4cccc(Sc5cccc(OC)c5)c4)c23)c1]
(4)-63
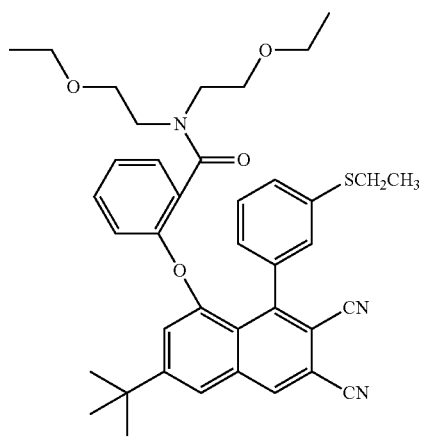
(4)-64
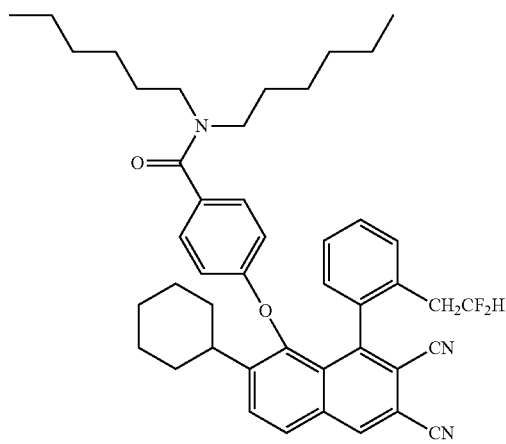

TABLE 2-continued
(4)-65
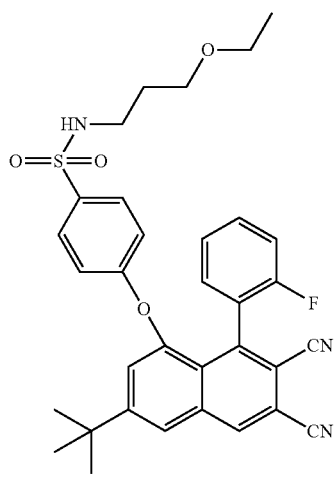 [SMILES: CCOCCCNS(=O)(=O)c1ccc(Oc2cc(C(C)(C)C)cc3cc(C#N)c(C#N)c(-c4ccccc4F)c23)cc1]
(4)-66
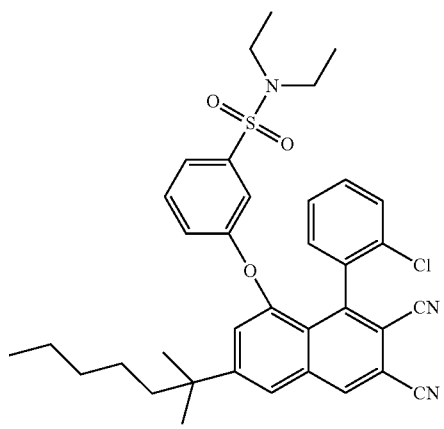 [SMILES: CCCCCC(C)(C)c1cc(Oc2cccc(S(=O)(=O)N(CC)CC)c2)c2c(-c3ccccc3Cl)c(C#N)c(C#N)cc2c1]
(4)-67
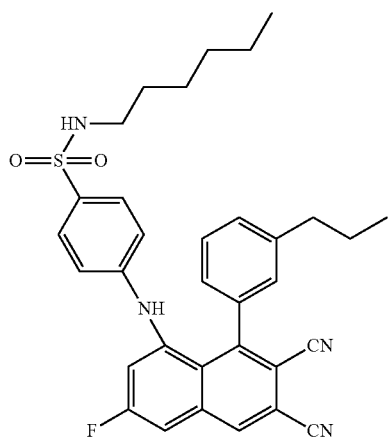 [SMILES: CCCCCCNS(=O)(=O)c1ccc(Nc2cc(F)cc3cc(C#N)c(C#N)c(-c4cccc(CCC)c4)c23)cc1]

TABLE 2-continued
(4)-68 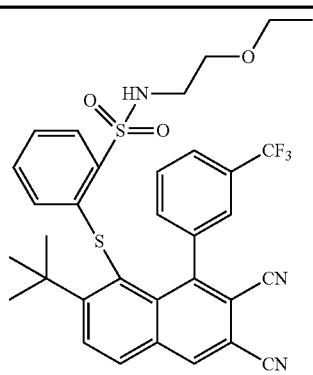
(4)-69 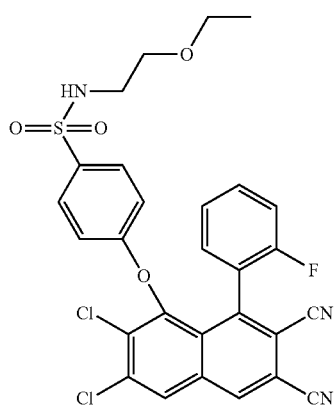 [SMILES: CCOCCNS(=O)(=O)c1ccc(Oc2c(Cl)c(Cl)cc3cc(C#N)c(C#N)c(-c4ccccc4F)c23)cc1]
(4)-70 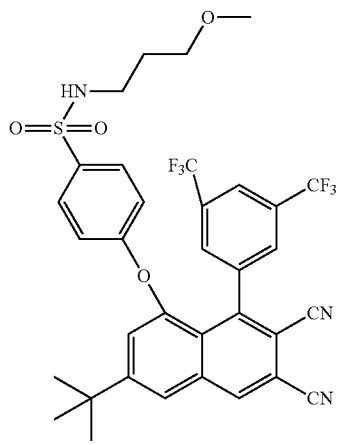 [SMILES: COCCCNS(=O)(=O)c1ccc(Oc2cc(C(C)(C)C)cc3cc(C#N)c(C#N)c(-c4cc(C(F)(F)F)cc(C(F)(F)F)c4)c23)cc1]
(4)-71 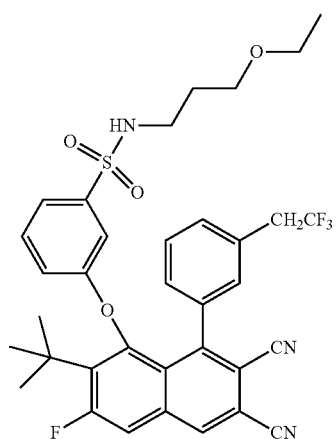

TABLE 2-continued
(4)-72
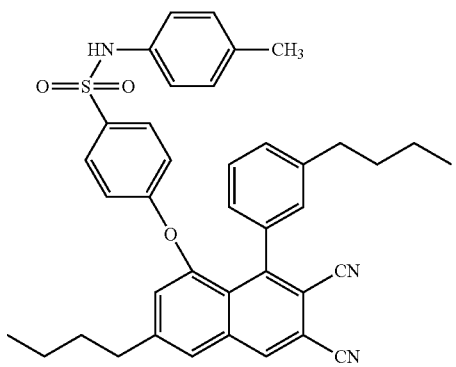 [SMILES: CCCCc1cccc(-c2c(C#N)c(C#N)cc3cc(CCCC)cc(Oc4ccc(S(=O)(=O)Nc5ccc(C)cc5)cc4)c23)c1]
(4)-73
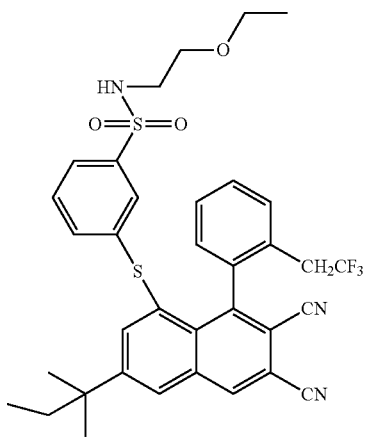
(4)-74
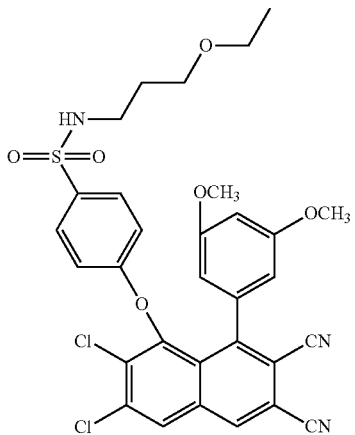 [SMILES: CCOCCCNS(=O)(=O)c1ccc(Oc2c(Cl)c(Cl)cc3cc(C#N)c(C#N)c(-c4cc(OC)cc(OC)c4)c23)cc1]

TABLE 2-continued
(4)-75
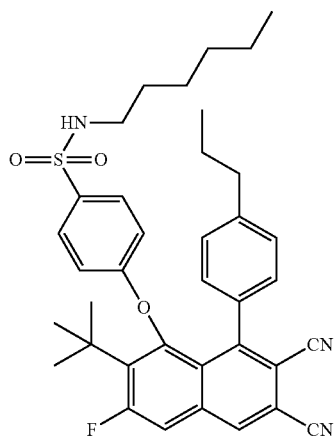 [SMILES: CCCCCCNS(=O)(=O)c1ccc(Oc2c(C(C)(C)C)c(F)cc3cc(C#N)c(C#N)c(-c4ccc(CCC)cc4)c23)cc1]
(4)-76
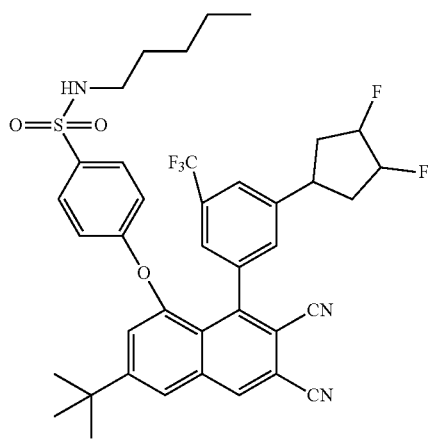 [SMILES: CCCCCNS(=O)(=O)c1ccc(Oc2cc(C(C)(C)C)cc3cc(C#N)c(C#N)c(-c4cc(C5CC(F)C(F)C5)cc(C(F)(F)F)c4)c23)cc1]
(4)-77
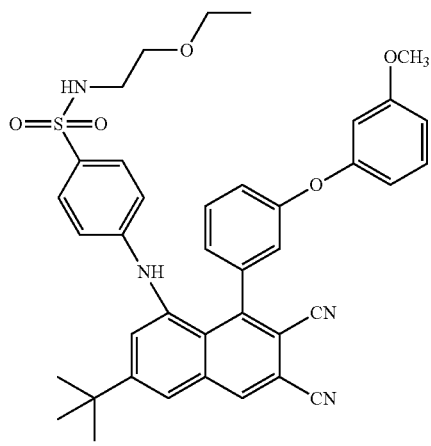 [SMILES: CCOCCNS(=O)(=O)c1ccc(Nc2cc(C(C)(C)C)cc3cc(C#N)c(C#N)c(-c4cccc(Oc5cccc(OC)c5)c4)c23)cc1]

TABLE 2-continued
(4)-78
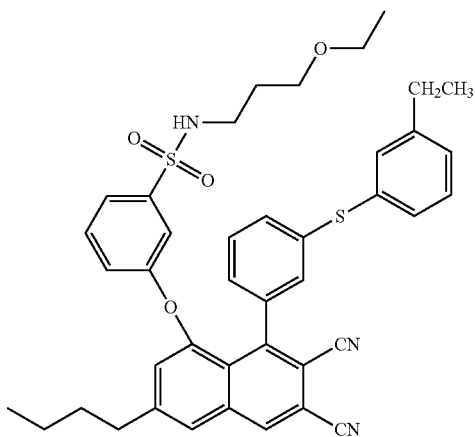 [SMILES: CCCCc1cc(Oc2cccc(S(=O)(=O)NCCCOCC)c2)c2c(-c3cccc(Sc4cccc(CC)c4)c3)c(C#N)c(C#N)cc2c1]
(4)-79
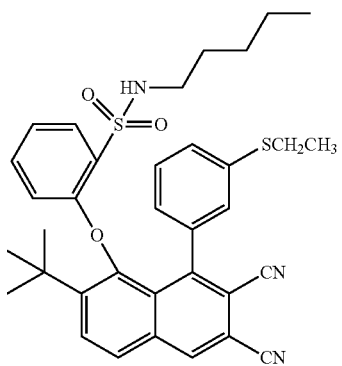
(4)-80
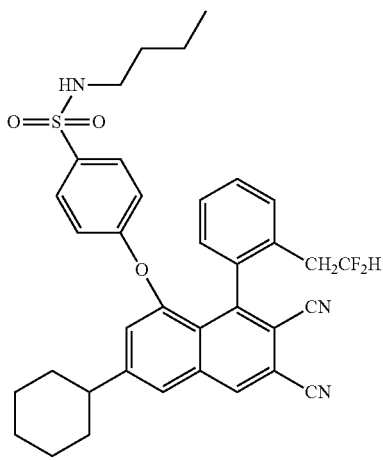

The naphthalene-2,3-dicarbonitrile compound represented by General Formula (4) can be produced with reference to known processes relating to known compounds.

For example, the naphthalene-2,3-dicarbonitrile compound can be produced according to the following route by using a 2-methylbenzophenone compound represented by General Formula (6) with reference to Russian Journal of General Chemistry, Vol 75, No. 5, 2005, pp. 795-799.

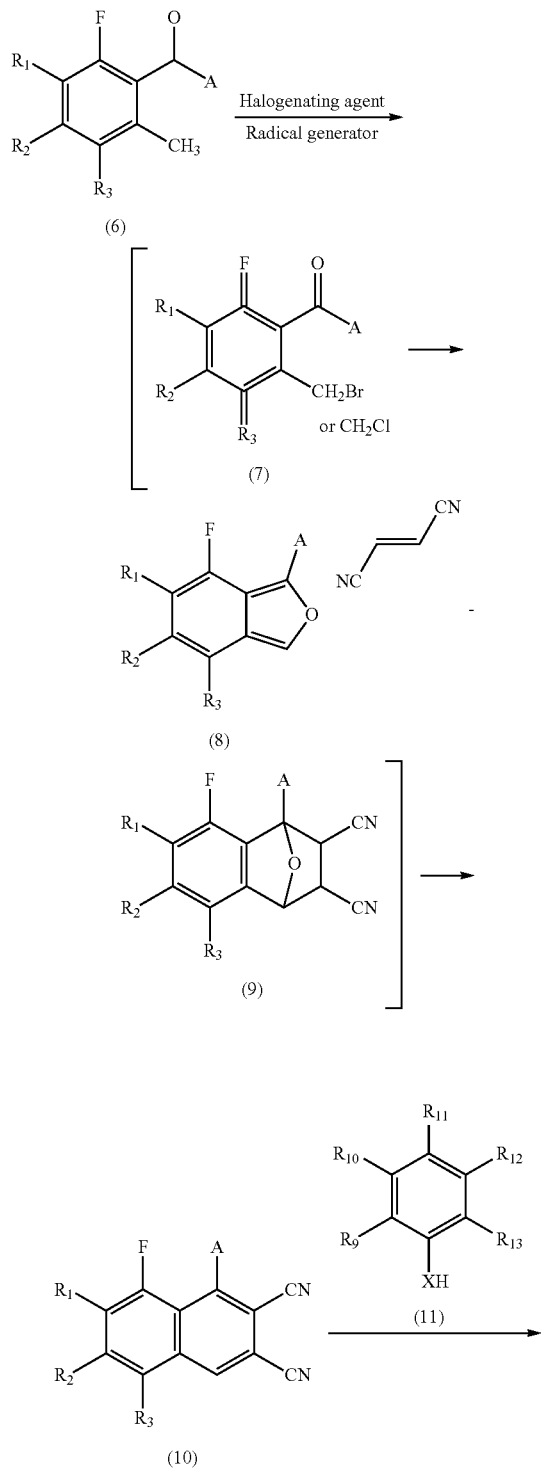

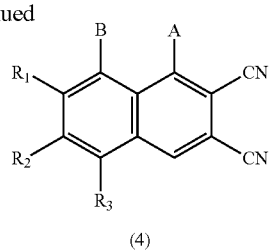

In General Formulae (6) to (11), A, $R_1$ to $R_3$, $R_9$ to $R_{13}$, and X have the same definition as A, $R_1$ to $R_3$, $R_9$ to $R_{13}$ and X in General Formula (4).

Specifically, in a case where the compound represented by General Formula (6) reacts with a halogenating agent in an organic solvent in the presence of a radical generator, the compound represented by General Formula (7) is obtained. Then, a condensation reaction is performed to obtain the compound represented by General Formula (8), and then a Diels-Alder reaction is caused between the compound represented by General Formula (8) and fumaronitrile, thereby obtaining the compound represented by General Formula (9). By performing a dehydration reaction on the compound represented by General Formula (9) in the presence of an acid catalyst, the compound represented by General Formula (10) can be produced. Furthermore, by causing a reaction between the compound represented by General Formula (10) and the compound represented by General Formula (11) in the presence of a base in an organic solvent, the compound represented by General Formula (4) is obtained.

In this producing process, some of the compounds represented by General Formulae (7) and (8) are unstable. Therefore, in view of yield and operability, it is preferable to produce the compound by a one-pot process from General Formula (6) to General Formula (10) without isolating an intermediate. In addition, by causing a reaction between General Formula (10) and General Formula (11) in the presence of a base in an organic solvent, General Formula (4) can be obtained.

Examples of the radical generator used in the halogenation process from General Formula (6) to General Formula (7) include a peroxide-based radical generator such as benzoyl peroxide, di-tert-butyl peroxide, or tert-butyl hydroperoxide, an azo polymerization initiator such as V-70, V-65, AIBN, V-59, V-501, V-40, V-30, V-501, VA-044, VA-046B, VA-061, V-50, VA-057, VA-086, VF-096, VAm-110, or V-601, and the like.

The molar quantity of the radical generator is 0.01 to 3 times, preferably 0.02 to 2 times, and more preferably 0.02 to 1 time with respect to 1 mol of General Formula (6).

Examples of the halogenating agent include bromine, chlorine, N-bromosuccinimide, N-chlorosuccinimide, and the like.

The molar quantity of the halogenating agent used is 1 to 10 times, preferably 1 to 5 times, and more preferably 1 to 3 times with respect to 1 mol of General Formula (6).

The reaction solvent is not particularly limited unless it negatively affects the reaction. Examples thereof include an aromatic hydrocarbon such as toluene, xylene, mesitylene, pseudocumene, chlorobenzene, or dichlorobenzene, an aliphatic hydrocarbon such as hexane, heptane, cyclohexane, carbon tetrachloride, or chloroform, organic acids such as acetic acid and trifluoroacetic acid, and an aprotic solvent such as DMF, DMAC, or DMI.

The volume of the solvent is 1 to 100 times, preferably 1 to 50 times, and more preferably 3 to 20 times with respect to volume of the compound represented by General Formula (6).

The reaction temperature is room temperature to 200° C., preferably 50° C. to 150° C., and more preferably 50° C. to 100° C.

The reaction time is 30 minutes to 48 hours, preferably 1 to 24 hours, and more preferably 1 to 12 hours.

In the process from General Formula (7) to General Formula (8), the reaction temperature is room temperature to 250° C., preferably 50° C. to 200° C., and more preferably 50° C. to 150° C.

The reaction time is 30 minutes to 48 hours, preferably 1 to 24 hours, and more preferably 1 to 12 hours.

In the process from General Formula (8) to General Formula (9), the molar quantity of fumaronitrile is 1 to 5 times, preferably 1 to 2 times, and more preferably 1 to 1.5 times with respect to 1 mol of General Formula (4).

Examples of the acid catalyst include concentrated sulfuric acid, p-toluenesulfonic acid monohydrate, and the like.

The weight of the acid catalyst is 0.1 to 10 times, preferably 0.2 to 5 times, and more preferably 0.5 to 3 times with respect to the weight of General Formula (6).

After the reaction from General Formula (6) to General Formula (10) ends, General Formula (10) can be obtained by being separated from the reaction system by general means. If necessary, by further performing a known purification operation such as recrystallization or column chromatography, General Formula (10) can be purified.

In the process from General Formula (10) to General Formula (4), the molar quantity of General Formula (11) is 1 to 2 times, preferably 1 to 1.5 times, and more preferably 1 to 1.2 times respect to 1 mol of General Formula (10).

The reaction solvent is not particularly limited unless it negatively affects the reaction. It is preferable to use an aprotic solvent such as DMF, DMAC, or DMI.

The volume of the solvent is 1 to 50 times, preferably 2 to 20 times, and more preferably 3 to 10 times with respect to General Formula (10).

As the base, an alkaline substance such as potassium fluoride, potassium carbonate, potassium hydroxide, or sodium hydroxide is preferable, and potassium carbonate is more preferable.

The molar quantity of the base is 0.5 to 20 times, preferably 1 to 10 times, and more preferably 2 to 5 times with respect to 1 mol of General Formula (10).

The reaction temperature is room temperature to 200° C., preferably 50° C. to 150° C., and more preferably 50° C. to 100° C.

The reaction time is 30 minutes to 48 hours, preferably 1 to 24 hours, and more preferably 1 to 12 hours.

After the above reaction ends, General Formula (4) can be obtained by being separated from the reaction system by general means. If necessary, by further performing a known purification operation such as recrystallization or column chromatography, General Formula (4) can be purified.

1,3-diiminobenzisoindoline Compound

A fourth invention of the present invention is a 1,3-diiminobenzisoindoline compound represented by General Formula (5).

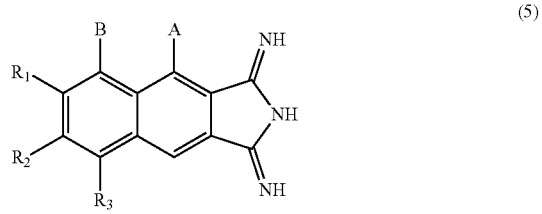

(5)

In Formula (5), $R_1$ to $R_3$, A, and B have the same definition as $R_1$ to $R_3$, A, and B in General Formula (1).

The 1,3-diiminobenzisoindoline compound represented by General Formula (5) is an intermediate used for producing the naphthalocyanine compound represented by any of General Formula (1) and General Formulae (1)-a to (1)-d.

In General Formula (5), preferred ranges and specific examples of $R_4$ to $R_8$ as substituents of A, $R_9$ to $R_{13}$ as substituents of B, and $R_1$ to $R_3$ are the same as the preferred ranges and specific examples of $R_4$ to $R_8$, $R_9$ to $R_{13}$, and $R_1$ to $R_3$ shown in General Formula (1) and General Formulae (1)-a to (1)-d.

Specific examples of the 1,3-diiminobenzisoindoline compound represented by General Formula (5) will be shown in the following Table 3, but the present invention is not limited thereto.

TABLE 3

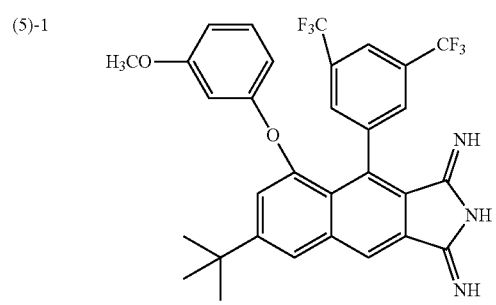

(5)-1

TABLE 3-continued
(5)-2
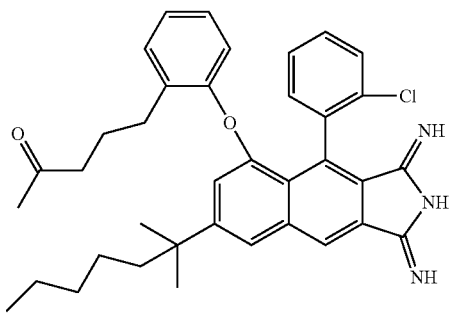 [SMILES: CCCCCC(C)(C)c1cc(Oc2ccccc2CCCC(C)=O)c2c(-c3ccccc3Cl)c3c(cc2c1)C(=N)NC3=N]
(5)-3
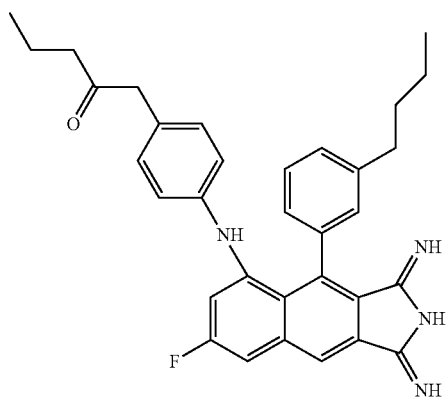 [SMILES: CCCCc1cccc(-c2c3c(cc4cc(F)cc(Nc5ccc(CC(=O)CCC)cc5)c24)C(=N)NC3=N)c1]
(5)-4
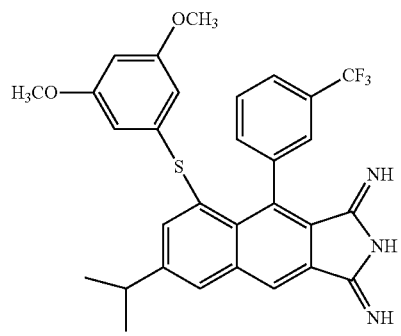 [SMILES: COc1cc(OC)cc(Sc2cc(C(C)C)cc3cc4c(c(-c5cccc(C(F)(F)F)c5)c23)C(=N)NC4=N)c1]
(5)-5
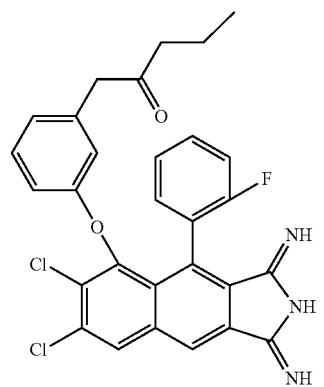 [SMILES: CCCC(=O)Cc1cccc(Oc2c(Cl)c(Cl)cc3cc4c(c(-c5ccccc5F)c23)C(=N)NC4=N)c1]

TABLE 3-continued
(5)-6 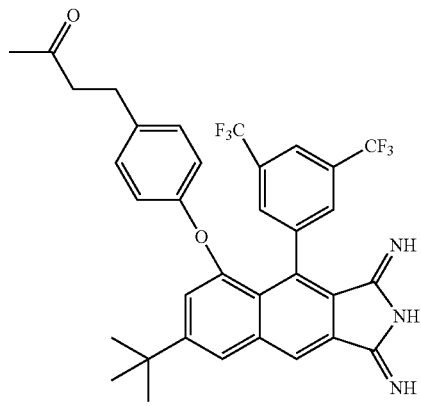 [SMILES: CC(=O)CCc1ccc(Oc2cc(C(C)(C)C)cc3cc4c(c(-c5cc(C(F)(F)F)cc(C(F)(F)F)c5)c23)C(=N)NC4=N)cc1]
(5)-7 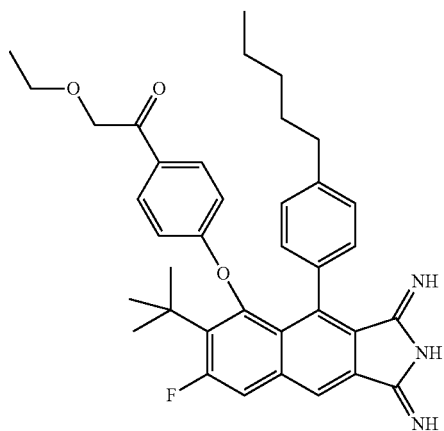 [SMILES: CCCCCc1ccc(-c2c3c(cc4cc(F)c(C(C)(C)C)c(Oc5ccc(C(=O)COCC)cc5)c24)C(=N)NC3=N)cc1]
(5)-8 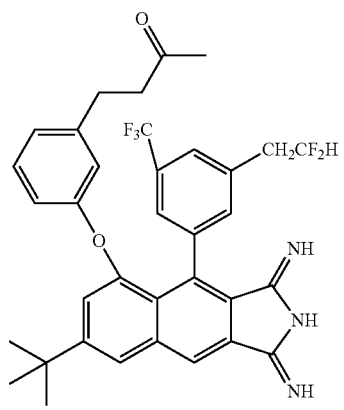
(5)-9 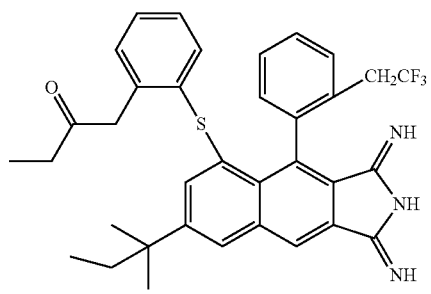

TABLE 3-continued
(5)-10
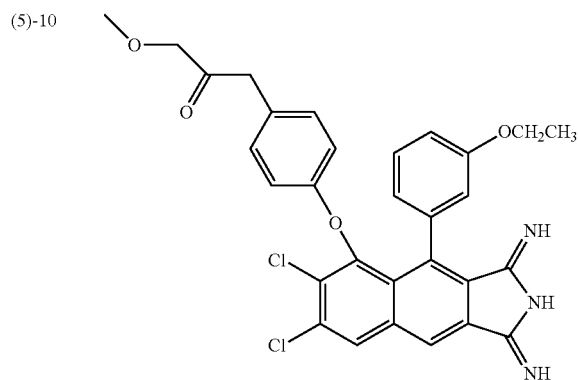
(5)-11
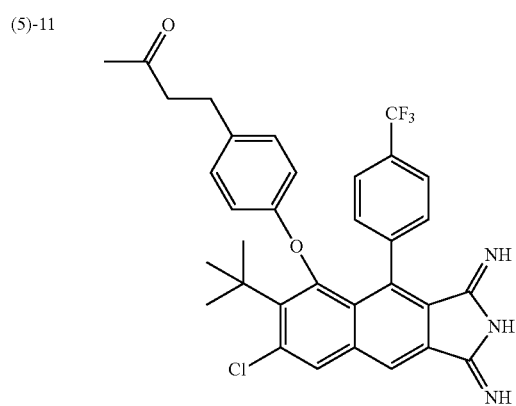
(5)-12
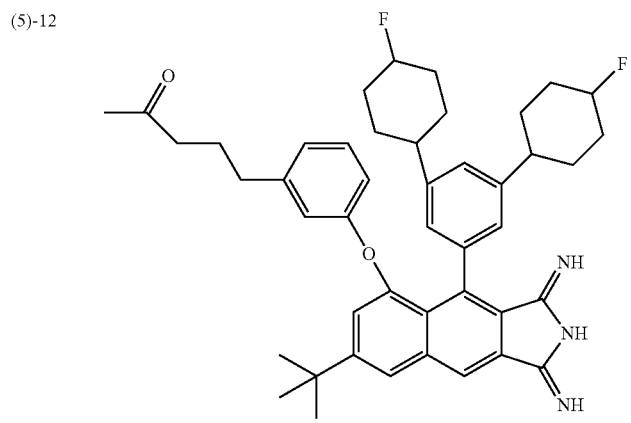
(5)-13
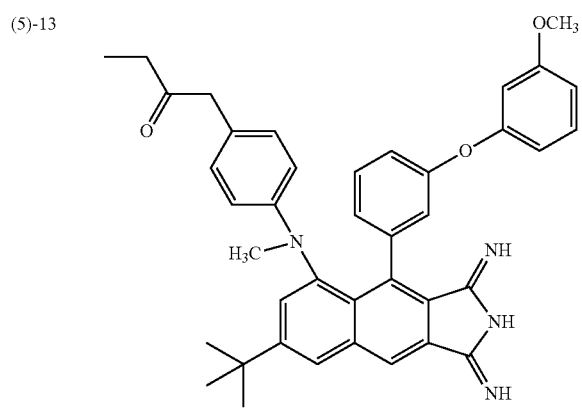

TABLE 3-continued
(5)-14
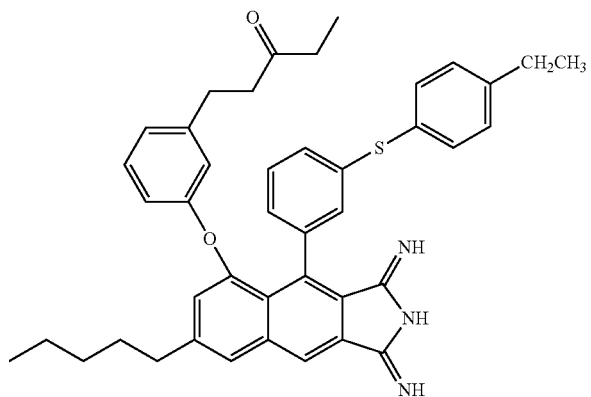 [SMILES: CCCCCc1cc(Oc2cccc(CCC(=O)CC)c2)c2c(-c3cccc(Sc4ccc(CC)cc4)c3)c3c(cc2c1)C(=N)NC3=N]
(5)-15
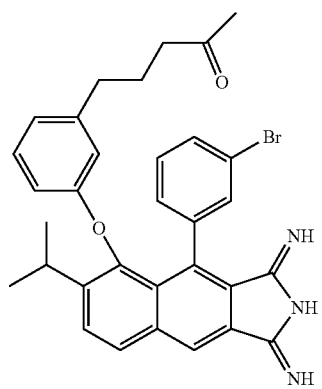 [SMILES: CC(=O)CCCc1cccc(Oc2c(C(C)C)ccc3cc4c(c(-c5cccc(Br)c5)c23)C(=N)NC4=N)c1]
(5)-16
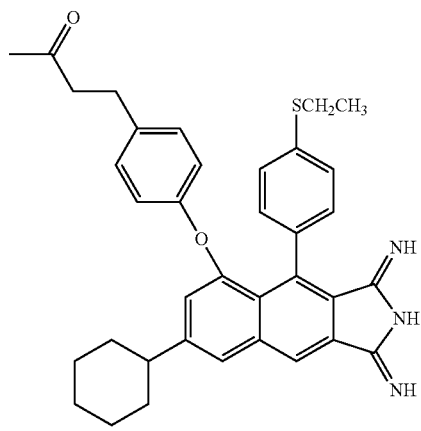

TABLE 3-continued
(5)-17
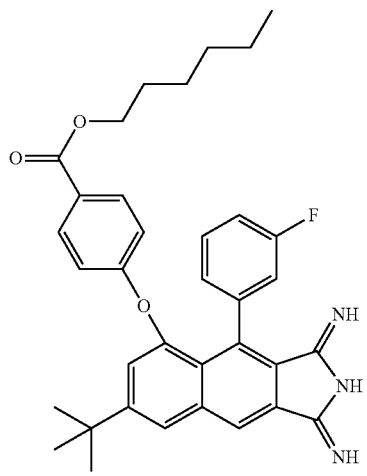 [SMILES: CCCCCCOC(=O)c1ccc(Oc2cc(C(C)(C)C)cc3cc4c(c(-c5cccc(F)c5)c23)C(=N)NC4=N)cc1]
(5)-18
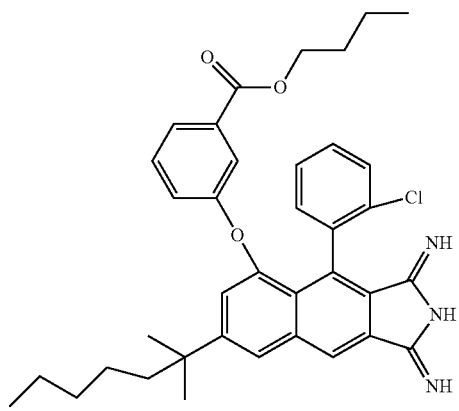 [SMILES: CCCCCC(C)(C)c1cc(Oc2cccc(C(=O)OCCCC)c2)c2c(-c3ccccc3Cl)c3c(cc2c1)C(=N)NC3=N]
(5)-19
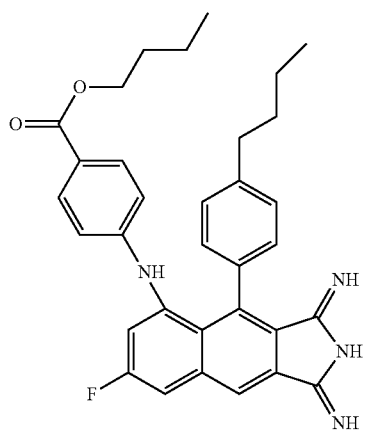 [SMILES: CCCCOC(=O)c1ccc(Nc2cc(F)cc3cc4c(c(-c5ccc(CCCC)cc5)c23)C(=N)NC4=N)cc1]

TABLE 3-continued
(5)-20
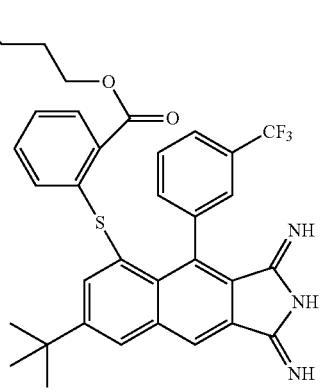
(5)-21
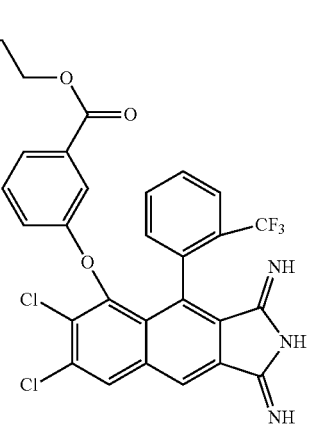
(5)-22
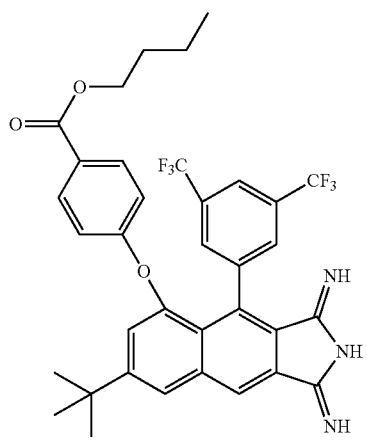 [SMILES: CCCCOC(=O)c1ccc(Oc2cc(C(C)(C)C)cc3cc4c(c(-c5cc(C(F)(F)F)cc(C(F)(F)F)c5)c23)C(=N)NC4=N)cc1]
(5)-23
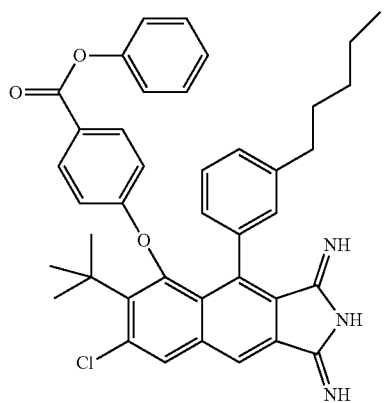 [SMILES: CCCCCc1cccc(-c2c3c(cc4cc(Cl)c(C(C)(C)C)c(Oc5ccc(C(=O)Oc6ccccc6)cc5)c24)C(=N)NC3=N)c1]

TABLE 3-continued
(5)-24
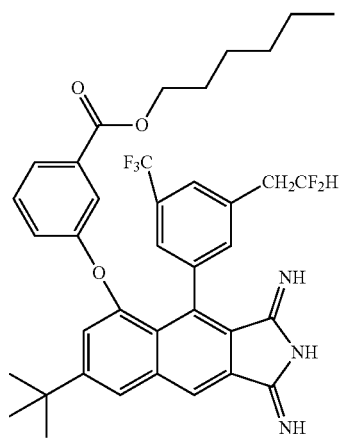
(5)-25
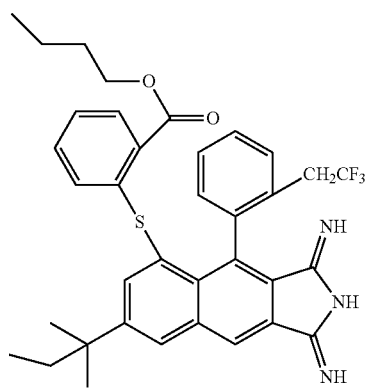
(5)-26
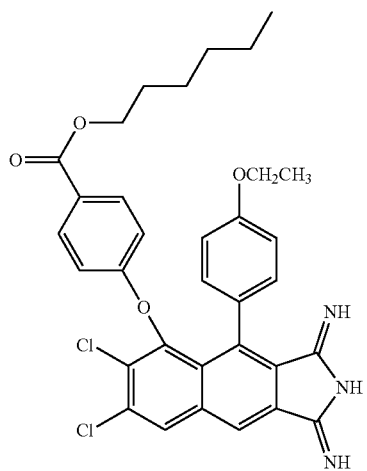 [SMILES: CCCCCCOC(=O)c1ccc(Oc2c(Cl)c(Cl)cc3cc4c(c(-c5ccc(OCC)cc5)c23)C(=N)NC4=N)cc1]

TABLE 3-continued
(5)-27
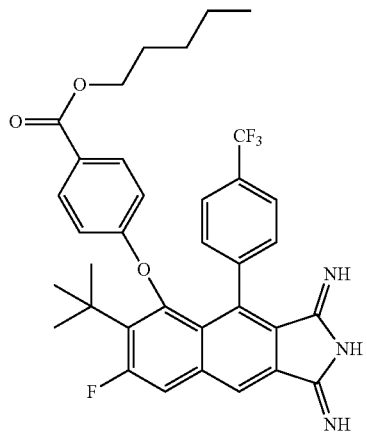 [SMILES: CCCCCOC(=O)c1ccc(Oc2c(C(C)(C)C)c(F)cc3cc4c(c(-c5ccc(C(F)(F)F)cc5)c23)C(=N)NC4=N)cc1]
(5)-28
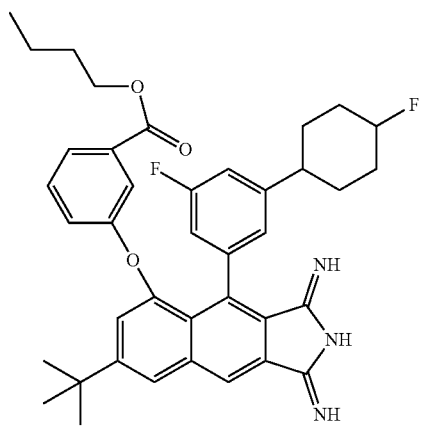 [SMILES: CCCCOC(=O)c1cccc(Oc2cc(C(C)(C)C)cc3cc4c(c(-c5cc(F)cc(C6CCC(F)CC6)c5)c23)C(=N)NC4=N)c1]
(5)-29
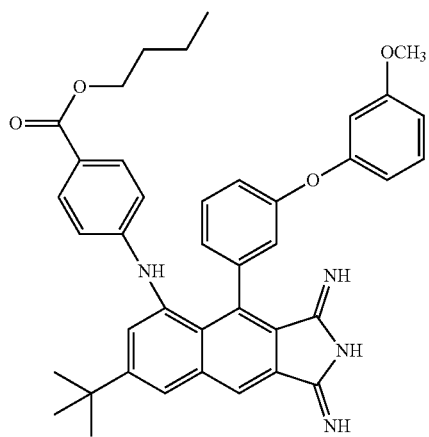 [SMILES: CCCCOC(=O)c1ccc(Nc2cc(C(C)(C)C)cc3cc4c(c(-c5cccc(Oc6cccc(OC)c6)c5)c23)C(=N)NC4=N)cc1]

TABLE 3-continued
(5)-30
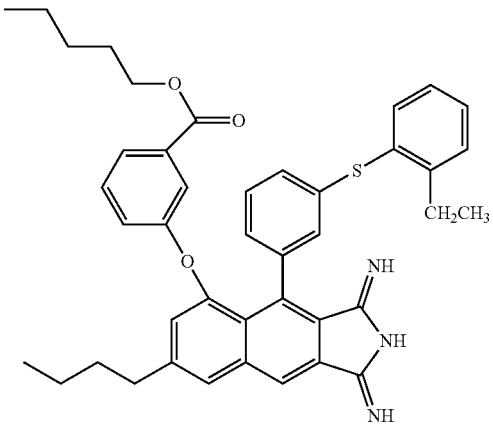 [SMILES: CCCCCOC(=O)c1cccc(Oc2cc(CCCC)cc3cc4c(c(-c5cccc(Sc6ccccc6CC)c5)c23)C(=N)NC4=N)c1]
(5)-31
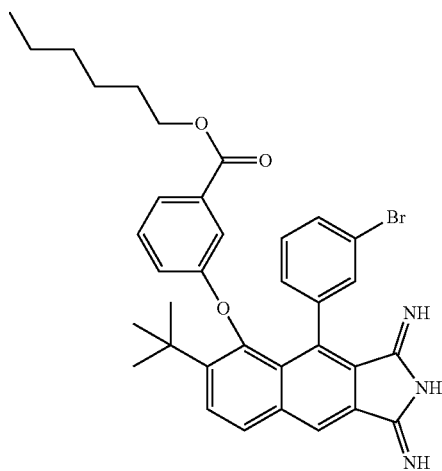 [SMILES: CCCCCCOC(=O)c1cccc(Oc2c(C(C)(C)C)ccc3cc4c(c(-c5cccc(Br)c5)c23)C(=N)NC4=N)c1]
(5)-32
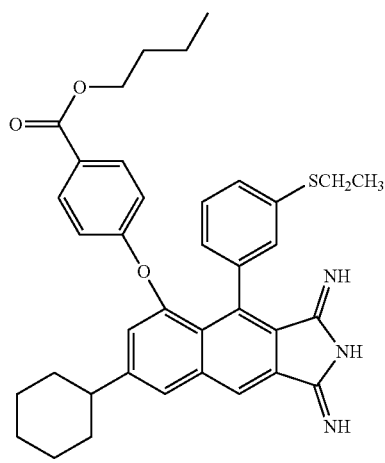

TABLE 3-continued
(5)-33
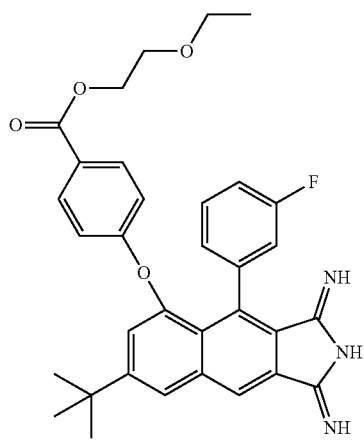 [SMILES: CCOCCOC(=O)c1ccc(Oc2cc(C(C)(C)C)cc3cc4c(c(-c5cccc(F)c5)c23)C(=N)NC4=N)cc1]
(5)-34
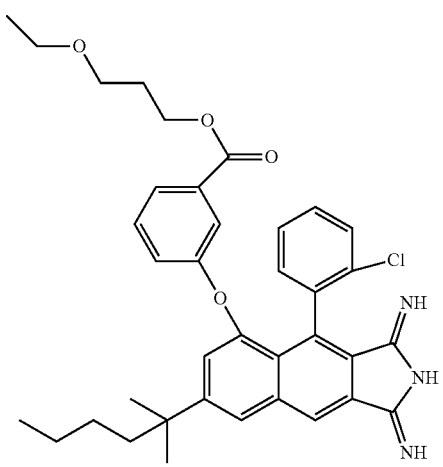 [SMILES: CCCCC(C)(C)c1cc(Oc2cccc(C(=O)OCCCOCC)c2)c2c(-c3ccccc3Cl)c3c(cc2c1)C(=N)NC3=N]
(5)-35
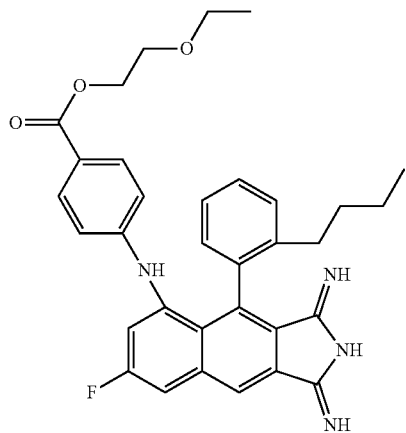 [SMILES: CCCCc1ccccc1-c1c2c(cc3cc(F)cc(Nc4ccc(C(=O)OCCOCC)cc4)c13)C(=N)NC2=N]

TABLE 3-continued
(5)-36
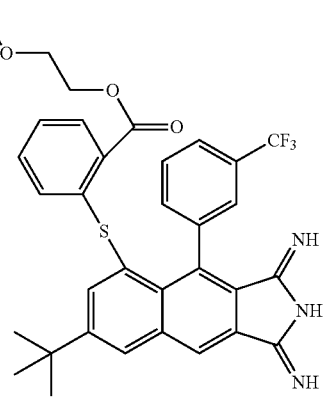
(5)-37
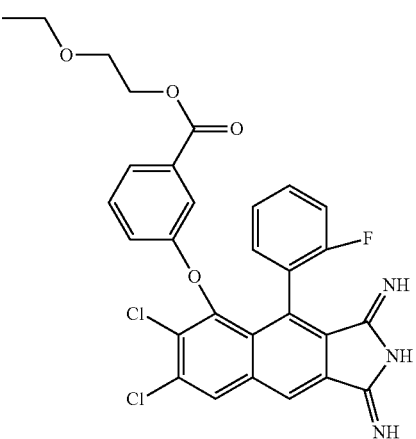 [SMILES: CCOCCOC(=O)c1cccc(Oc2c(Cl)c(Cl)cc3cc4c(c(-c5ccccc5F)c23)C(=N)NC4=N)c1]
(5)-38
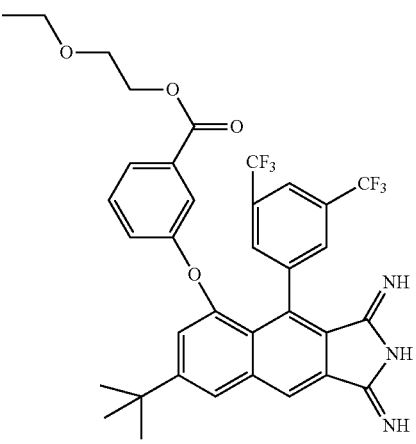 [SMILES: CCOCCOC(=O)c1cccc(Oc2cc(C(C)(C)C)cc3cc4c(c(-c5cc(C(F)(F)F)cc(C(F)(F)F)c5)c23)C(=N)NC4=N)c1]

TABLE 3-continued
(5)-39 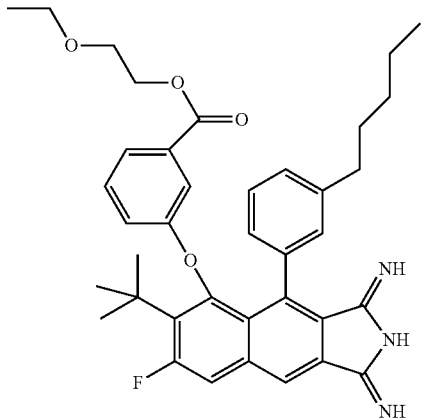 [SMILES: CCCCCc1cccc(-c2c3c(cc4cc(F)c(C(C)(C)C)c(Oc5cccc(C(=O)OCCOCC)c5)c24)C(=N)NC3=N)c1]
(5)-40 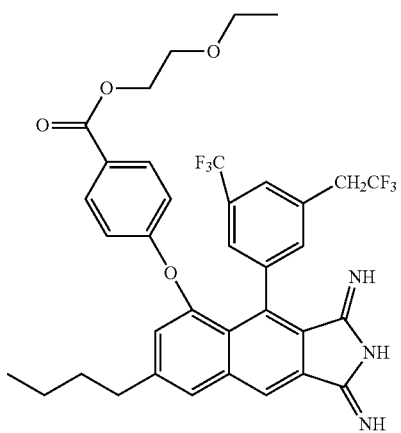
(5)-41 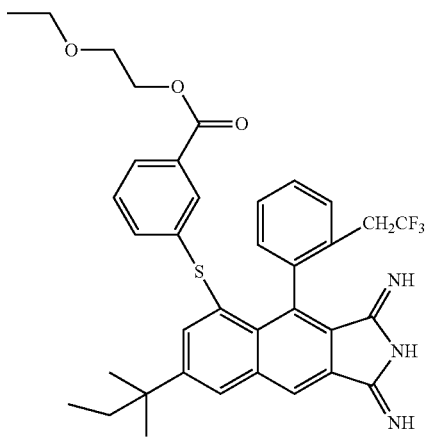

TABLE 3-continued
(5)-42
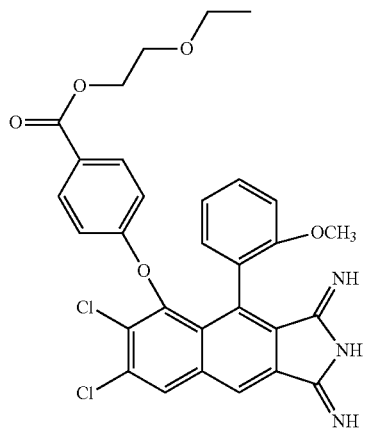 [SMILES: CCOCCOC(=O)c1ccc(Oc2c(Cl)c(Cl)cc3cc4c(c(-c5ccccc5OC)c23)C(=N)NC4=N)cc1]
(5)-43
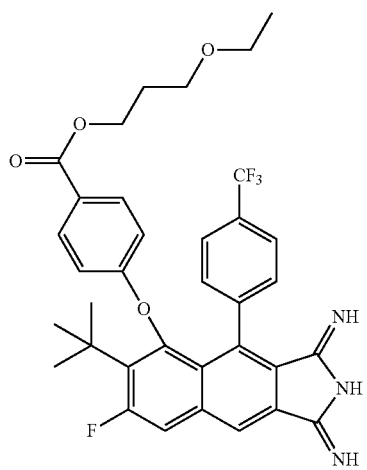 [SMILES: CCOCCCOC(=O)c1ccc(Oc2c(C(C)(C)C)c(F)cc3cc4c(c(-c5ccc(C(F)(F)F)cc5)c23)C(=N)NC4=N)cc1]
(5)-44
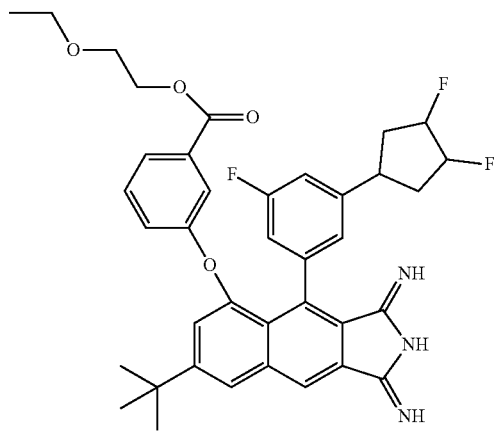 [SMILES: CCOCCOC(=O)c1cccc(Oc2cc(C(C)(C)C)cc3cc4c(c(-c5cc(F)cc(C6CC(F)C(F)C6)c5)c23)C(=N)NC4=N)c1]

TABLE 3-continued
(5)-45
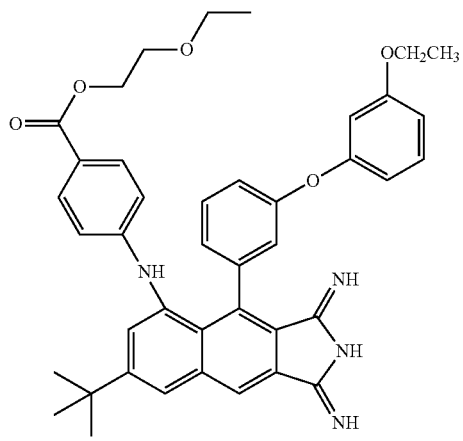 [SMILES: CCOCCOC(=O)c1ccc(Nc2cc(C(C)(C)C)cc3cc4c(c(-c5cccc(Oc6cccc(OCC)c6)c5)c23)C(=N)NC4=N)cc1]
(5)-46
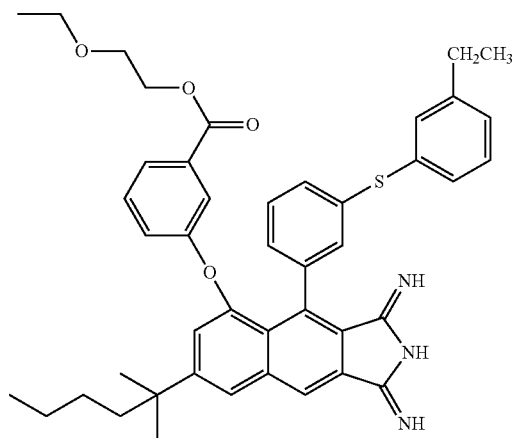 [SMILES: CCCCC(C)(C)c1cc(Oc2cccc(C(=O)OCCOCC)c2)c2c(-c3cccc(Sc4cccc(CC)c4)c3)c3c(cc2c1)C(=N)NC3=N]
(5)-47
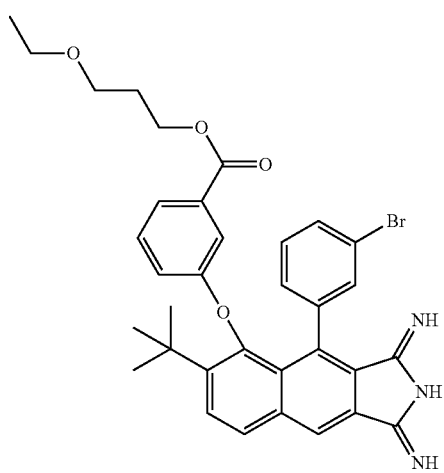 [SMILES: CCOCCCOC(=O)c1cccc(Oc2c(C(C)(C)C)ccc3cc4c(c(-c5cccc(Br)c5)c23)C(=N)NC4=N)c1]

TABLE 3-continued
(5)-48
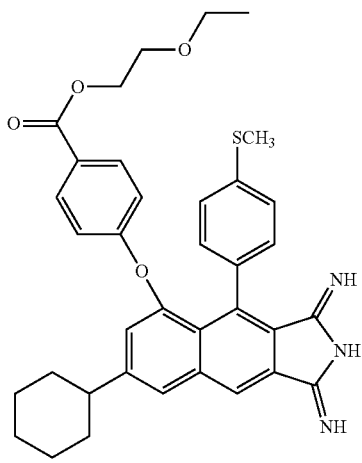 [SMILES: CCOCCOC(=O)c1ccc(Oc2cc(C3CCCCC3)cc3cc4c(c(-c5ccc(SC)cc5)c23)C(=N)NC4=N)cc1]
(5)-49
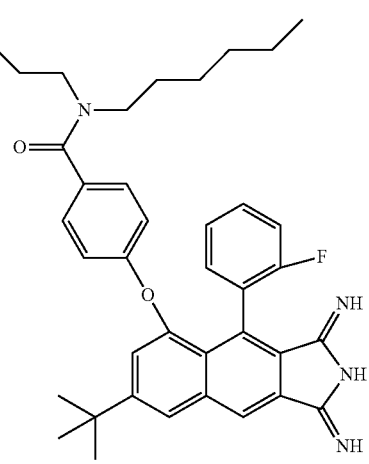
(5)-50
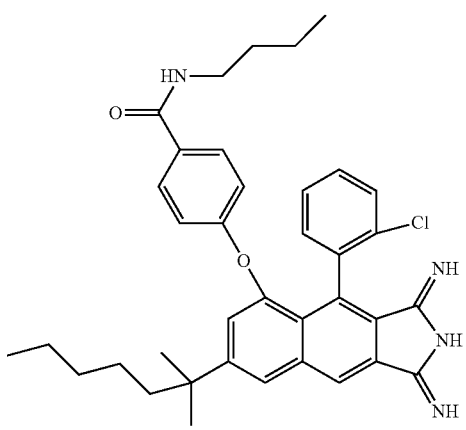 [SMILES: CCCCCC(C)(C)c1cc(Oc2ccc(C(=O)NCCCC)cc2)c2c(-c3ccccc3Cl)c3c(cc2c1)C(=N)NC3=N]

TABLE 3-continued
(5)-51
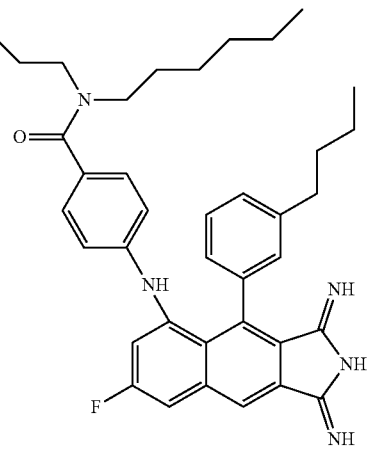
(5)-52
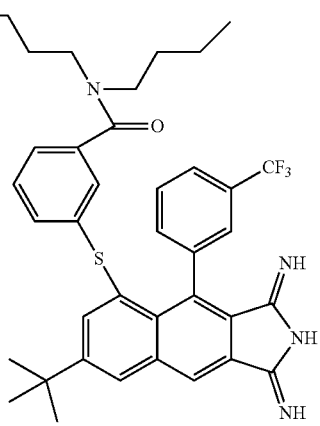
(5)-53
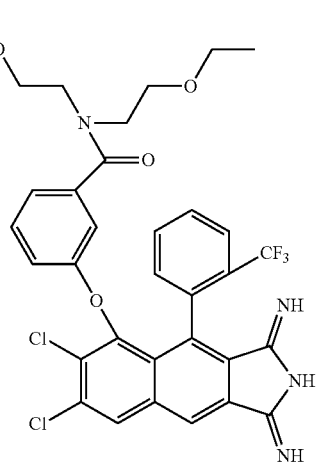

TABLE 3-continued
(5)-54
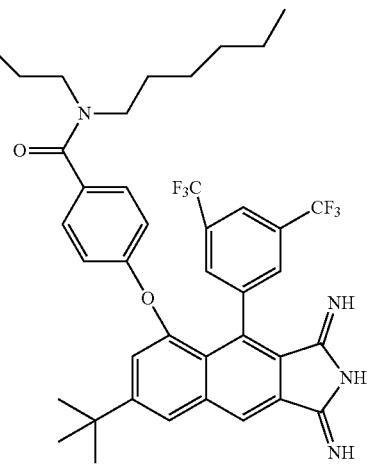
(5)-55
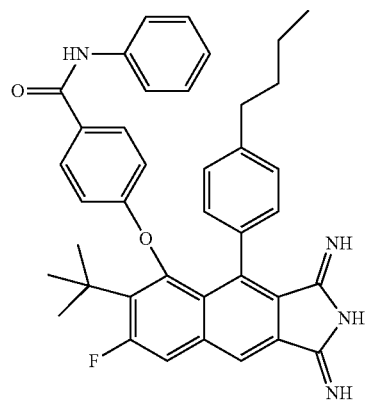 [SMILES: CCCCc1ccc(-c2c3c(cc4cc(F)c(C(C)(C)C)c(Oc5ccc(C(=O)Nc6ccccc6)cc5)c24)C(=N)NC3=N)cc1]
(5)-56
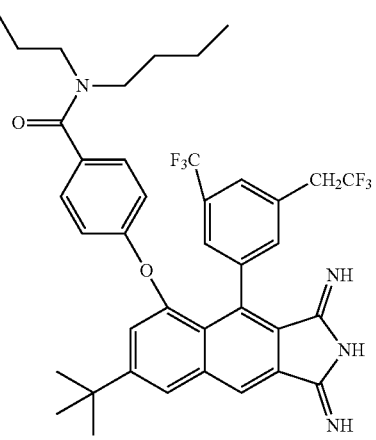

TABLE 3-continued
(5)-57
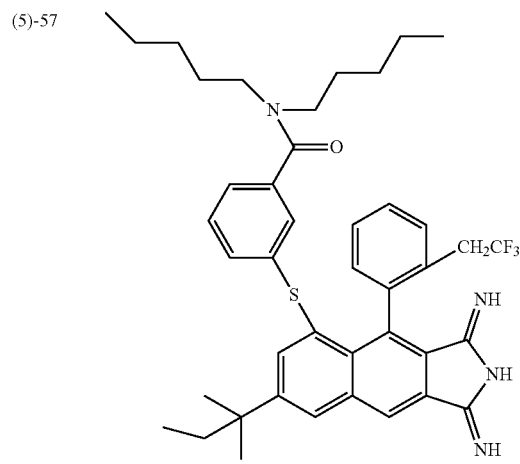
(5)-58
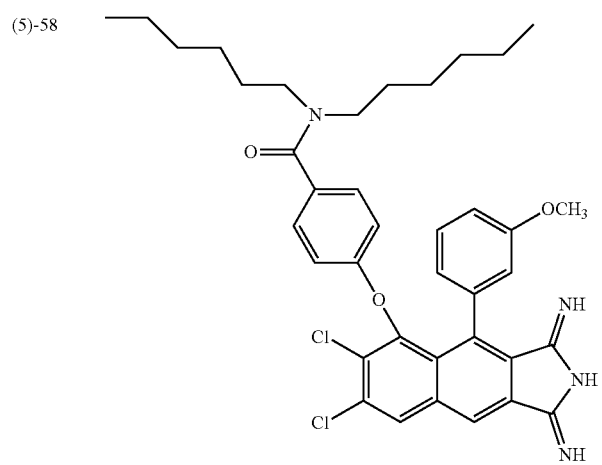
(5)-59
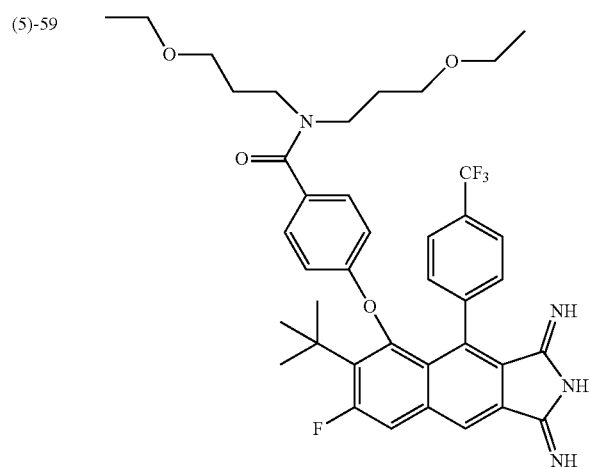

TABLE 3-continued
(5)-60 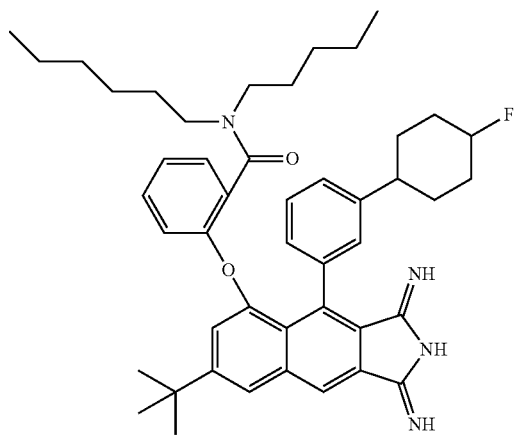 [SMILES: CCCCCCN(CCCCC)C(=O)c1ccccc1Oc1cc(C(C)(C)C)cc2cc3c(c(-c4cccc(C5CCC(F)CC5)c4)c12)C(=N)NC3=N]
(5)-61 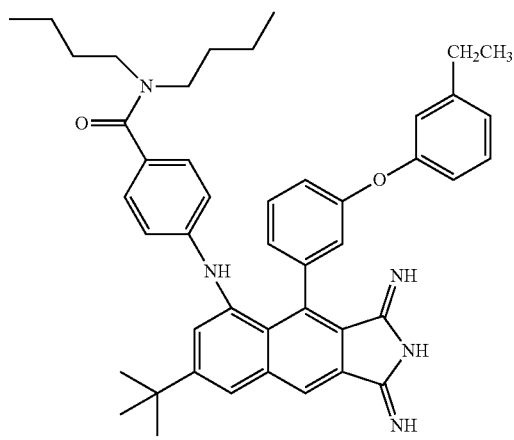 [SMILES: CCCCN(CCCC)C(=O)c1ccc(Nc2cc(C(C)(C)C)cc3cc4c(c(-c5cccc(Oc6cccc(CC)c6)c5)c23)C(=N)NC4=N)cc1]
(5)-62 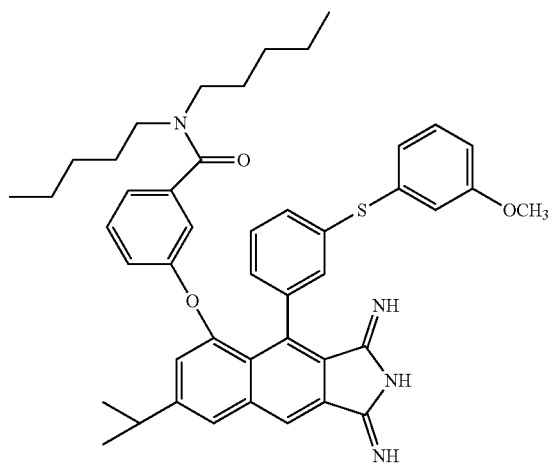 [SMILES: CCCCCN(CCCCC)C(=O)c1cccc(Oc2cc(C(C)C)cc3cc4c(c(-c5cccc(Sc6cccc(OC)c6)c5)c23)C(=N)NC4=N)c1]

TABLE 3-continued
(5)-63
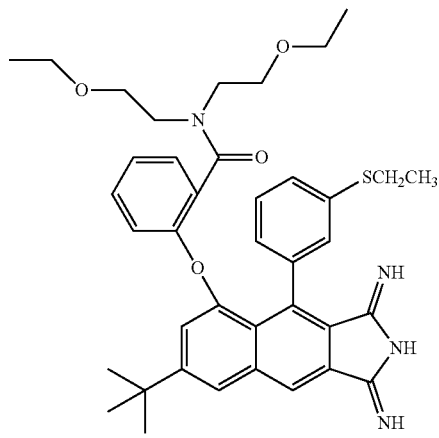
(5)-64
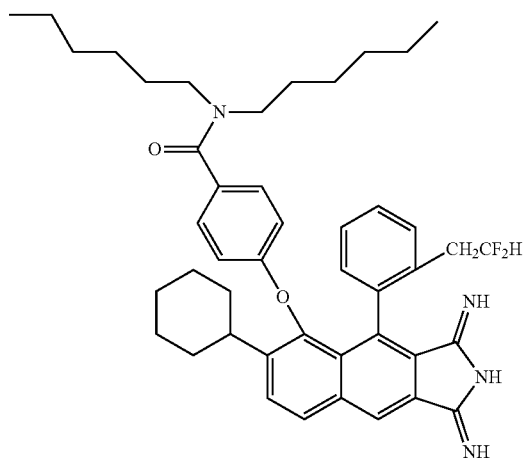
(5)-65
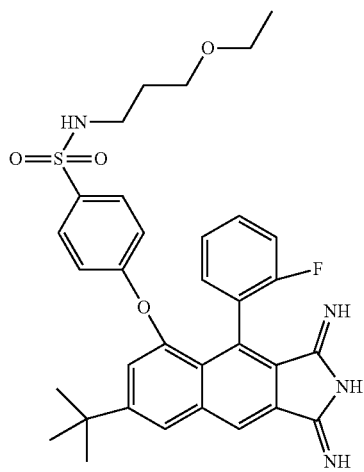 [SMILES: CCOCCCNS(=O)(=O)c1ccc(Oc2cc(C(C)(C)C)cc3cc4c(c(-c5ccccc5F)c23)C(=N)NC4=N)cc1]

TABLE 3-continued
(5)-66
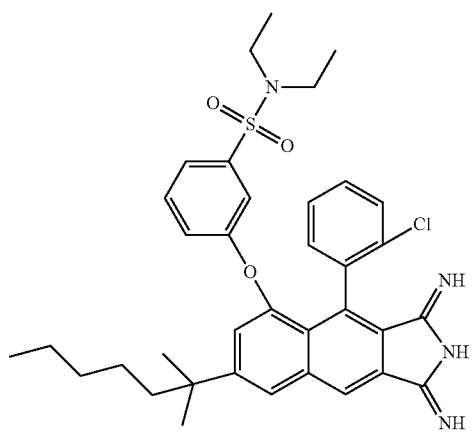 [SMILES: CCCCCC(C)(C)c1cc(Oc2cccc(S(=O)(=O)N(CC)CC)c2)c2c(-c3ccccc3Cl)c3c(cc2c1)C(=N)NC3=N]
(5)-67
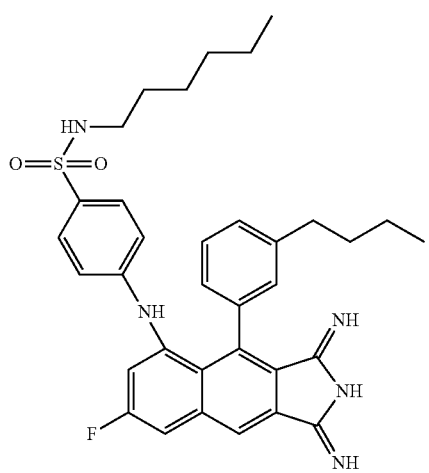 [SMILES: CCCCCCNS(=O)(=O)c1ccc(Nc2cc(F)cc3cc4c(c(-c5cccc(CCCC)c5)c23)C(=N)NC4=N)cc1]
(5)-68
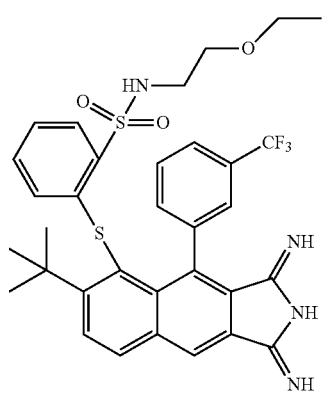 [SMILES: CCOCCNS(=O)(=O)c1ccccc1Sc1c(C(C)(C)C)ccc2cc3c(c(-c4cccc(C(F)(F)F)c4)c12)C(=N)NC3=N]

TABLE 3-continued
(5)-69
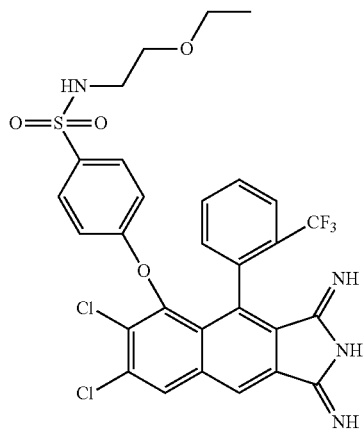 [SMILES: CCOCCNS(=O)(=O)c1ccc(Oc2c(Cl)c(Cl)cc3cc4c(c(-c5ccccc5C(F)(F)F)c23)C(=N)NC4=N)cc1]
(5)-70
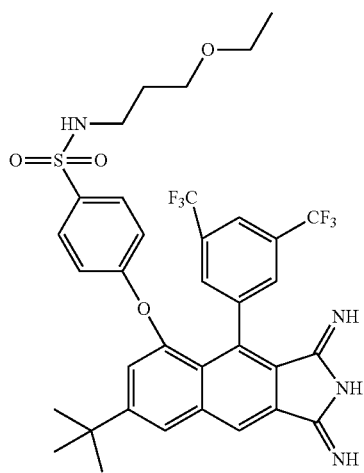 [SMILES: CCOCCCNS(=O)(=O)c1ccc(Oc2cc(C(C)(C)C)cc3cc4c(c(-c5cc(C(F)(F)F)cc(C(F)(F)F)c5)c23)C(=N)NC4=N)cc1]
(5)-71
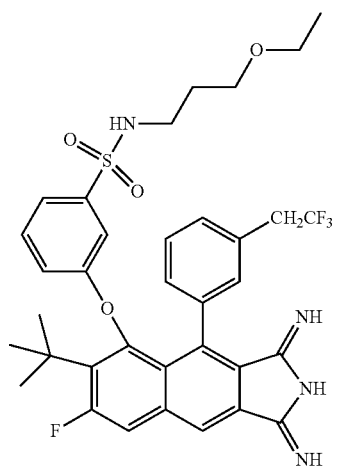

TABLE 3-continued
(5)-72
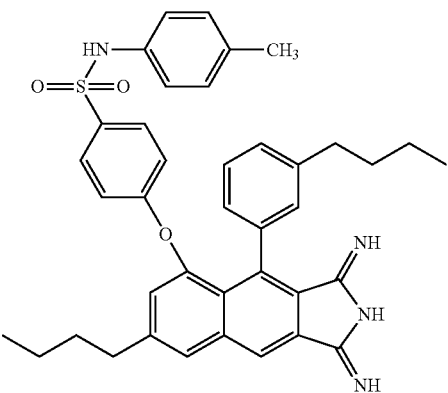 [SMILES: CCCCc1cccc(-c2c3c(cc4cc(CCCC)cc(Oc5ccc(S(=O)(=O)Nc6ccc(C)cc6)cc5)c24)C(=N)NC3=N)c1]
(5)-73
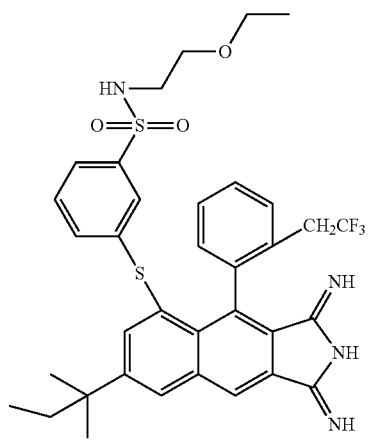
(5)-74
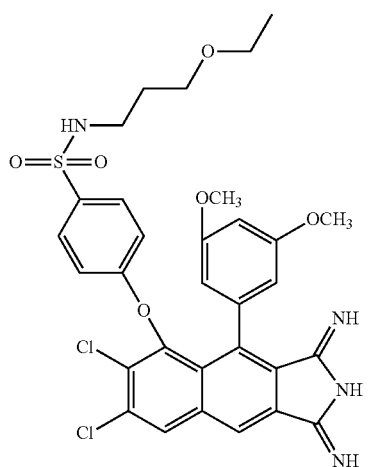 [SMILES: CCOCCCNS(=O)(=O)c1ccc(Oc2c(Cl)c(Cl)cc3cc4c(c(-c5cc(OC)cc(OC)c5)c23)C(=N)NC4=N)cc1]

TABLE 3-continued
(5)-75
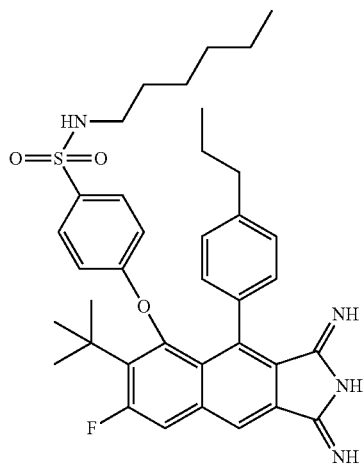 [SMILES: CCCCCCNS(=O)(=O)c1ccc(Oc2c(C(C)(C)C)c(F)cc3cc4c(c(-c5ccc(CCC)cc5)c23)C(=N)NC4=N)cc1]
(5)-76
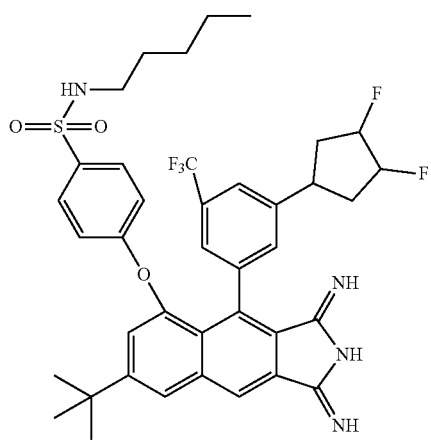 [SMILES: CCCCCNS(=O)(=O)c1ccc(Oc2cc(C(C)(C)C)cc3cc4c(c(-c5cc(C6CC(F)C(F)C6)cc(C(F)(F)F)c5)c23)C(=N)NC4=N)cc1]
(5)-77
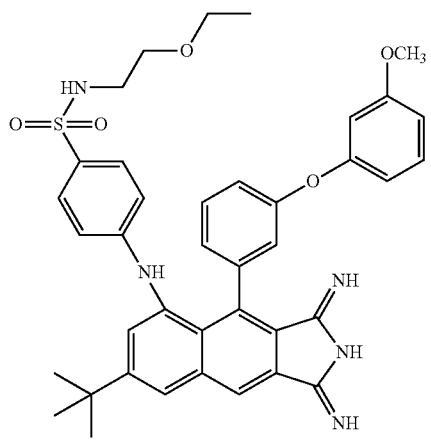 [SMILES: CCOCCNS(=O)(=O)c1ccc(Nc2cc(C(C)(C)C)cc3cc4c(c(-c5cccc(Oc6cccc(OC)c6)c5)c23)C(=N)NC4=N)cc1]

TABLE 3-continued (5)-78

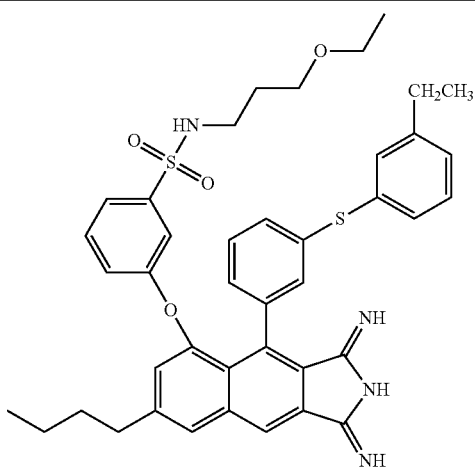

(5)-79

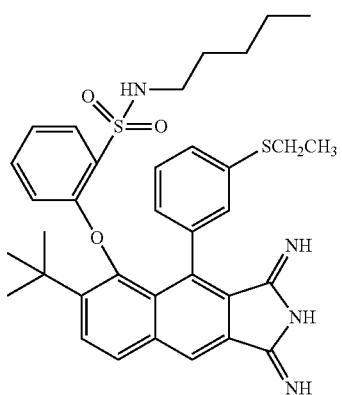

(5)-80

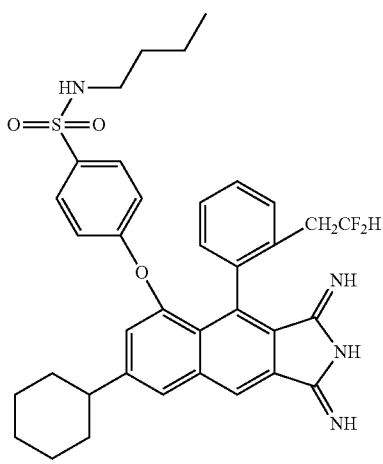

General Formula (5) can be produced with reference to known processes relating to known compounds.

For example, by blowing ammonia gas into the reaction system such that General Formula (4) reacts with the ammonia gas in the presence of a metal alkoxide, General Formula (5) can be produced.

The molar quantity of the ammonia is 1 to 20 times, and preferably 3 to 10 times with respect to 1 mol of General Formula (4).

Examples of the metal alkoxide include methoxide, ethoxide, n-propoxide, n-butoxide, n-pentoxide, n-hexyloxide, n-octyloxide, 2-methoxyethoxide, 2-methoxyethoxide, 2-ethoxyethoxide, and 2-butoxyethoxide of sodium or potassium, and the like.

The molar quantity of the metal alkoxide is 0.01 to 5 times, and preferably 0.1 to 2 times with respect to 1 mol of General Formula (4).

In the reaction, it is preferable to use an organic solvent in combination. Generally, as the organic solvent, an alcohol-based solvent is used. Examples of the alcohol-based solvent include methanol, ethanol, n-propanol, n-butanol, n-pentanol, n-hexanol, n-heptanol, n-octanol, 2-methoxyethanol, 2-ethoxyethanol, 2-butoxyethanol, and the like.

The amount of the alcohol-based solvent is 200 mL to 15 L, and preferably 500 mL to 5 L with respect to General Formula (4).

In the reaction operation, metallic sodium or metallic potassium may be added to the alcohol-based solvent as a reaction solvent such that an alcohol solution containing a metal alkoxide is prepared, and then ammonia and General Formula (4) may be added such that a reaction occurs. Alternatively, as another process, ammonia, General Formula (4), and a separately prepared metal alkoxide may be added to a reaction solvent such that a reaction occurs.

The molar quantity of the metal used for preparing the metal alkoxide is 0.01 to 5 times, and preferably 0.1 to 2 times with respect to 1 mol of General Formula (4).

The reaction temperature is 0° C. to a reflux temperature of the solvent, and preferably 20° C. to a reflux temperature of the solvent.

The reaction time is preferably 1 to 72 hours.

After the reaction ends, General Formula (4) can be obtained by being separated from the reaction system by general means. If necessary, by further performing a known purification operation such as recrystallization or column chromatography, General Formula (4) can be purified.

[Near-Infrared Absorbing Material]

Hereinafter, a near-infrared absorbing material of the present invention will be described.

The naphthalocyanine compound of the present invention is extremely useful as a near-infrared absorbing material having a wide range of uses such as a heat ray shielding material for shielding out heat rays, an optical filter for a plasma display or a liquid crystal display, a flash fixing toner, a photothermal conversion agent for thermosensitive transfer thermosensitive stencil, and the like, a photothermal conversion agent for laser welding, a pre-heating aid used for molding and processing a PET bottle, an optical recording medium using a semiconductor laser, a near-infrared absorbing pigment used in an optical character reader, and the like, a photosensitive pigment for treating tumors, and a near-infrared absorbing filter. The near-infrared absorbing material of the present invention may be the naphthalocyanine compound of the present invention represented by General Formula (1) or may contain the naphthalocyanine compound represented by General Formula (1) in addition to other components such as a binder resin or additives.

The aspects or components of the near-infrared absorbing material vary with the uses of the material and are diverse.

[Heat Ray Shielding Material]

Hereinafter, a heat ray shielding material of the present invention will be described.

The naphthalocyanine compound of the present invention is suitably used in a heat ray shielding material used in films or interlayers utilized in windows of building or automobiles, and the like, a PVC greenhouse, a sun visor, welding goggles, and the like. The heat ray shielding material of the present invention contains the naphthalocyanine compound of the present invention represented by General Formula (1).

The naphthalocyanine compound represented by General Formula (1) contained in the heat ray shielding material of the present invention may be used in the form of a single compound or a mixture of two or more kinds of compounds. Regarding the isomers thereof, among the isomers represented by General Formulae (1)-a to (1)-d, any one kind of isomer may be used, or a mixture of two or more kinds of isomers may be used.

Particularly, in view of storability such as light resistance or heat resistance of the heat ray shielding material, it is preferable that the content rate of the isomer represented by General Formula (1)-a is high among the isomers represented by General Formulae (1)-a to (1)-d.

The heat ray shielding material of the present invention may be used in any known form without particular limitation. Specifically, for example, the heat ray shielding material may be used in the following forms.

1. The form that a molded product, which contains the phthalocyanine-based compound represented by General Formula (1) and a resin as essential components, is used.

2. The form that a coating layer and a film, or the like, which contains the phthalocyanine-based compound represented by General Formula (1) and a resin as essential components, is applied over a substrate.

3. The form that a laminate is obtained by providing a film or the like, which contains the phthalocyanine-based compound represented by General Formula (1) and a resin as essential components, as an interlayer between two or more sheets of substrates.

4. The form that the phthalocyanine-based compound represented by General Formula (1) is contained in a substrate.

The substrate is not particularly limited, and examples thereof include a glass plate; a plastic plate including a plate material such as polycarbonate, polymethyl methacrylate, polystyrene, polyethylene terephthalate, polyvinyl chloride, polysulfone, unsaturated polyester; and the like.

Among the forms described above, particularly, "2. The form that a coating layer and a film, or the like, which contains the phthalocyanine-based compound represented by General Formula (1) and a resin as essential components, is applied over a substrate" and "3. The form that a laminate is obtained by providing a film or the like, which contains the phthalocyanine-based compound represented by General Formula (1) and a resin as essential components, as an interlayer between two or more sheets of substrates" are preferable.

As described above, in a preferred aspect, the heat ray shielding material of the present invention contains the naphthalocyanine compound represented by General Formula (1) and a resin as essential components.

The resin can be appropriately selected according to the use of the heat ray shielding material. It is preferable to use a resin which is substantially transparent and does not significantly absorb or scatter light.

Specifically, examples thereof include a polycarbonate resin; a (meth)acryl resin such as methyl methacrylate; a polyvinyl resin such as polystyrene, polyvinyl chloride, or polyvinylidene chloride; a polyolefin resin such as polyethylene or polypropylene; a polybutyral resin; a vinyl acetate-based resin such as polyvinyl acetate; a polyester resin; a polyamide resin; a polyvinyl acetal resin; a polyvinylalcohol resin; an ethylene-vinylacetate copolymer resin; an ethylene-acryl copolymer resin; a polyurethane resin, and the like. Furthermore, as long as the resin is substantially transparent, not only one kind of resin described above, but also a mixture obtained by blending two or more kinds of resins described above can also be used. In addition, the resin described above can also be used by being interposed between transparent glasses.

Among the above resins, a polycarbonate resin, a (meth)acryl resin, a polyester resin, a polyamide resin, a polystyrene resin, a polyvinyl chloride resin, a polyvinyl acetal resin, and a polyvinyl alcohol resin are preferable, and a polycarbonate resin, a methacryl resin, a polyethylene terephthalate (PET) resin, a polyvinylchloride resin, and a polyvinyl acetal resin are particularly more preferable.

The polycarbonate resin is produced by causing a reaction between divalent phenol and a carbonate precursor by a solution method or a melting method. Typical examples of the divalent phenol include 2,2-bis(4-hydroxyphenyl)propane [bisphenol A], 1,1-bis(4-hydroxyphenyl)ethane, 1,1-bis(4-hydroxyphenyl)cyclohexane, 2,2-bis(4-hydroxy-3,5-dimethylphenyl)propane, 2,2-bis(4-hydroxy-3,5-dibromophenyl)propane, 2,2-bis(4-hydroxy-3-methylphenyl)propane, bis(4-hydroxyphenyl)sulfide, bis(4-hydroxyphenyl)sulfone, and the like. As the divalent phenol, a bis(4-hydroxyphenyl)alkane-based compound is preferable, and a compound containing bisphenol as a main component is particularly preferable.

Examples of the (meth)acryl resin include methyl methacrylate, a mixture of polymerizable unsaturated monomers with a methyl methacrylate content equal to or higher than 50%, and a copolymer thereof. Examples of the polymerizable unsaturated monomers copolymerizable with methyl methacrylate include methyl acrylate, ethyl (meth)acrylate, butyl (meth)acrylate, cyclohexyl (meth)acrylate, 2-ethylhexyl (meth)acrylate, methoxyethyl (meth)acrylate, ethoxyethyl (meth)acrylate, 2-hydroxyethyl (meth)acrylate, N,N-diethylaminoethyl (meth)acrylate, glycidyl (meth)acrylate, tribromophenyl (meth)acrylate, tetrahydroxyfurfuryl (meth)acrylate, ethylene glycol di(meth)acrylate, triethylene glycol di(meth)acrylate, triporpylene glycol di(meth)acrylate, trimethylolethane di(meth)acrylate, neopentyl glycol di(meth)acrylate, trimethylolpropane tri(meth)acrylate, pentaerythritol tetra(meth)acrylate, and the like.

Typical examples of the polyester resin include homopolyester such as poly C2-4 alkylene terephthalate or poly C2-4 alkylene naphthalate, copolyester containing a C2-4 alkylene arylate unit (C2-4 alkylene terephthalate and/or C2-4 alkylene naphthalate unit) as a main component, and the like. The polyester resin also includes a polyarylate-based resin, aliphatic polyester using aliphatic dicarboxylic acid such as adipic acid, and a homopolymer or copolymer of lacton such as ε-caprolactone. For example, as the polyester resin, in view of high transparency, and the like, polyethylene terephthalate (PET), polytrimethylene terephthalate (PTT), polybutylene terephthalate (PBT), polyethylene naphthalate (PEN), and the like are preferable. Furthermore, amorphous copolyester such as C2-4 alkylene arylate-based copolyester is also preferable because this compound has excellent processability. Particularly, PET is preferable because this compound can be mass-produced and is excellent in heat resistance, strength, and the like.

The polyamide resin is a resin having a structure of a dehydropolycondensate of diamine compounds containing an aromatic or aliphatic group and dicarboxylic acid compounds containing an aromatic or aliphatic group. The aliphatic group also includes an alicyclicaliphatic group. Examples of the diamine compounds include hexamethylenediamine, m-xylenediamine, bis(4-aminocyclohexyl)methane, bis(4-amino-3-methylcyclohexyl)methane, trimethyl hexamethylenediamine, bis(aminomethyl)norbornane, bis(aminomethyl)tetrahydrodicyclopentadiene, and the like. Examples of the dicarboxylic acid compounds include adipic acid, dodecane dicarboxylic acid, isophthalic acid, terephthalic acid, bis(hydroxycarbonylmethyl)norbornane, bis(hydroxycarbonylmethyl)tetrahydrodicyclopentadiene, and the like. As the polyamide resin, particularly, from the viewpoint of transparency, an amorphous polyamide resin is preferable. Furthermore, generally, resins called transparent nylon are preferable.

As the polyvinyl chloride resin, not only a polymer containing only a vinyl chloride monomer, but also a copolymer containing vinyl chloride as a main component can also be used. Examples of monomers copolymerizable with vinyl chloride include vinylidene chloride, ethylene, propylene, acrylonitrile, vinyl acetate, maleic acid, itaconic acid, acrylic acid, methacrylic acid, and the like.

Examples of the polyvinyl acetal resin include a polyvinyl formal resin obtained by causing a reaction between polyvinylalcohol (PVA) and formaldehyde, a polyvinyl acetal resin in a narrow sense obtained by causing a reaction between PVA and acetaldehyde, a polyvinyl butyral resin (PVB) obtained by causing a reaction between PVA and n-butyraldehyde, and the like. Among these, PVB is preferable. The average degree of polymerization of PVA used for synthesizing the polyvinyl acetal resin is preferably 200 to 5,000, and more preferably 500 to 3,000. The degree of acetalization of the polyvinyl acetal resin is preferably 40 to 85 mol %, and more preferably 50 to 75 mol %.

The polyvinyl alcohol resin is obtained, for example, by saponifying polyvinyl acetate. The degree of saponification of the polyvinyl alcohol resin is generally within a range of 70 to 99.9 mol %, preferably within a range of 75 to 99.8 mol %, and even more preferably within a range of 80 to 99.8 mol. The average degree of polymerization of the polyvinyl alcohol resin is preferably equal to or higher than 500, and more preferably equal to or higher than 1,000 and equal to or lower than 5,000.

In the heat ray shielding material of the present invention, the content of the naphthalocyanine compound of the present invention represented by General Formula (1) varies with the thickness of the heat ray shielding material.

For example, in a case where a heat ray shielding plate having a thickness of 3 mm is prepared, the content of the naphthalocyanine compound is preferably 0.002 to 0.06 parts by weight, and more preferably 0.003 to 0.02 parts by weight with respect to 100 parts by weight of a resin mixed with the heat ray shielding material. Furthermore, for example, in a case where a heat ray shielding plate having a thickness of 10 mm is prepared, the content of the naphthalocyanine compound with respect to 100 parts by weight of a resin is preferably 0.0005 to 0.02 parts by weight, and more preferably 0.001 to 0.005 parts by weight. In a case where a heat ray shielding film having a thickness of 10 μm is prepared, the content of the naphthalocyanine compound is preferably 0.1 to 20 parts by weight, and more preferably 0.5 to 10 parts by weight with respect to 100 parts by weight of a resin. Provided that the content of the naphthalocyanine compound represented by General Formula (1) is described regardless of the thickness of the heat ray shielding material, the amount of the naphthalocyanine compound mixed in that is regarded as weight in a projection area from above is preferably 0.01 to 5.0 $g/m^2$, and more preferably 0.05 to 1.0 $g/m^2$. In a case where the amount of the naphthalocyanine compound represented by General Formula (1) mixed in is less than 0.01 $g/m^2$, the heat ray shielding effect is reduced. In a case where the amount of the naphthalocyanine compound represented by General Formula (1) mixed in is greater than 5.0 $g/m^2$, sometimes the transmission of visible rays is reduced.

The heat ray shielding material of the present invention may contain various additives used for producing general transparent resin materials, in addition to the naphthalocyanine compound represented by General Formula (1). Examples of the additives include a coloring agent, a polymerization regulator, an antioxidant, an ultraviolet absorber, a heat ray shielding agent, aflame retardant, a plasticizer, rubber for enhancing impact resistance, a release agent, and the like. The heat ray shielding agent means particles capable of absorbing infrared having a wavelength equal to or longer than 780 nm, and examples thereof include a metal oxide such as aluminum-doped tin oxide, indium-doped tin oxide, tin-doped indium oxide (ITO), antimony-doped tin oxide (ATO), or aluminum-doped zinc oxide (AZO), a tungsten oxide, a composite tungsten oxide, and the like. Particularly, tin-doped indium oxide (ITO) is preferable.

The amount of additives added to the heat ray shielding material is not particularly limited, and is generally equal to or smaller than 10% by weight in the heat ray shielding material.

Particularly, in a case where the heat ray shielding material of the present invention is used in a solar cell and the like, in a preferred aspect, the heat ray shielding material contains an ultraviolet absorber. As the ultraviolet absorber, known ultraviolet absorbers can be used without particular limitation. Specifically, compounds based on salicylic acid, benzophenone, benzotriazole, and cyanoacrylate are suitably used.

The heat ray shielding material of the present invention may contain another near-infrared absorbing material in addition to the naphthalocyanine compound represented by General Formula (1). As the aforementioned another near-infrared absorbing material, a known near-infrared absorbing material can be appropriately selected without particular limitation based on the maximum absorption wavelength desired according to use.

In the present invention, the shape of the heat ray shielding material is not particularly limited and includes various shapes such as a flat plate shape or a film shape which is most generally adopted, a corrugated plate shape, a spherical shape, and a dome shape.

In a case where the heat ray shielding material of the present invention has a flat plate shape or a film shape, by mixing the naphthalocyanine compound represented by General Formula (1) with a resin and, if necessary, the aforementioned additives or another near-infrared absorbing material and then molding the mixture, the heat ray shielding material is obtained. As the molding method, known molding methods can be used without particular limitation. Specifically, examples thereof include extrusion molding, injection molding, cast polymerization, press molding, calendar molding, cast film formation, and the like.

In a case where the heat ray shielding material of the present invention is used in the form of a film which is provided on a substrate and contains the naphthalocyanine compound represented by General Formula (1) and a resin as essential components, by bonding the film-like or sheet-like heat ray shielding material to the substrate by using an adhesive, a pressure sensitive adhesive, an adhesive film, and the like, the heat ray shielding material can be used in the form described above. Alternatively, by molding the film-like or sheet-like heat ray shielding material on the substrate by means of heat press or heat lamination, the heat ray shielding material can be used in the form described above.

In a case where the heat ray shielding material of the present invention is used in the form of a coating film which is provided on a substrate and contains the naphthalocyanine compound represented by General Formula (1) and a resin as essential components, by preparing a paint (liquid or paste-like substance), which contains the naphthalocyanine compound represented by General Formula (1), a resin, and, if necessary, a solvent dissolving the compound and the resin, and other components, and coating the substrate with the paint, the film can be used in the form of the coating film described above.

In a case where the heat ray shielding material of the present invention is used in the form that a laminate is obtained by providing a film or the like, which contains the phthalocyanine-based compound represented by General Formula (1) and a resin as essential components, as an interlayer between two or more sheets of substrates, for example, by interposing a film, which contains the phthalocyanine-based compound represented by General Formula (1) and a resin as essential components, between substrates, putting the laminate into a rubber pack, and heating the laminate while performing suction under reduced pressure such that the substrates and the film are bonded to each other in a vacuum, the heat ray shielding material can be used in the form of the laminate described above. Furthermore, by interposing a film, which contains the phthalocyanine-based compound represented by General Formula (1) and a resin as essential components, between substrates, or coating one substrate with a paint, which contains the phthalocyanine-based compound represented by General Formula (1), a resin, and, if necessary, a solvent dissolving the compound and the resin, or other components, and then placing another substrate thereon, and bonding the laminate of these by heat or the like, the heat ray shielding material can be used in the form of the laminate described above. In addition, by bonding substrates to each other by using an adhesive, which contains the phthalocyanine-based compound represented by General Formula (1) and a resin, or a composition which contains the phthalocyanine-based compound represented by General Formula (1) and a resin as a pressure sensitive adhesive, the heat ray shielding material can be used in the form of the laminate described above.

The uses of the heat ray shielding material of the present invention are not particularly limited, and examples thereof include a film or an interlayer used in windows of buildings or automobiles for shielding out heat rays of solar energy, a sun visor, welding goggles, and the like. Particularly, the naphthalocyanine compound represented by General Formula (1) of the present invention is excellently soluble in a solvent and excellently compatible with a resin and is excellent in various characteristics such as heat resistance, light resistance, and weather resistance. Therefore, the naphthalocyanine compound is suitable as a film or an interlayer used in windows of building or automobiles, and the like.

[Heat Ray Shielding Film]

Hereinafter, a case where the heat ray shielding material of the present invention is a heat ray shielding film used by being bonded to window glass of buildings and the like will be described.

The constitution of the heat ray shielding film is not particularly limited, and examples thereof include the following.

1. A form that the heat ray shielding film is a film containing the phthalocyanine-based compound represented by General Formula (1) and a resin.

2. A form that the heat ray shielding film has a film, which contains the phthalocyanine-based compound represented by General Formula (1) and a resin, a pressure sensitive adhesive layer, and, if necessary, a release sheet provided over a surface of the pressure sensitive adhesive layer.

3. A form that the heat ray shielding film is obtained by providing a layer, which contains the phthalocyanine-based compound represented by General Formula (1) and a resin, over a substrate.

4. A form that the heat ray shielding film has a layer, which contains the phthalocyanine-based compound represented by General Formula (1) and a resin as a pressure sensitive adhesive, and if necessary, a release sheet, which is provided on a surface of the pressure sensitive adhesive layer, on a substrate.

5. A form that the heat ray shielding film has a substrate, a layer, which contains the phthalocyanine-based compound represented by General Formula (1) and a resin, a pressure sensitive adhesive layer, and if necessary, a release sheet which is provided on a surface of the pressure sensitive adhesive layer.

Among the above aspects, in view of ease of bonding to window glass and the like, the aspect in which the heat ray shielding film has a pressure sensitive adhesive layer is preferable, and the aspect 4. or 5. is particularly preferable.

In addition to these aspects, according to purpose, the heat ray shielding film may be provided with other layers such as a hardcoat layer, an antifouling layer, an ultraviolet absorbing layer, and an antireflection layer.

Examples of the resin that the heat ray shielding film contains together with the phthalocyanine-based compound represented by General Formula (1) are the same as the examples of the resin that the heat ray shielding material contains. Particularly, a polycarbonate resin, a (meth)acryl resin, a polyvinyl resin, a polyolefin resin, a polybutyral resin, a polyester resin, a polyamide-based resin, and a polyurethane resin are preferable.

Examples of the substrate are the same as the examples of the substrate described above regarding the usage form of the heat ray shielding material. As the substrate, a sheet or plate made of resin is preferable. Examples thereof include films of polyester, polyethylene, polypropylene, nylon, polyvinyl chloride, polycarbonate, polyvinyl alcohol, polymethyl methacrylate, a fluororesin, ethylene, a vinyl alcohol resin, and the like. Among these, a polyester film is preferable, and a polyethylene terephthalate (PET) film is more preferable.

The pressure sensitive adhesive is not particularly limited as long as it can be bonded to the substrate and has transparency. Examples thereof include a thermoplastic or thermosetting resin pressure sensitive adhesive containing (meth)acryl based resin, (meth)acryl urethane based resin, (meth)acryl silicone based resin, silicone based resin having a siloxane bond on a main chain, polyvinyl chloride based resin, melamine based resin, urethane based resin, styrene based resin, alkyd based resin, phenol based resin, epoxy based resin, polyester based resin, and a fluorine-based resin such as polyvinylidene fluoride; curable resin pressure sensitive adhesive containing actinic energy ray-curable resin; a rubber-based pressure sensitive adhesive containing natural rubber, butyl rubber, isopropylene rubber, ethylene propylene rubber, methyl rubber, chloroprene rubber, ethylene-propylene copolymer rubber, styrene-butadiene rubber, or acrylonitrile-butadiene rubber, and the like.

Examples of the resin as a pressure sensitive adhesive include a thermoplastic or thermosetting resin and the curable thermosetting and actinic ray-curable resin described above. As the resin, a (meth)acryl-based resin is preferable, and a poly(meth)acrylic acid ester-based resin having a glass transition temperature less than 0° C. is particularly preferable.

As the poly(meth)acrylic acid ester-based resin, a resin is preferable in which a (meth)acrylic acid ester having an alkyl group containing 1 to 14 carbon atoms is used as a monomer in an amount equal to or greater than 50% by weight.

Examples of the copolymerizable monomer include (meth)acrylates such as hydroxyethyl (meth)acrylate, hydroxypropyl (meth)acrylate, methoxyethyl (meth)acrylate, ethoxyethyl (meth)acrylate, and ethoxyethoxyethyl (meth)acrylate; a styrene-based monomer represented by α-methyl styrene, vinyl toluene, styrene, and the like; a vinyl ether-based monomer represented by methyl vinyl ether, ethyl vinyl ether, isobutyl vinyl ether, and the like; fumaric acid, a monoalkyl ester of fumaric acid, and a dialkyl ester of fumaric acid; maleic acid, a monoalkylester of maleic acid, and dialkyl ester of maleic acid, itaconic acid, a monoalkyl ester of itaconic acid, a dialkyl ester of itaconic acid, (meth)acrylonitrile, vinylchloride, vinylidene chloride, vinyl acetate, vinyl ketone, vinyl pyridine, vinyl carbazole, and the like.

As a curing agent of the acryl-based pressure sensitive adhesive, an isocyanate-based curing agent, an epoxy-based curing agent, a metal chelate curing agent, and the like are used.

Each of the layers constituting the heat ray shielding film may contain the same additives as the various additives used for producing the heat ray shielding material described above. Examples thereof include a coloring agent, a polymerization regulator, an antioxidant, a light stabilizer, an ultraviolet absorber, a flame retardant, an antistatic agent, a plasticizer, and the like. In a preferred aspect, each of the layers contains an antioxidant, a flame retardant, an adhesion adjuster, an anti-moisture agent, a fluorescence brightening agent, and an ultraviolet absorber, and particularly, an ultraviolet absorber.

Furthermore, as long as the visible light transmittance is not reduced, a material such as carbon black that is capable of absorbing heat rays may be used in combination.

The thickness of the heat ray shielding film varies with the constitution of the heat ray shielding film, the type of the substrate or the resin of the heat ray shielding layer, uses thereof, and the like. Generally, a heat ray shielding film having a thickness of about 10 μm to 500 μm is preferably used.

For example, in a case where the heat ray shielding film is obtained by providing a layer, which contains the naphthalocyanine compound represented by General Formula (1) and a resin, on a substrate, the thickness of the substrate is preferably about 20 μm to 300 μm. Furthermore, the thickness of the layer containing the naphthalocyanine compound represented by General Formula (1) and a resin is preferably about 0.3 to 100 μm.

The content of the naphthalocyanine compound represented by General Formula (1) with respect to the resin depends on the thickness of the layer containing the naphthalocyanine compound represented by General Formula (1) and a resin. Generally, the content of the naphthalocyanine compound represented by General Formula (1) with respect to 100 parts by weight of the resin is preferably within a range of 0.001 to 30 parts by weight, and more preferably within a range of 0.01 to 10 parts by weight.

As a process for producing the heat ray shielding film of the present invention, the naphthalocyanine compound represented by General Formula (1) and a resin are mixed with the aforementioned additives and other near-infrared absorbers or ultraviolet absorbers which are used if necessary, and then the mixture is molded. The molding method is not particularly limited. Known molding methods can be used directly or used by being appropriately modified. Specifically, extrusion molding, injection molding, cast polymerization, press molding, calendar molding, cast film formation, and the like can be suitably used.

Furthermore, by preparing a resin film containing the naphthalocyanine compound represented by General Formula (1) and molding the film as a resin material by means of heat press or heat lamination, the heat ray shielding film can be produced. In addition, by printing an acryl resin ink or paint containing the naphthalocyanine compound represented by General Formula (1) on a resin material or by coating the resin material with the acryl resin ink or paint, the heat ray shielding film can be produced.

[Interlayer for Laminated Glass]

Hereinafter, a case where the heat ray shielding material of the present invention is an interlayer for laminated glass used in window glass of automobiles and the like will be described.

The interlayer for laminated glass is a resin film used by being interposed between two sheets of glass. In a case where the heat ray shielding material of the present invention is the interlayer for laminated glass, the interlayer contains the naphthalocyanine compound represented by General Formula (1) and a resin as essential components.

The resin is not particularly limited as long as the resin makes it possible to secure sufficient visibility in a case where the resin is used in laminated glass, and preferably as long as the visible light transmittance of laminated glass prepared using the resin is equal to or higher than 70%.

Examples of the resin include thermoplastic resins that have been conventionally used for interlayers, such as a polyvinyl acetal-based resin, a polyvinyl chloride-based resin, a saturated polyester-based resin, a polyurethane-based resin, an ethylene-vinyl acetate copolymer-based resin, and an ethylene-ethyl acrylate copolymer-based resin. Particularly, a plasticized polyvinyl acetal-based resin is preferable.

Examples of the polyvinylacetal-based resin include a polyvinyl formal resin obtained by causing a reaction between polyvinyl alcohol (PVA) and formaldehyde, a polyvinyl acetal resin in a narrow sense obtained by causing a reaction between PVA and acetaldehyde, a polyvinyl butyral resin (PVB) obtained by causing a reaction between PVA and n-butyraldehyde, and the like. Among these, a polyvinyl butyral resin (PVB) is particularly preferable.

The average degree of polymerization of PVA used for synthesizing the polyvinyl acetal-based resin is preferably 200 to 5,000, and more preferably 500 to 3,000. The degree of acetalization of the polyvinyl acetal-based resin is preferably 40 to 85 mol %, and more preferably 50 to 75 mol %. Furthermore, the amount of residual acetyl groups is preferably equal to or smaller than 30 mol %, and more preferably 0.5 to 24 mol %.

Examples of the thermoplastic resin, preferably the plasticizer used for plasticizing the polyvinyl acetal-based resin, include an organic acid ester-based plasticizer based on a monobasic organic acid ester or a polybasic organic acid ester, a phosphoric acid-based plasticizer based on organic phosphoric acid or organic phosphorous acid, and the like.

The thickness of the interlayer for laminated glass changes according to the type of the resin, the use of the resin, and the like. Generally, the thickness of the interlayer for laminated glass is preferably within a range of 0.1 to 3 mm, and more preferably within a range of 0.3 mm to 1.5 mm.

The content of the naphthalocyanine compound represented by General Formula (1) is not particularly limited with respect to the resin. The content of the naphthalocyanine compound represented by General Formula (1) is preferably within a range of 0.001 to 2 parts by weight, and more preferably within a range of 0.005 to 0.5 parts by weight with respect to 100 parts by weight of the resin.

The interlayer for laminated glass of the present invention may contain the same additives as the various additives used for synthesizing the heat ray shielding material described above. Examples thereof include a heat ray shielding agent, an ultraviolet absorber, an antioxidant, a light stabilizer, a flame retardant, an antistatic agent, an adhesion adjuster, an anti-moisture agent, a fluorescence brightening agent, a coloring agent, an infrared absorber, and the like. Particularly, an aspect is preferable in which the interlayer for laminated glass contains an ultraviolet absorber.

The interlayer for laminated glass of the present invention can be produced, for example, by the same method as the method used for producing the heat ray shielding material and the heat ray shielding film described above.

If necessary, the interlayer for laminated glass of the present invention may have a multilayer structure combined with a functional transparent layer having any one or more functions among a function of a primer, a function of cutting off ultraviolet rays, a flame retarding function, an antireflection function, an antiglare function, antireflection and antiglare functions, and an antistatic function.

The laminated glass in which the interlayer for laminated glass of the present invention is used is constituted with at least two sheets of transparent glass substrates and the interlayer of the present invention that is interposed between the substrates and integrated with the substrates by being bonded thereto.

The transparent glass substrate is not particularly limited, and examples thereof include various inorganic glass plates such as a float glass plate, a polished glass plate, a flat glass plate, a curved glass plate, a general glass plate, a figured glass plate, a figured glass plate with metal wires, an ultraviolet absorbing glass plate, clear glass, and a colored glass plate, organic glass plates such as a polycarbonate plate and a polymethyl methacrylate plate, and the like. One kind of transparent glass substrate described above may be used singly, or two or more kinds of transparent glass substrates described above may be used in combination.

The laminated glass can be prepared, for example, by a method of interposing the interlayer of the present invention between two sheets of transparent glass substrates, putting the laminate in a vacuum bag, preliminarily bonding the substrates and the interlayer to each other at a temperature of about 70° C. to 110° C. in a state of performing suction under reduced pressure such that the internal pressure of the vacuum bag is reduced and becomes about −65 to −100 kPa, and then permanently bonding the substrates and the interlayer to each other at a temperature of about 120° C. to 150° C. in an autoclave in a state of performing suction under reduced pressure such that the internal pressure of the autoclave is reduced and becomes about 0.98 to 1.47 MPa.

EXAMPLES

Hereinafter, the present invention will be more specifically described based on examples, but the present invention is not limited thereto.

In the present invention, each value was measured as below.

<1H-NMR>
AL-300 (300 MHz) manufactured by JEOL Ltd.
<LC-MS>
MICROMASS (ESI method) manufactured by WATERS.
<MALDI TOF-MS>
Shimadzu Biotech Axima Confidence
<FT-IR>
Spectrum One manufactured by PerkinElmer Inc.
<Elementary Analysis>
2400 II CHNS/O manufactured by PerkinElmer Inc.
<Wavelength and Gram Absorption Coefficient>
Spectrophotometer UV-4100 manufactured by Hitachi, Ltd.

[Example 1] Producing of 1-(3,5-bis(trifluoromethyl)phenyl)-6-t-butyl-8-fluoronaphthalene-2,3-dicarbonitrile 3,5-Bis(trifluoromethyl)-4'-t-butyl-6'-fluoro-2'-methylbenzophenone (37.2 g), 17.92 g of N-bromosuccinimide, and 0.62 g of a radical generator V-70 (azonitrile-based compound manufactured by Wako Pure Chemical Industries, Ltd.) were added to 160 mL of chlorobenzene, and the obtained solution was heated to 50° C. and allowed to react for 2 hours. The solution was cooled to room temperature, succinimide was removed by filtration, and 7.15 g of fumaronitrile was added thereto. Then, the obtained solution was heated to 120° C. and allowed to react for 16 hours. The reaction solution was cooled to 10° C., 54.6 g of concentrated sulfuric acid was added dropwise thereto, and then the solution was allowed to react for 1 hour. After the reaction ended, the chlorobenzene solution was rinsed with water, and the solvent was distilled away using an evaporator. The obtained solids were purified using methanol, thereby obtaining 13.6 g of white solids. From the following analysis results, it was confirmed that the obtained compound is the intended compound.

LC-MS: m/z 465 ([M+H]$^+$)
IR: νCN: 2230 cm$^{-1}$
Values of elementary analysis: actual measurement values (C: 62.57%, H: 3.35%, N: 5.85%); theoretical values (C: 62.07%, H: 3.26%, N: 6.03%)
$^1$H-NMR δ 1.43 (s, 9H), 7.45-7.49 (dd, 1H), 7.80 (d, 1H), 7.87 (s, 2H), 8.07 (s, 1H), 8.44 (d, 1H)

The $^1$H-NMR spectrum is shown in FIG. 1.

[Example 2] Producing of 1-(3,5-bis(trifluoromethyl)phenyl)-6-t-butyl-8-(3-methoxyphenoxy)naphthalene-2,3-dicarbonitrile (Specific Example (4)-1)

The compound obtained in Example 1 (6.0 g), 3.8 g of potassium carbonate, and 1.7 g of 3-methoxyphenol were added to 30 mL of DMI, the obtained solution was heated to 70° C. and allowed to react for 19 hours. The solution was cooled to room temperature, and 90 mL of water was added dropwise thereto stirred for 30 minutes. The obtained solids were filtered and rinsed with water, thereby obtaining 7.3 g of white solids. From the following analysis results, it was confirmed that the obtained compound is the intended compound.

LC-MS: m/z 569 ([M+H]$^+$)
IR: νCN: 2231 cm$^{-1}$
Values of elementary analysis: actual measurement values (C: 65.85%, H: 3.90%, N: 4.85%); theoretical values (C: 65.491, H: 3.90%, N: 4.93%)

[Example 3] Producing of 4-(3,5-bis(trifluoromethyl)phenyl)-7-t-butyl-5-(3-methoxyphenoxy)-1,3-diiminobenzisoindoline (Specific Example (5)-1)

Ammonia gas was blown into 4.0 mL of a 28% sodium methoxide solution, 7.0 g of the compound obtained in Example 2 and 70 mL of toluene were added thereto, and the obtained solution was heated to 60° C. and allowed to react for 3 hours. The solvent was distilled away, and 70 g of water was then added thereto and stirred for 1 hour. The obtained solids were filtered and then rinsed with water, thereby obtaining 7.1 g of yellow solids. From the following analysis results, it was confirmed that the obtained compound is the intended compound.

LC-MS: m/z 586 ([M+H]$^+$)
IR: νNH: 1624, 1668 cm$^{-1}$
Values of elementary analysis: actual measurement values (C: 63.75%, H: 4.35%, N: 7.03%); theoretical values (C: 63.59%, H: 4.30%, N: 7.18%)

[Example 4] Producing of Naphthalocyanine Compound (Specific Example (1)-9)

The compound obtained in Example 3 (7.0 g), 0.94 g of vanadium trichloride, and 0.91 g of DBU were added to 28 mL of DMI, and the obtained solution was heated to 110° C. and allowed to react for 30 minutes. The solution was then further heated to 120° C. and allowed to react for 3 hours. The solution was cooled to room temperature, and 28 mL of methanol was added dropwise thereto and stirred for 30 minutes. The obtained solids were filtered and rinsed with methanol, thereby obtaining 2.5 g of green solids. The solids were purified by column chromatography (silica gel and toluene), concentrated, then subjected to reflux in 50 mL of methanol, cooled, and filtered, thereby obtaining 2.2 g of green solids.

From the following analysis results, it was confirmed that the obtained compound is the intended compound.

MALDI TOF-MS: m/z 2341 (M$^+$)
Values of elementary analysis: actual measurement values (C: 63.92%, H: 3.92%, N: 4.75%); theoretical values (C: 63.62%, H: 3.79%, N: 4.79%)

Figure 2:
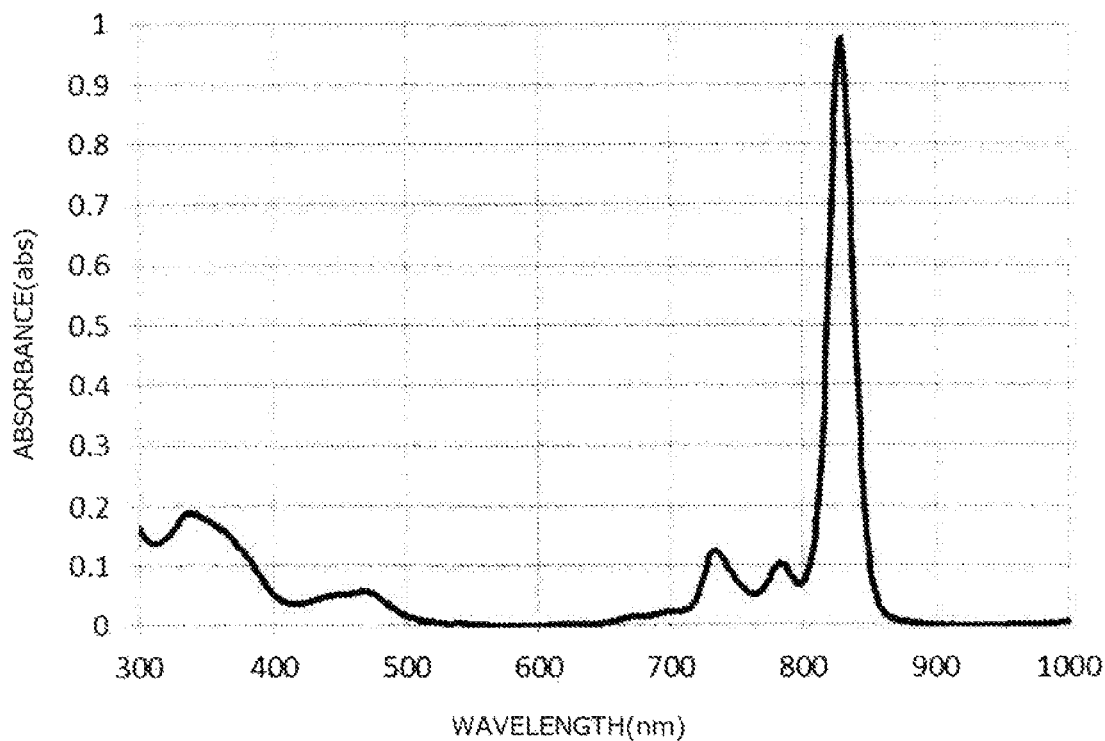
FIG. 2 is an absorption spectrum of a compound (1)-9 produced in Example 4.

A toluene solution of the compound obtained in this way had maximum absorption at 829 nm, and the gram absorption coefficient thereof was 1.93×10$^5$ mL/g·cm. The absorption spectrum chart thereof is illustrated in FIG. 2.

[Example 5] Producing of 4-(3,5-bis(trifluoromethyl)phenyl)-7-t-butyl-5-fluoro-1,3-diiminobenzisoindoline Yellow solids (9.6 g) were obtained in the same manner as in Example 3, except that, 11.0 g of the compound obtained in Example 1 was used instead of 7.0 g of the compound obtained in Example 2 in Example 3. From the following analysis results, it was confirmed that the obtained compound is the intended compound.

LC-MS: m/z 482 ([M+H]$^+$)
IR: νNH: 1626, 1669 cm$^{-1}$
Values of elementary analysis: actual measurement values (C: 59.98%, H: 3.90%, N: 8.63); theoretical values (C: 59.88%, H: 3.77%, N: 8.73%)

[Example 6] Producing of Naphthalocyanine Compound

The compound obtained in Example 5 (9.5 g) and 0.78 g of copper (I) chloride were added to 48 mL of DMI, and the obtained solution was heated to 100° C. and allowed to react for 30 minutes. The solution was further heated to 125° C. and allowed to react for 3 hours. The solution was cooled to room temperature, filtered, and rinsed with methanol, thereby obtaining 8.2 g of green solids.

From the following analysis results, it was confirmed that the obtained compound is the intended compound.

LC-MS: m/z 1922 ([M+H]$^+$)
Values of elementary analysis: actual measurement values (C: 60.27%, H: 3.32%, N: 5.72%); theoretical values (C: 60.02%, H: 3.15%, N: 5.83%)

[Example 7] Producing of Naphthalocyanine Compound (Specific Example (1)-11)

The compound obtained in Example 6 (8.1 g), 4.70 g of potassium carbonate, and 5.51 g of 4-(4-hydroxyphenyl)-2-butanone were added to 122 mL of DMI, and the obtained solution was heated to 170° C. and allowed to react for 4.5 hours. The solution was cooled to room temperature, and 60 g of water was then added dropwise thereto and stirred for 1 hour. The obtained solids were filtered, rinsed with water, and further rinsed with methanol, thereby obtaining 9.7 g of green solids.

The green solids were purified by column chromatography (silica gel and toluene/ethyl acetate=100/25, v/v), concentrated, then subjected to reflux in 90 mL of methanol, cooled, and filtered, thereby obtaining 7.6 g of green solids. From the following analysis results, it was confirmed that the obtained compound is the intended compound.

MALDI TOF-MS: m/z 2497 ($M^+$)

Values of elementary analysis: actual measurement values (C: 65.63%, H: 4.33%, N: 4.38%); theoretical values (C: 65.40%, H: 4.20%, N: 4.49%)

Figure 3:
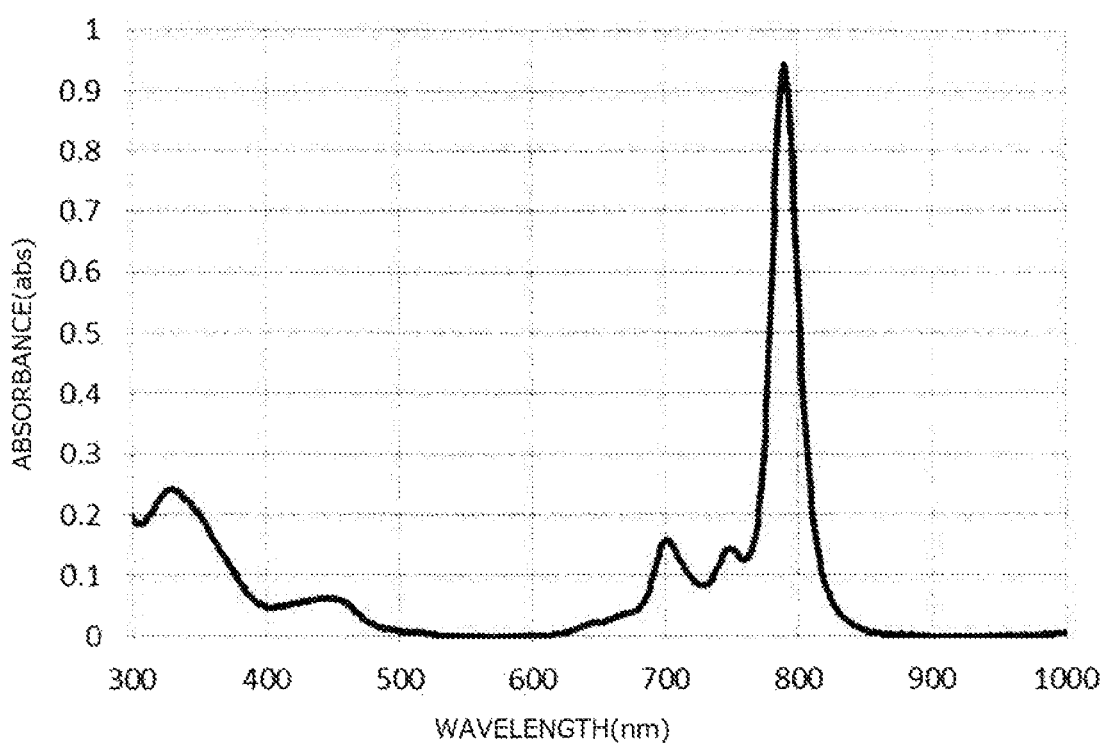
FIG. 3 is an absorption spectrum of a compound (1)-11 produced in Example 7.

A toluene solution of the compound obtained in this way had maximum absorption at 791 nm, and the gram absorption coefficient thereof was $1.49 \times 10^5$ mL/g·cm. The absorption spectrum chart thereof is illustrated in FIG. 3.

[Example 8] Producing of Naphthalocyanine Compound

Green solids (1.9 g) were obtained in the same manner as in Example 4, except that, 5.0 g of the compound obtained in Example 5 was used instead of 7.0 g of the compound obtained in Example 3 in Example 4.

From the following analysis results, it was confirmed that the obtained compound is the intended compound.

LC-MS: m/z 1925 ($[M+H]^+$)

Values of elementary analysis: actual measurement values (C: 60.26%, H: 3.27%, N: 5.75%); theoretical values (C: 59.91, H: 3.14%, N: 5.82%)

[Example 9] Producing of Naphthalocyanine Compound (Specific Example (1)-12)

Green solids (1.0 g) were obtained in the same manner as in Example 7, except that, 1.8 g of the compound obtained in Example 8 was used instead of 8.1 g of the compound obtained in Example 6 in Example 7. From the following analysis results, it was confirmed that the obtained compound is the intended compound.

MALDI TOF-MS: m/z 2501 ($M^+$)

Values of elementary analysis: actual measurement values (C: 65.47%, H: 4.32%, N: 4.37%); theoretical values (C: 65.31%, H: 4.19%, N: 4.48%)

Figure 4:
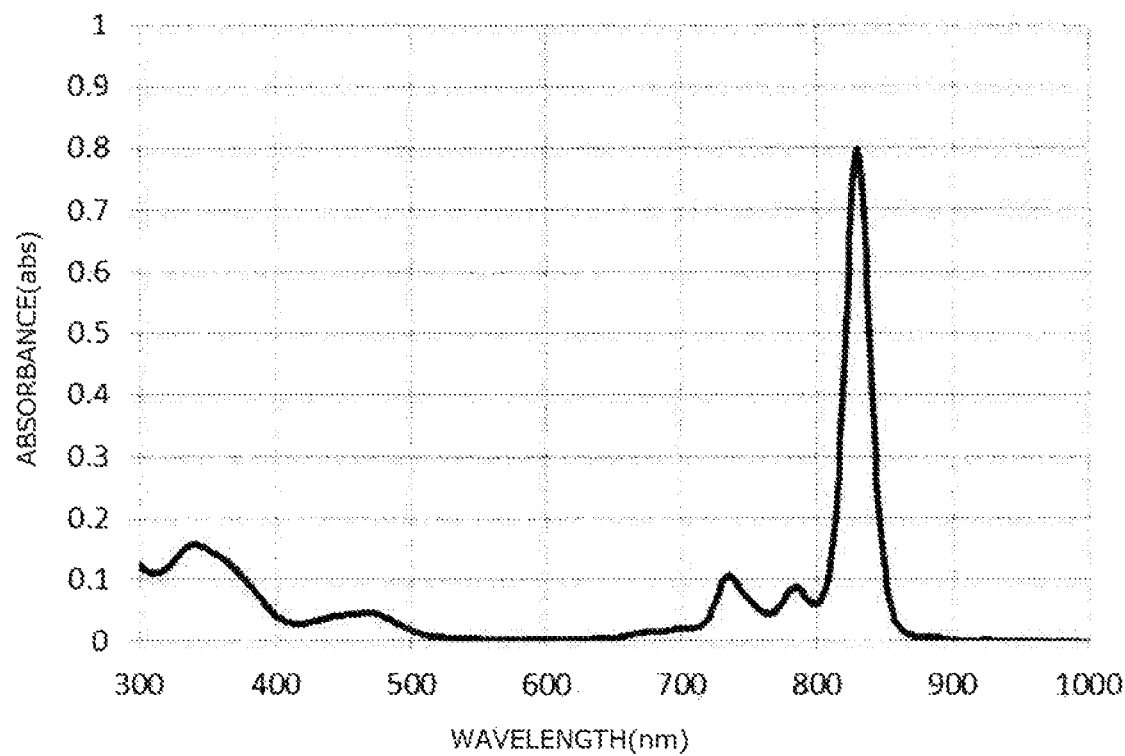
FIG. 4 is an absorption spectrum of a compound (1)-12 produced in Example 9.

A toluene solution of the compound obtained in this way had maximum absorption at 830 nm, and the gram absorption coefficient thereof was $1.78 \times 10^5$ mL/g·cm. The absorption spectrum chart thereof is illustrated in FIG. 4.

[Example 10] Producing of Naphthalocyanine Compound (Specific Example (1)-28)

The compound obtained in Example 6 (3.0 g), 2.42 g of butyl 4-hydroxybenzoic acid, and 1.72 g of potassium carbonate were added to 45 mL of DMI, and the obtained solution was heated to 170° C. and allowed to react for 6.5 hours. The solution was cooled to room temperature, 2.29 g of butyl iodide was added thereto, and then the solution was heated to 80° C. and allowed to react for 3.5 hours. The solution was cooled to room temperature, and then 45 g of water was added dropwise thereto and stirred for 1 hour. The obtained solids were filtered, rinsed with water, and further rinsed with methanol, thereby obtaining 4.1 g of green solids. The green solids were purified by column chromatography (silica gel and toluene/ethyl acetate=100/2, v/v), concentrated, then subjected to reflux in 20 mL of butanol, cooled, and filtered, thereby obtaining 3.3 g of green solids. From the following analysis results, it was confirmed that the obtained compound is the intended compound.

MALDI TOF-MS: m/z 2618 ($M^+$)

Values of elementary analysis: actual measurement values (C: 64.42%, H: 4.46%, N: 4.09%); theoretical values (C: 64.23%, H: 4.31%, N: 4.28%)

Figure 5:
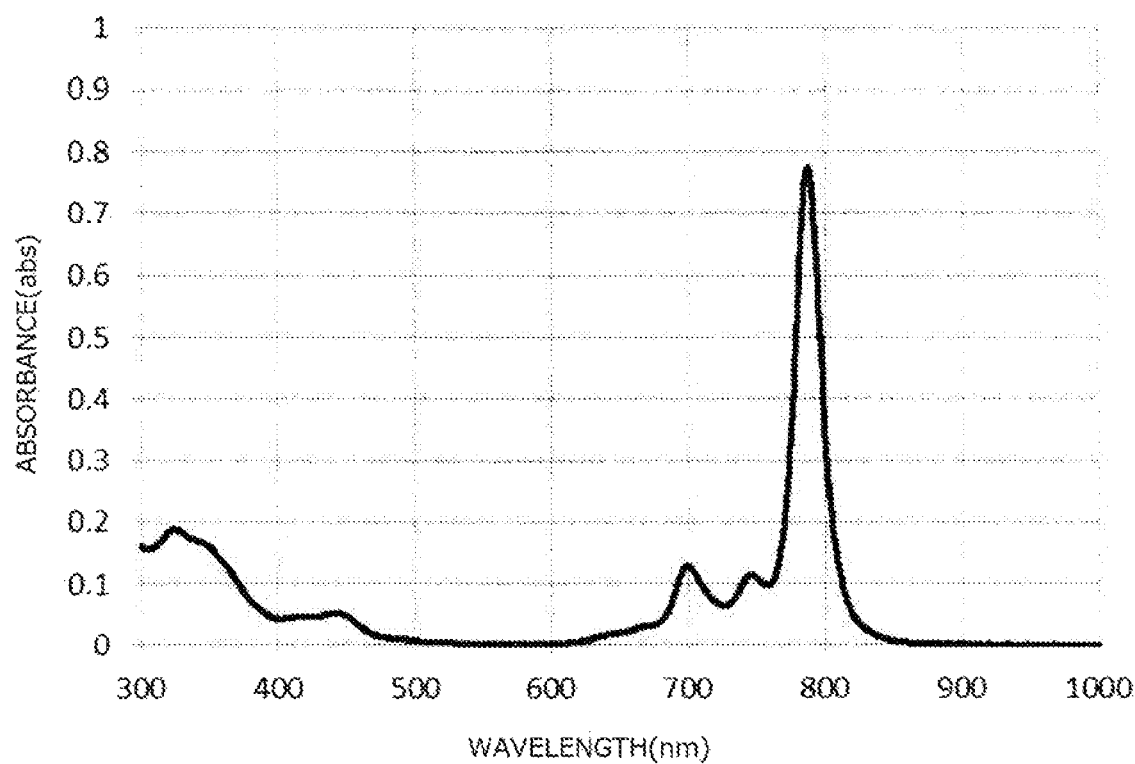
FIG. 5 is an absorption spectrum of a compound (1)-28 produced in Example 10.

A toluene solution of the compound obtained in this way had maximum absorption at 788 nm, and the gram absorption coefficient thereof was $1.46 \times 10^5$ mL/g·cm. The absorption spectrum chart thereof is illustrated in FIG. 5.

[Example 11] Producing of Naphthalocyanine Compound (Specific Example (1)-42)

The compound obtained in Example 6 (1.5 g), 1.31 g of ethoxyethyl 3-hydroxybenzoic acid, and 0.86 g of potassium carbonate were added to 25 mL of DMI, and the obtained solution was heated to 170° C. and allowed to react for 4 hours. The solution was cooled to room temperature, 0.95 g of 2-ethoxyethyl bromide was added thereto, and then the solution was heated to 85° C. and allowed to react for 2.5 hours. The solution was cooled to room temperature, and then 25 g of water was added dropwise thereto and stirred for 1 hour. The obtained solids were filtered, rinsed with water, and further rinsed with methanol, thereby obtaining 2.1 g of green solids. The green solids were purified by column chromatography (silica gel and toluene/ethyl acetate=100/5, v/v), concentrated, and then recrystallized over 30 mL of 2-ethoxyethanol, thereby obtaining 1.3 g of green solids. From the following analysis results, it was confirmed that the obtained compound is the intended compound.

MALDI TOF-MS: m/z 2682 ($M^+$)

Figure 6:
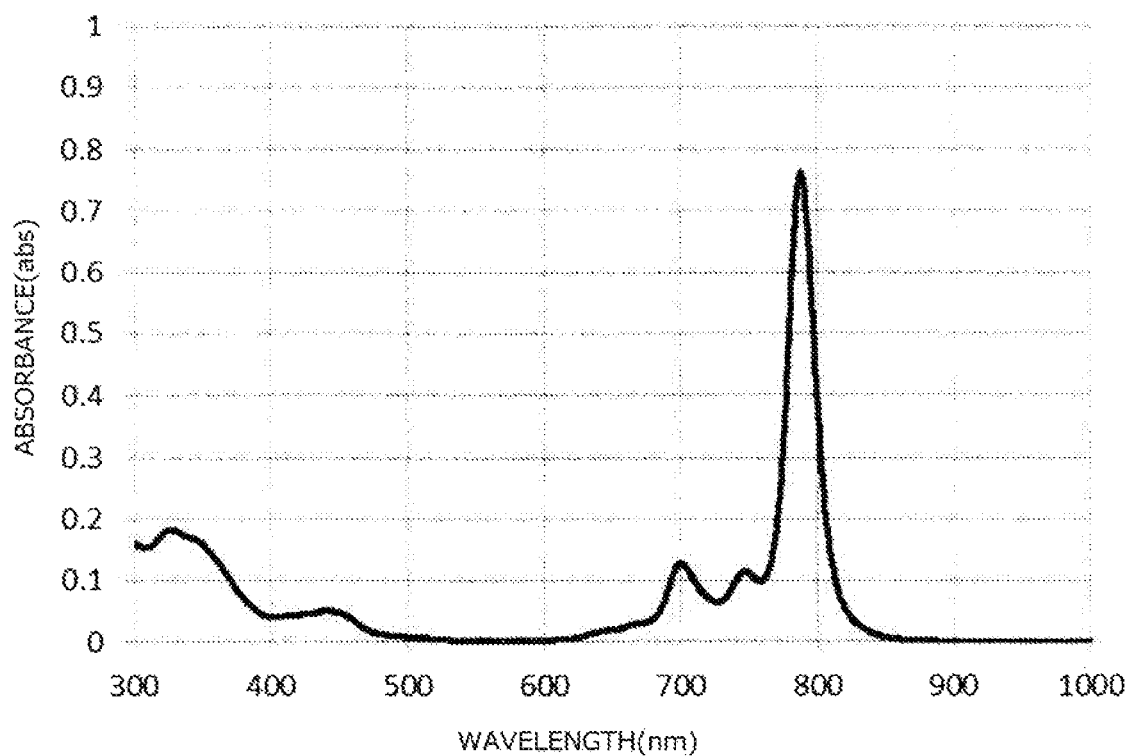
FIG. 6 is an absorption spectrum of a compound (1)-42 produced in Example 11.

Values of elementary analysis: actual measurement values (C: 62.92%, H: 4.33%, N: 4.03%); theoretical values (C: 62.70%, H: 4.21%, N: 4.18%) A toluene solution of the compound obtained in this way had maximum absorption at 789 nm, and the gram absorption coefficient thereof was $1.37 \times 10^5$ mL/g·cm. The absorption spectrum chart thereof is illustrated in FIG. 6.

[Example 12] Producing of Naphthalocyanine Compound (Specific Example (1)-50)

The compound obtained in Example 6 (1.5 g), 1.91 g of N,N-dihexyl-4-hydroxybenzamide, and 0.86 g of potassium carbonate were added to 25 mL of DMI, and the obtained solution was heated to 170° C. and allowed to react for 4 hours. The solution was cooled to room temperature, and then 12 g of water added dropwise thereto and stirred for 1 hour. The obtained solids were filtered, rinsed with water, and further rinsed with methanol, thereby obtaining 2.1 g of green solids. The green solids were purified by column chromatography (silica gel and toluene/ethyl acetate=100/5, v/v), concentrated, and then dispersed in 20 mL of methanol, thereby obtaining 1.7 g of green solids. From the following analysis results, it was confirmed that the obtained compound is the intended compound.

MALDI TOF-MS: m/z 3062 (M+)

Values of elementary analysis: actual measurement values (C: 67.55%, H: 5.98%, N: 5.41%); theoretical values (C: 67.45, H: 5.92%, N: 5.49%)

Figure 7:
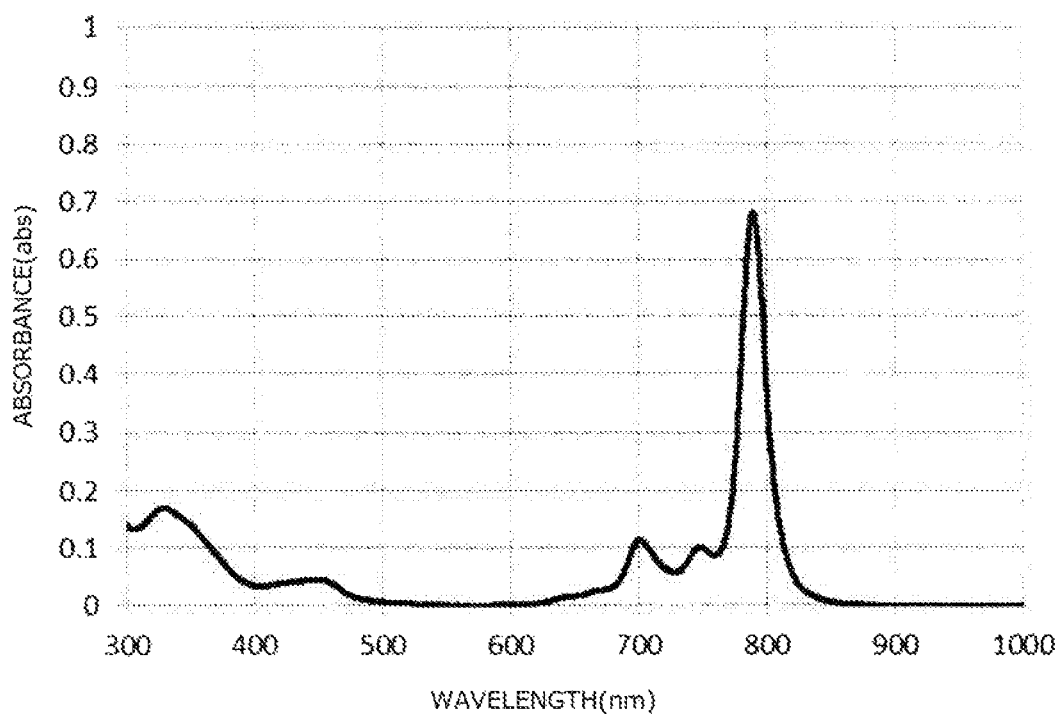
FIG. 7 is an absorption spectrum of a compound (1)-50 produced in Example 12.

A toluene solution of the compound obtained in this way had maximum absorption at 790 nm, and the gram absorption coefficient thereof was $1.24\times10^5$ mL/g·cm. The absorption spectrum chart thereof is illustrated in FIG. 7.

[Example 13] Producing of 1-(2-fluorophenyl)-6-t-butyl-8-fluoronaphthalene-2,3-dicarbonitrile White solids (18.3 g) were obtained in the same manner as in Example 1, except that, 30.0 g of 2-fluoro-4'-t-butyl-6'-fluoro-2'-methyl benzophenone was used instead of 37.2 g of 3,5-bis(trifluoromethyl)-4'-t-butyl-6'-fluoro-2'-methyl-benzophenone in Example 1. From the following analysis results, it was confirmed that the obtained compound is the intended compound.

LC-MS: m/z 347 ([M+H]+)

IR: νCN: 2223 cm$^{-1}$

Values of elementary analysis: actual measurement values (C: 76.43%, H: 4.76%, N: 7.95%); theoretical values (C: 76.29%, H: 4.66%, N: 8.09%)

Figure 8:
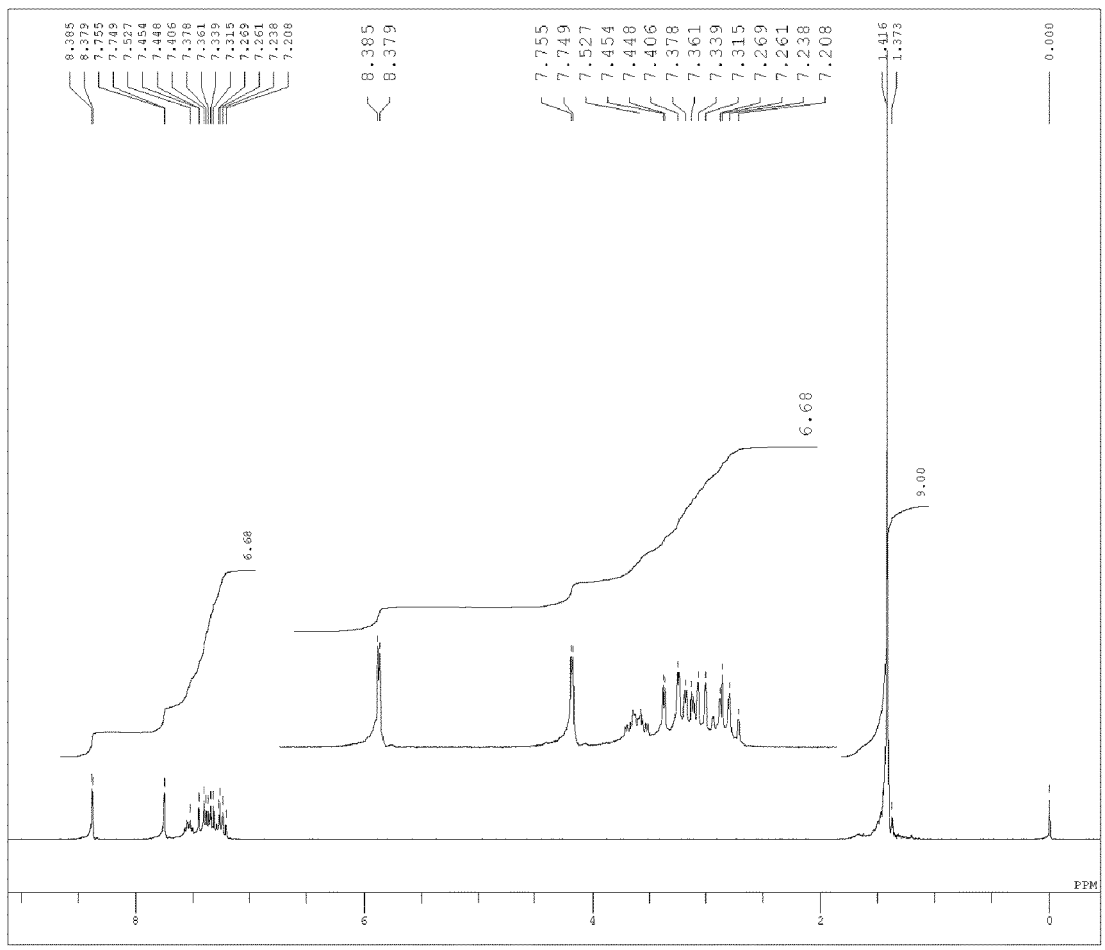
FIG. 8 is a $^1$H-NMR spectrum of a compound produced in Example 13.

The H-NMR spectrum thereof is illustrated in FIG. 8.

[Example 14] Producing of 4-(2-fluorophenyl)-7-t-butyl-5-fluoro-1,3-diiminobenzisoindoline Yellow solids (13.2 g) were obtained in the same manner as in Example 3, except that, 13.0 g of the compound obtained in Example 13 was used instead of 7.0 g of the compound obtained in Example 2 in Example 3. From the following analysis results, it was confirmed that the obtained compound is the intended compound.

LC-MS: m/z 364 ([M+H]+)

IR: νNH: 1622, 1664 cm$^{-1}$

Values of elementary analysis: actual measurement values (C: 72.75%, H: 5.30%, N: 11.32%); theoretical values (C: 72.71%, H: 5.27%, N: 11.56%)

[Example 15] Producing of Naphthalocyanine Compound

Green solids (3.2 g) were obtained in the same manner as in Example 6, except that, 6.0 g of the compound obtained in Example 14 was used instead of 9.5 g of the compound obtained in Example 5. From the following analysis results, it was confirmed that the obtained compound is the intended compound.

LC-MS: m/z 1450 ([M+H]+)

Values of elementary analysis: actual measurement values (C: 73.06%, H: 4.47%, N: 7.70%); theoretical values (C: 72.94%, H: 4.45%, N: 7.73%)

A toluene solution of the compound obtained in this way had maximum absorption at 778 nm, and the gram absorption coefficient thereof was $2.48\times10^5$ mL/g·cm.

[Example 16] Producing of Naphthalocyanine Compound (Specific Example (1)-52)

The compound obtained in Example 15 (0.75 g), 0.58 g of potassium carbonate, and 1.27 g of N,N-dihexyl-4-hydroxy-benzamide were added to 15 mL of DMI, and the obtained solution was heated to 195° C. and allowed to react for 15 hours. The solution was cooled to room temperature, and then 7 g of water added dropwise thereto and stirred for 1 hour. The obtained solids were filtered, rinsed with water, and further rinsed with methanol, thereby obtaining 0.9 g of green solids. The green solids were purified by column chromatography (silica gel and toluene/ethyl acetate=100/20, v/v), concentrated, and then dispersed in 10 mL of methanol, thereby obtaining 0.6 g of green solids. From the following analysis results, it was confirmed that the obtained compound is the intended compound.

MALDI TOF-MS: m/z 2590 (M+)

Values of elementary analysis: actual measurement values (C: 76.10%, H: 7.25%, N: 6.27%); theoretical values (C: 76.03%, H: 7.16%, N: 6.49%)

Figure 9:
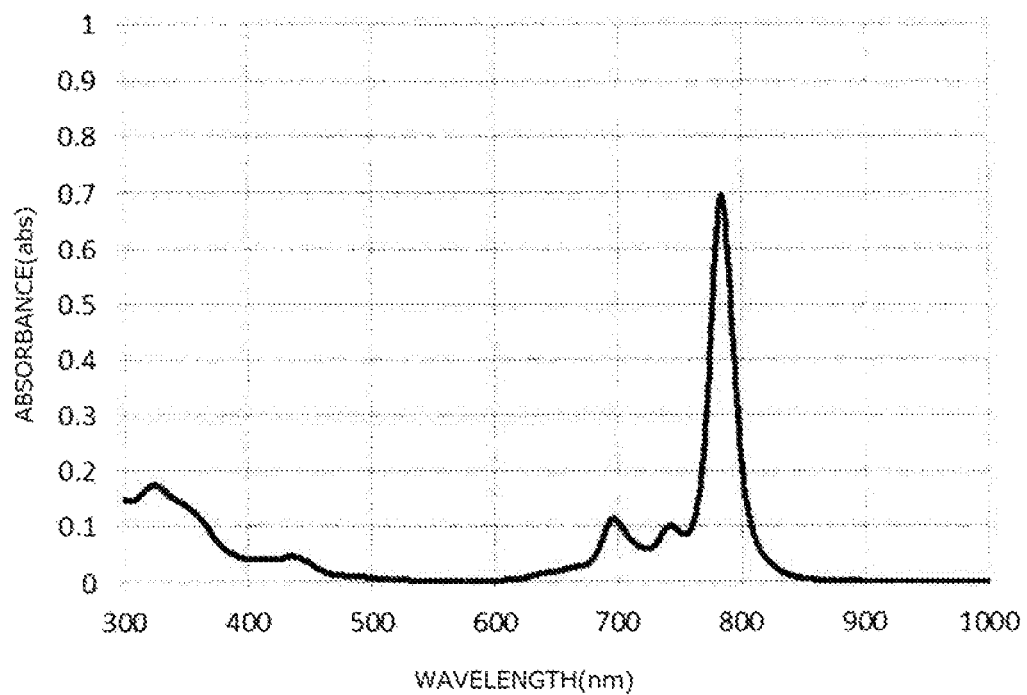
FIG. 9 is an absorption spectrum of a compound (1)-52 produced in Example 16.

A toluene solution of the compound obtained in this way had maximum absorption at 784 nm, and the gram absorption coefficient thereof was $1.38\times10^5$ mL/g·cm. The absorption spectrum chart thereof is illustrated in FIG. 9.

[Example 17] Producing of Naphthalocyanine Compound (Specific Example (1)-65)

The compound obtained in Example 6 (3.0 g), 3.24 g of N-(3-ethoxypropyl)-4-hydroxybenzene sulfonamide, and 1.72 g of potassium carbonate were added to 45 mL of DMI, and the obtained solution was heated to 185° C. and allowed to react for 5 hours. The solution was cooled to room temperature, and then 22 g of water added dropwise thereto and stirred for 1 hour. The obtained solids were filtered, rinsed with water, and then further rinsed with methanol, thereby obtaining 4.1 g of green solids. The green solids were purified by column chromatography (silica gel and toluene/ethyl acetate=100/30, v/v), concentrated, and then dispersed in 20 mL of methanol, thereby obtaining 0.73 g of green solids.

From the following analysis results, it was confirmed that the obtained compound is the intended compound.

MALDI TOF-MS: m/z 2878 (Mt)

Values of elementary analysis: actual measurement values (C: 58.57%, H: 4.48%, N: 5.62%); theoretical values (C: 58.42%, H: 4.34%, N: 5.84%)

Figure 10:
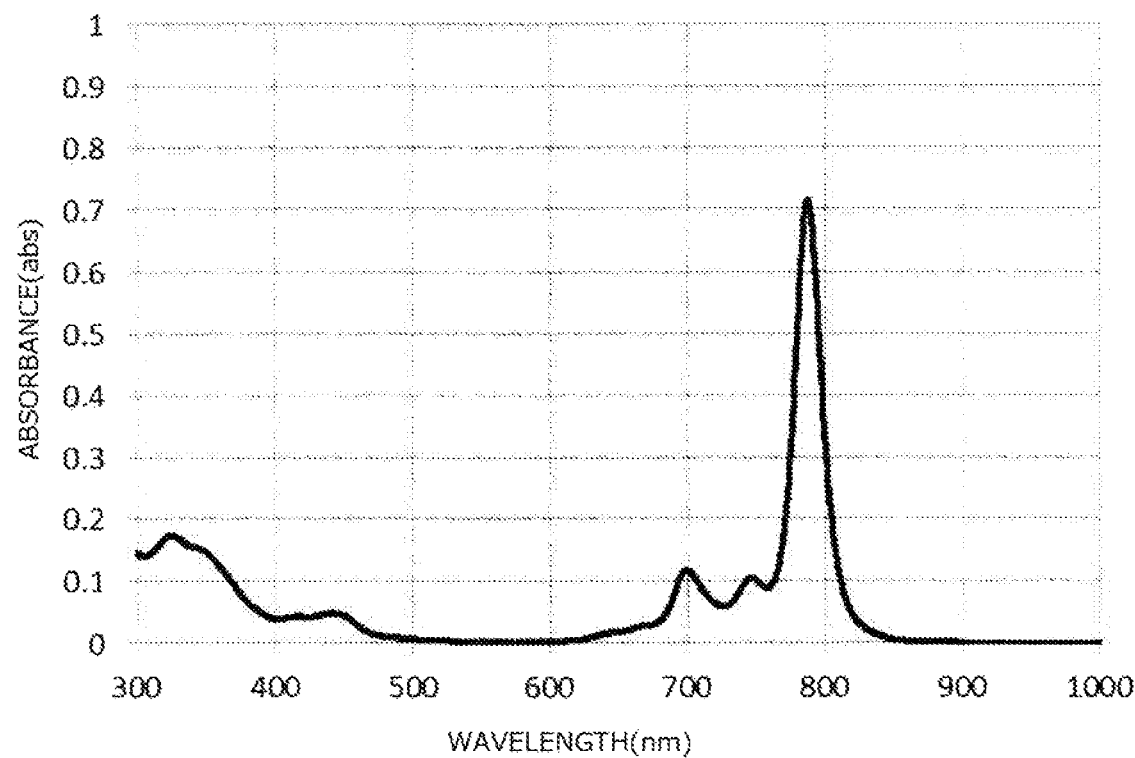
FIG. 10 is an absorption spectrum of a compound (1)-65 produced in Example 17.

A toluene solution of the compound obtained in this way had maximum absorption at 788 nm, and the gram absorption coefficient thereof was $1.29\times10^5$ mL/g cm. The absorption spectrum chart thereof is illustrated in FIG. 10.

[Comparative Example 1] Synthesis of Comparative Example Compound (a)

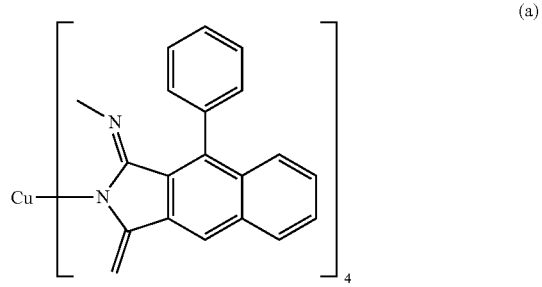

(a)

1-Phenylnaphthalene-2,3-dicarbonitrile (2.54 g), 0.40 g of copper (I) chloride, and 3.81 g of DBU were added to 10.5 g of n-dodecanol, and the obtained solution was heated to 200° C. and allowed to react for 2 hours. The solution was cooled to room temperature, 20 mL of methanol was added thereto, and the precipitate was filtered, rinsed, and dried. The precipitate was purified by column chromatography (silica gel and toluene), thereby obtaining 0.46 g of green powder. From the following analysis results, it was confirmed that the obtained compound is the intended compound.

LC-MS: m/z 1080 ([M+H]$^+$)

Values of elementary analysis: actual measurement values (C: 80.35%, H: 3.87%, N: 10.15%); theoretical values (C: 80.02%, H: 3.73%, N: 10.37%)

Figure 11:
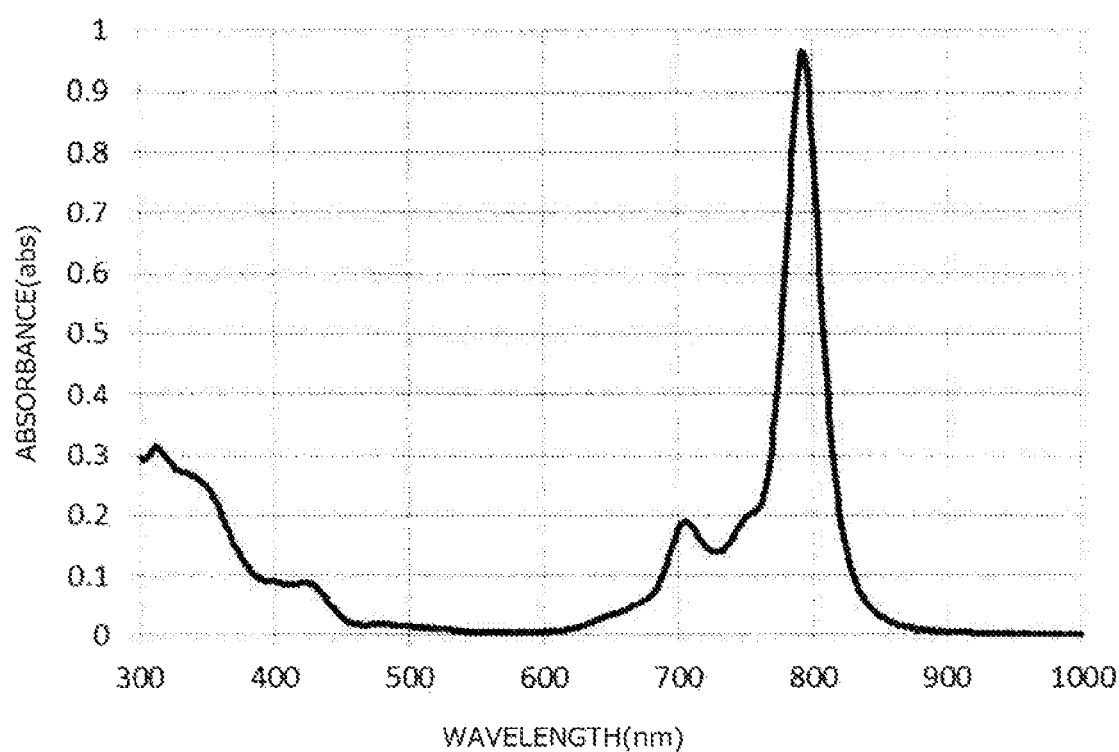
FIG. 11 is an absorption spectrum of a compound (a) produced in Comparative Example 1.

A toluene solution of the compound obtained in this way had maximum absorption at 793 nm, and the gram absorption coefficient thereof was $1.90 \times 10^5$ g/mL·cm. The absorption spectrum chart thereof is illustrated in FIG. 11.

[Comparative Example 2] Synthesis of Comparative Example Compound (b)

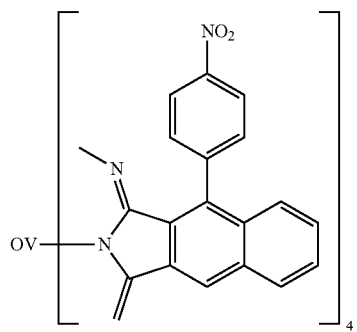

A comparative example compound (b) was produced according to Example 1 in Japanese Unexamined Patent Publication No. 2009-29955.

[Solubility]

For the naphthalocyanine compounds of the present invention and the comparative example compounds produced in the above examples, the solubility in an organic solvent was measured by the following measurement method. The results are shown in Table 4.

(Method of Measuring Solubility)

Toluene or cyclopentanone was added to about 0.1 g of each of the naphthalocyanine compounds such that the total weight thereof became 10 g, the obtained solution was irradiated with ultrasonic waves for about 30 minutes and then stirred for 2 hours at room temperature, thereby preparing a dispersion of about 1 wt %. The dispersion liquid was filtered through a membrane filter (0.2 μm), the substance obtained by filtration was dried for 1 hour in a drier at 60° C., and then the weight of the substance obtained by filtration was measured.

The solubility of the naphthalocyanine compound in a solvent is expressed by the following equation.

Solubility (wt %)=(W0−W1)/W0

W0 represents the correct weight of the naphthalocyanine compound not yet being treated, and W1 represents the weight of the substance obtained by filtration (dissolved naphthalocyanine compound residue) having been dried. In a case where a substance obtained by filtration did not remain on the filter, the solubility was regarded as being equal to or higher than 10 wt %.

In toluene and cyclopentanone, the compounds of examples exhibit higher solubility compared to the compounds of comparative examples.

TABLE 4

| Example No. | Compound | Solubility in toluene (wt %) | Solubility in cyclopentanone (wt %) |
|---|---|---|---|
| Example 4 | Specific Example (1)-9 | Equal to or higher than 10 | 5 |
| Example 7 | Specific Example (1)-11 | 0.3 | 2 |
| Example 9 | Specific Example (1)-12 | 7 | 5 |
| Example 10 | Specific Example (1)-28 | 7 | 2 |
| Example 11 | Specific Example (1)-42 | Equal to or higher than 10 | Equal to or higher than 10 |
| Example 12 | Specific Example (1)-50 | Equal to or higher than 10 | Equal to or higher than 10 |
| Example 16 | Specific Example (1)-52 | Equal to or higher than 10 | Equal to or higher than 10 |
| Example 17 | Specific Example (1)-65 | 5 | 5 |
| Comparative Example 1 | Comparative example compound (a) | Less than 0.1 | Less than 0.1 |
| Comparative Example 2 | Comparative example compound (b) | Less than 0.1 | Less than 0.1 |

[Visible Light Transmittance]

The visible light transmittance of the naphthalocyanine compound of the present invention and the comparative example compounds was measured by the following measurement method. The results are shown in Table 5 and Table 6.

(Method of Measuring Visible Light Transmittance)

Each of the naphthalocyanine compounds (1,000 mg) and approximately 90 mL of toluene were put into a 100 mL volumetric flask, and the solution in the flask was irradiated with ultrasonic waves for 30 minutes and left to stand for 2 hours at room temperature. Then, toluene was added thereto such that the meniscus of the solution matched up with the calibration mark on the volumetric flask, thereby preparing a 10 mg/L naphthalocyanine solution. The prepared solution was put into a 1 cm×1 cm cell made of PYREX (registered trademark), and the absorption spectrum thereof was measured using a spectrophotometer (manufactured by Hitachi, Ltd.: Spectrophotometer U-3500).

The absorption spectrum measured as above was converted such that the absorbance became 1.0, that is, the transmittance became 10% at the maximum absorption wavelength in a near-infrared range, thereby obtaining a transmission spectrum. Table 5 shows the transmittance of the compound, which contains copper as a central metal, at 430 nm and 610 nm in the transmission spectrum. Table 6 shows the transmittance of the compound, which contains vanadium as a central metal, at 430 nm and 610 nm in the transmission spectrum.

At 610 nm, the transmittance of the compound of the present invention was approximately the same as the transmittance of the comparative example compound (a) and the comparative example compound (b). However, at 430 nm, the transmittance of the compound of the present invention was greatly improved.

TABLE 5

Naphthalocyanine compound containing copper as central metal

| | | Transmittance (%) | |
|---|---|---|---|
| Example No. | compound | 430 nm | 610 nm |
| Example 7 | Specific Example (1)-11 | 86.8 | 99.2 |
| Example 10 | Specific Example (1)-28 | 86.8 | 98.9 |
| Example 11 | Specific Example (1)-42 | 86.6 | 98.8 |
| Example 12 | Specific Example (1)-50 | 87.2 | 99.2 |
| Example 16 | Specific Example (1)-52 | 86.4 | 98.7 |
| Example 17 | Specific Example (1)-65 | 86.8 | 98.9 |
| Comparative Example 1 | Comparative example compound (a) | 82.1 | 98.2 |

TABLE 6

Naphthalocyanine compound having vanadium as central metal

| | | Transmittance (%) | |
|---|---|---|---|
| Example No. | Compound | 430 nm | 610 nm |
| Example 4 | Specific Example (1)-9 | 90.6 | 99.7 |
| Example 9 | Specific Example (1)-12 | 90.8 | 99.4 |
| Comparative Example 2 | Comparative example compound (b) | 85.1 | 98.1 |

[Light Resistance/Heat Resistance]

The light resistance/heat resistance of the naphthalocyanine compound of the present invention and the comparative example compounds was measured by the following measurement method. The results are shown in Table 7.

(Method of Testing and Measuring Light Resistance/Heat Resistance)

The naphthalocyanine compound of the present invention or each of the comparative example compounds (0.1 g) produced in the above examples and 5.0 g of a methacryl resin DELPET (registered trademark) manufactured by Asahi Kasei Chemicals Corporation. were added to, mixed with, and dissolved in 95.0 g of toluene, thereby preparing a colorant resin solution. By using a spin coater (manufactured by Kyoei Semiconductor Co. Ltd.: SPINNER IH-III-A), a glass substrate was coated with the colorant resin solution such that the colorant concentration became 20 wt % and the dry film thickness became 2 μm, and the applied solution was dried for 3 minutes at 100° C.

The absorption spectrum of the coated glass plate obtained as above was measured using a spectrophotometer (manufactured by Hitachi, Ltd.: Spectrophotometer U-3500) and adopted as a spectrum before test. Then, the glass plate with a coating film used for measuring the spectrum before test was irradiated with light for 200 hours at 550 W/h by using a xenon light resistance tester (manufactured by Toyo Seiki Seisaku-sho, Ltd.: SUNTEST XLS+). The absorption spectrum of the glass plate with a coating film irradiated with light was measured using a spectrophotometer and adopted as a spectrum after light resistance test.

For a heat resistance test, the glass plate with a coating film used for measuring the spectrum before test was treated with heat for 200 hours at a temperature of 100° C. in a thermostat (manufactured by Yamato Scientific co., ltd.: IG400). By using a spectrophotometer, the absorption spectrum of the heat-treated glass plate with a coating film was measured and adopted as a spectrum after heat resistance test. In each of the spectra measured as above before and after the heat resistance-light resistance test, the values of absorbance within a range of 400 to 900 nm were integrated, and a difference between the absorbance before the light resistance test or heat resistance test and the absorbance after the light resistance test or heat resistance test was calculated.

The difference ΔE between the absorbance before the light resistance test or heat resistance test and the absorbance after the light resistance test or heat resistance test is expressed by the following equation.

$$\Delta E\ (\%) = \{\Sigma(400\ \text{to}\ 900\ \text{nm in}\ E1) - \Sigma(400\ \text{to}\ 900\ \text{nm in}\ E2)\}/\Sigma(400\ \text{to}\ 900\ \text{nm in}\ E1) \times 100$$

E1 represents the spectrum before test, E2 represents the spectrum after test, and Σ represents integration of the values of absorbance.

The larger the value of ΔE, the greater the spectrum change before and after the light resistance test or heat resistance test.

As shown in Table 7, all of the compounds of examples exhibited better characteristics on light resistance and heat resistance compared to comparative examples.

TABLE 7

| | | ΔE (%) | |
|---|---|---|---|
| Example No. | Compound | Light resistance | Heat resistance |
| Example 4 | Specific Example (1)-9 | 8 | 10 |
| Example 7 | Specific Example (1)-11 | 7 | 8 |
| Example 9 | Specific Example (1)-12 | 7 | 8 |
| Example 10 | Specific Example (1)-28 | 6 | 7 |
| Example 11 | Specific Example (1)-42 | 6 | 8 |
| Example 12 | Specific Example (1)-50 | 5 | 7 |
| Example 16 | Specific Example (1)-52 | 5 | 7 |
| Example 17 | Specific Example (1)-65 | 7 | 8 |
| Comparative Example 1 | Comparative example compound (a) | 25 | 28 |
| Comparative Example 2 | Comparative example compound (b) | 35 | 37 |

[Example 18] Producing of Heat Ray Shielding Film

The naphthalocyanine compound (Specific Example (1)-9) produced in Example 4 (5 g), 50 g of an acryl resin LP-45M (trade name, produced by Soken Chemical & Engineering Co., Ltd.), 20 g of methylethylketone, and 20 g of toluene were mixed and stirred together, thereby producing a resin composition.

As a transparent substrate, a polyethylene terephthalate film (PET film) having a thickness of 100 μm was bar-coated with the resin composition such that the thickness thereof became 2.5 μm, and then the applied resin composition was dried for 3 minutes at 100° C.

Furthermore, the other surface of the PET film (surface not being coated with the resin composition) was bar-coated with a transparent acryl copolymer-based pressure sensitive adhesive such that the thickness thereof became 20 μm, and the applied pressure sensitive adhesive was dried and cured for 3 minutes at 100° C. Thereafter, a release film was bonded to the surface of the pressure sensitive adhesive, thereby producing a heat ray shielding film.

[Example 19] Producing of Heat Ray Shielding Film

A heat ray shielding film was produced by performing the same operation as in Example 18, except that, the compound of Specific Example (1)-11 was used as a naphthalocyanine compound instead of the compound of Specific Example (1)-9 in Example 18.

[Example 20] Producing of Heat Ray Shielding Film

A heat ray shielding film was produced by performing the same operation as in Example 18, except that, the compound of Specific Example (1)-12 was used as a naphthalocyanine compound instead of the compound of Specific Example (1)-9 in Example 18.

[Example 21] Producing of Heat Ray Shielding Film

A heat ray shielding film was produced by performing the same operation as in Example 18, except that, the compound of Specific Example (1)-28 was used as a naphthalocyanine compound instead of the compound of Specific Example (1)-9 in Example 18.

[Example 22] Producing of Heat Ray Shielding Film

A heat ray shielding film was produced by performing the same operation as in Example 18, except that, the compound of Specific Example (1)-42 was used as a naphthalocyanine compound instead of the compound of Specific Example (1)-9 in Example 18.

[Example 23] Producing of Heat Ray Shielding Film

A heat ray shielding film was produced by performing the same operation as in Example 18, except that, the compound of Specific Example (1)-50 was used as a naphthalocyanine compound instead of the compound of Specific Example (1)-9 in Example 18.

[Example 24] Producing of Heat Ray Shielding Film

A heat ray shielding film was produced by performing the same operation as in Example 18, except that, the compound of Specific Example (1)-52 was used as a naphthalocyanine compound instead of the compound of Specific Example (1)-9 in Example 18.

[Example 25] Producing of Heat Ray Shielding Film

A heat ray shielding film was produced by performing the same operation as in Example 18, except that, the compound of Specific Example (1)-65 was used as a naphthalocyanine compound instead of the compound of Specific Example (1)-9 in Example 18.

[Comparative Example 3] Producing of Heat Ray Shielding Film

A heat ray shielding film was produced by performing the same operation as in Example 18, except that, the comparative example compound (a) was used as a naphthalocyanine compound instead of the compound of Specific Example (1)-9 in Example 18.

[Comparative Example 4] Producing of Heat Ray Shielding Film

A heat ray shielding film was produced by performing the same operation as in Example 18, except that, the comparative example compound (b) was used as a naphthalocyanine compound instead of the compound of Specific Example (1)-9 in Example 18.

The heat ray shielding films of Examples 18 to 25 and Comparative Examples 3 and 4 described above were evaluated in terms of the following items. The results are shown in the following Table 8. In the evaluation test, the release film was peeled from the produced heat ray shielding film, then the heat ray shielding film was compressed on a 5 cm×5 cm×3 mm (thickness) glass plate, and a test piece created in this way was used.

[Tts]

By using U-3500 type recording spectrophotometer manufactured by Hitachi, Ltd. as a measurement instrument, Tts of the laminated glass sample was measured based on JIS R3106 "Testing method on transmittance, reflectance and emittance of flat glasses and evaluation of solar heat gain coefficient".

Tts (Total solar energy transmitted through a glazing) represents a total solar transmittance. The smaller the Tts, the higher the heat shielding ability.

[Light Resistance/Heat Resistance]

For a light resistance test, an absorption spectrum of a test piece was measured using a spectrophotometer (manufactured by Hitachi, Ltd.: Spectrophotometer U-3500) and adopted as a spectrum before light resistance test. Then, the test piece used for measuring the spectrum before test was irradiated with light for 200 hours at 550 W/h by using a xenon light resistance tester (manufactured by Toyo Seiki Seisaku-sho, Ltd.: SUNTEST XLS+). The absorption spectrum of the test piece irradiated with light was measured using a spectrophotometer and adopted as a spectrum after light resistance test.

For a heat resistance test, the test piece used for measuring the spectrum before test as described above was treated with heat for 200 hours at a temperature of 100° C. in a thermostat (manufactured by Yamato Scientific co., ltd.: IG400). By using a spectrophotometer, the absorption spectrum of the heat-treated test piece was measured and adopted as a spectrum after heat resistance test.

In each of the spectra measured as above before and after the light resistance test or heat resistance test, the values of absorbance within a range of 400 to 900 nm were integrated, and a difference between the absorbance before the light resistance test or heat resistance test and the absorbance after the light resistance test or heat resistance test was calculated.

The difference ΔE between the absorbance before the light resistance test or heat resistance test and the absorbance after the light resistance test or heat resistance test is expressed by the following equation.

$$\Delta E\ (\%) = \{\Sigma(400\ to\ 900\ nm\ in\ E1) - \Sigma(400\ to\ 900\ nm\ in\ E2)\}/\Sigma(400\ to\ 900\ nm\ in\ E1) \times 100$$

E1 represents the spectrum before test, E2 represents the spectrum after test, and Σ represents integration of the values of absorbance.

The larger the value of ΔE, the greater the spectrum change before and after the light resistance test or heat resistance test.

As shown in Table 8, all of the heat ray shielding films of examples exhibited better characteristics such as a heat shielding ability, light resistance, and heat resistance compared to comparative examples.

TABLE 8

| | | | ΔE (%) | |
|---|---|---|---|---|
| Example No. | Compound | Tts | Light resistance | Heat resistance |
| Example 18 | Specific Example (1)-9 | 85.5 | 7 | 7 |
| Example 19 | Specific Example (1)-11 | 86.3 | 6 | 7 |
| Example 20 | Specific Example (1)-12 | 85.5 | 7 | 8 |
| Example 21 | Specific Example (1)-28 | 86.7 | 6 | 7 |
| Example 22 | Specific Example (1)-42 | 86.2 | 6 | 8 |
| Example 23 | Specific Example (1)-50 | 85.9 | 5 | 6 |
| Example 24 | Specific Example (1)-52 | 86.0 | 5 | 7 |
| Example 25 | Specific Example (1)-65 | 86.5 | 7 | 7 |
| Comparative Example 3 | Comparative example compound (a) | 87.8 | 27 | 28 |
| Comparative Example 4 | Comparative example compound (b) | 89.5 | 38 | 35 |

[Example 26] Preparation of Interlayer for Laminated Glass and Laminated Glass

<Preparation of Interlayer for Laminated Glass>

The naphthalocyanine compound (Specific Example (1)-9) produced in Example 4 (0.013 g) was dissolved in 40 g of triethylene glycol-di-2-ethylhexanoate as an organic ester plasticizer. The obtained solution was added to 100 g of a polyvinyl butyral resin (trade name: BH-3, manufactured by SEKISUI CHEMICAL CO., LTD.), thoroughly melted and kneaded using a mixing roll, and extruded using an extruder, thereby obtaining an interlayer having a thickness of 0.76 mm.

<Preparation of Laminated Glass>

The interlayer was cut in size of 100 mm×100 mm, interposed between heat ray absorbing glass plates (100 mm (length)×100 mm (width)×2.0 mm (thickness)) prepared based on JIS R3208, put into a rubber bag, and deaerated for 20 minutes at a degree of vacuum of 2.6 kPa. Then, the deaerated laminate was moved into an oven as it was and pressed in vacuum for 30 minutes at 90° C. Thereafter, the laminate was compressed for 20 minutes in an autoclave under the condition of a temperature of 130° C. and a pressure of 1.3 MPa, thereby obtaining a laminated glass sample.

[Example 27] Preparation of Interlayer for Laminated Glass and Laminated Glass

An interlayer for laminated glass and laminated glass were prepared by performing the same operation as in Example 26, except that in Example 26, the compound of Specific Example (1)-11 was used as a naphthalocyanine compound instead of the compound of Specific Example (1)-9.

[Example 28] Preparation of Interlayer for Laminated Glass and Laminated Glass

An interlayer for laminated glass and laminated glass were prepared by performing the same operation as in Example 26, except that in Example 26, the compound of Specific Example (1)-12 was used as a naphthalocyanine compound instead of the compound of Specific Example (1)-9.

[Example 29] Preparation of Interlayer for Laminated Glass and Laminated Glass

An interlayer for laminated glass and laminated glass were prepared by performing the same operation as in Example 26, except that in Example 26, the compound of Specific Example (1)-28 was used as a naphthalocyanine compound instead of the compound of Specific Example (1)-9.

[Example 30] Preparation of Interlayer for Laminated Glass and Laminated Glass

An interlayer for laminated glass and laminated glass were prepared by performing the same operation as in Example 26, except that in Example 26, the compound of Specific Example (1)-42 was used as a naphthalocyanine compound instead of the compound of Specific Example (1)-9.

[Example 31] Preparation of Interlayer for Laminated Glass and Laminated Glass

An interlayer for laminated glass and laminated glass were prepared by performing the same operation as in Example 26, except that in Example 26, the compound of Specific Example (1)-50 was used as a naphthalocyanine compound instead of the compound of Specific Example (1)-9.

[Example 32] Preparation of Interlayer for Laminated Glass and Laminated Glass

An interlayer for laminated glass and laminated glass were prepared by performing the same operation as in Example 26, except that in Example 26, the compound of Specific Example (1)-52 was used as a naphthalocyanine compound instead of the compound of Specific Example (1)-9.

[Example 33] Preparation of Interlayer for Laminated Glass and Laminated Glass

An interlayer for laminated glass and laminated glass were prepared by performing the same operation as in Example 26, except that in Example 26, the compound of Specific Example (1)-65 was used as a naphthalocyanine compound instead of the compound of Specific Example (1)-9.

[Comparative Example 5] Preparation of Interlayer for Laminated Glass and Laminated Glass An interlayer for laminated glass and laminated glass were prepared by performing the same operation as in Example 26, except that in Example 26, the comparative example compound (a) was used as a naphthalocyanine compound instead of the compound of Specific Example (1)-9.

[Comparative Example 6] Preparation of Interlayer for Laminated Glass and Laminated Glass An interlayer for laminated glass and laminated glass were prepared by performing the same operation as in Example 26, except that in Example 26, the comparative example compound (b) was used as a naphthalocyanine compound instead of the compound of Specific Example (1)-9.

The laminated glass samples of Examples 26 to 33 and Comparative Examples 5 and 6 were evaluated in terms of the following items. The results are shown in the following Table 9.

[Tts]

By using U-3500 type recording spectrophotometer manufactured by Hitachi, Ltd. as a measurement instrument, Tts of the laminated glass samples was measured based on JIS R3106 "Testing method on transmittance, reflectance and emittance of flat glasses and evaluation of total solar energy transmittance of glazing".

[Visible Light Transmittance]

By using U-3500 type recording spectrophotometer manufactured by Hitachi, Ltd. as a measurement instrument, the visible light transmittance of the laminated glass samples at a wavelength of 380 to 780 nm was measured based on JIS R 3212 "Test methods of safety glazing materials for road vehicles".

[Light Resistance/Heat Resistance]

For a light resistance test, the absorption spectrum of the laminated glass was measured using a spectrophotometer (manufactured by Hitachi, Ltd.: Spectrophotometer U-3500) and adopted as a spectrum before light resistance test. Then, the laminated glass used for measuring the spectrum before test was irradiated with light for 200 hours at 550 W/h by using a xenon light resistance tester (manufactured by Toyo Seiki Seisaku-sho, Ltd.: SUNTEST XLS+). The absorption spectrum of the laminated glass irradiated with light was measured using a spectrophotometer and adopted as a spectrum after light resistance test.

For a heat resistance test, the laminated glass used for measuring the spectrum before test as described above was treated with heat for 200 hours at a temperature of 100° C. in a thermostat (manufactured by Yamato Scientific co., ltd.: IG400). By using a spectrophotometer, the absorption spectrum of the heat-treated laminated glass was measured and adopted as a spectrum after heat resistance test.

In each of the spectra measured as above before and after the light resistance test or heat resistance test, the absorbances within a range of 400 to 900 nm were integrated, and a difference between the integrated absorbance before the light resistance test or heat resistance test and the integrated absorbance after the light resistance test or heat resistance test was calculated.

The difference $\Delta E$ between the absorbance before the light resistance test or heat resistance test and the absorbance after the light resistance test or heat resistance test is expressed by the following equation.

$$\Delta E\ (\%) = \{\Sigma(400 \text{ to } 900 \text{ nm in } E1) - \Sigma(400 \text{ to } 900 \text{ nm in } E2)\}/\Sigma(400 \text{ to } 900 \text{ nm in } E1) \times 100$$

E1 represents the spectrum before test, E2 represents the spectrum after test, and $\Sigma$ represents integration of absorbances. The larger the value of $\Delta E$ shows the greater the spectrum change before and after the light resistance test or heat resistance test. As shown in Table 9, all of the interlayers for laminated glass of examples exhibited better characteristics such as a heat shielding ability, a visible light transmittance, light resistance, and heat resistance compared to comparative examples.

TABLE 9

| Example No. | Compound | Tts | Visible light transmittance | ΔE (%) Light resistance | ΔE (%) Heat resistance |
|---|---|---|---|---|---|
| Example 26 | Specific Example (1)-9 | 51.5 | 78.1 | 6 | 7 |
| Example 27 | Specific Example (1)-11 | 52.2 | 77.3 | 6 | 5 |
| Example 28 | Specific Example (1)-12 | 51.9 | 78.0 | 6 | 6 |
| Example 29 | Specific Example (1)-28 | 52.3 | 77.5 | 7 | 8 |
| Example 30 | Specific Example (1)-42 | 52.1 | 77.9 | 7 | 8 |
| Example 31 | Specific Example (1)-50 | 52.4 | 77.3 | 6 | 5 |
| Example 32 | Specific Example (1)-52 | 52.2 | 77.4 | 6 | 5 |
| Example 33 | Specific Example (1)-65 | 52.3 | 77.6 | 7 | 8 |
| Comparative Example 5 | Comparative example compound (a) | 54.2 | 76.8 | 28 | 27 |
| Comparative Example 6 | Comparative example compound (b) | 53.9 | 75.1 | 36 | 34 |

The naphthalocyanine compound of the present invention has strong absorption in a near-infrared range and extremely weak absorption in a visible range, exhibits excellent solubility in an organic solvent or a resin, and has high durability such as light resistance and heat resistance.

Accordingly, the naphthalocyanine compound of the present invention is extremely useful as a near-infrared absorbing colorant for uses such as a near-infrared cut-off filter, a transparent ink used for security, a heat ray shielding film used in windows of automobiles or buildings, an interlayer for laminated glass, an infrared thermosensitive recording material, and laser welding of plastics.

The invention claimed is:

1. A naphthalocyanine compound represented by General Formula (1),

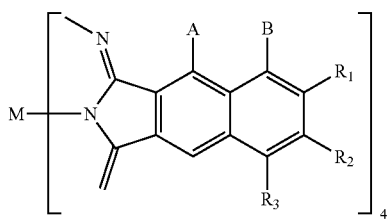
(1)

wherein, in Formula (1), M represents two hydrogen atoms, a divalent metal atom, or a divalent derivative of a trivalent or tetravalent metal, $R_1$ to $R_3$ each independently represent a hydrogen atom, a halogen atom, or a linear, branched, or cyclic alkyl group, A represents Formula (2), and B represents Formula (3),

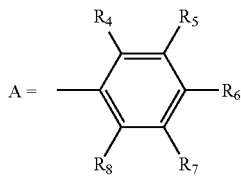
(2)

wherein, in Formula (2), $R_4$ to $R_8$ each independently represent a hydrogen atom, a halogen atom, a substituted or unsubstituted linear, branched, or cyclic alkyl group, a substituted or unsubstituted linear, branched, or cyclic alkoxy group, a substituted or unsubstituted linear, branched, or cyclic alkylthio group, an aryloxy group which optionally have a substituent, an arylthio group which optionally have a substituent, and $R_4$ to $R_8$ do not simultaneously represent a hydrogen atom, and

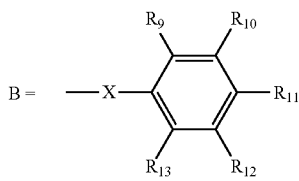
(3)

wherein, in Formula (3), X represents an oxygen atom, a sulfur atom, or a substituted or unsubstituted imino group, $R_9$ to $R_{13}$ each independently represent a hydrogen atom, a halogen atom, a substituted or unsubstituted alkyl group, a substituted or unsubstituted alkoxy group, an ester group ($COOX_1$ wherein $X_1$ represents a hydrogen atom, a substituted or unsubstituted alkyl group, or a substituted or unsubstituted, aryl group), an amide group ($CONX_2X_3$ wherein $X_2$ and $X_3$ each independently represent a hydrogen atom, a substituted or unsubstituted alkyl group, or a substituted or unsubstituted aryl group), or a sulfonamide group ($SO_2NX_4X_5$ wherein $X_4$ and $X_5$ each independently represent a hydrogen atom, a substituted or unsubstituted alkyl group, or a substituted or unsubstituted aryl group), and $R_9$ to $R_{13}$ do not simultaneously represent a hydrogen atom.

2. The naphthalocyanine compound according to claim 1 that is at least one kind selected from compounds represented by General Formulae (1)-a to (1)-d,

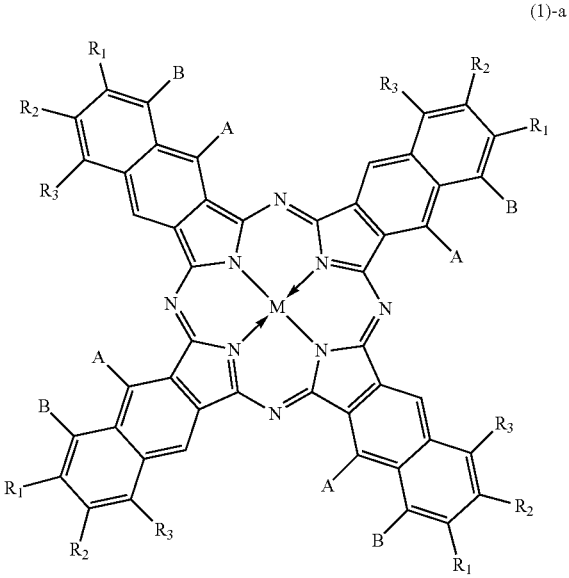
(1)-a

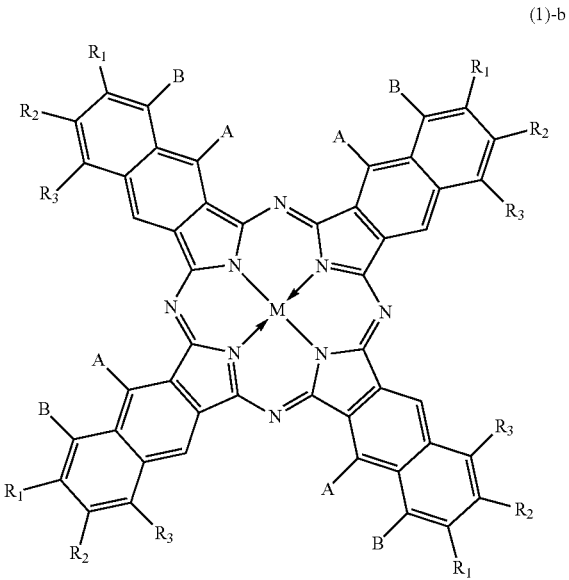
(1)-b

-continued

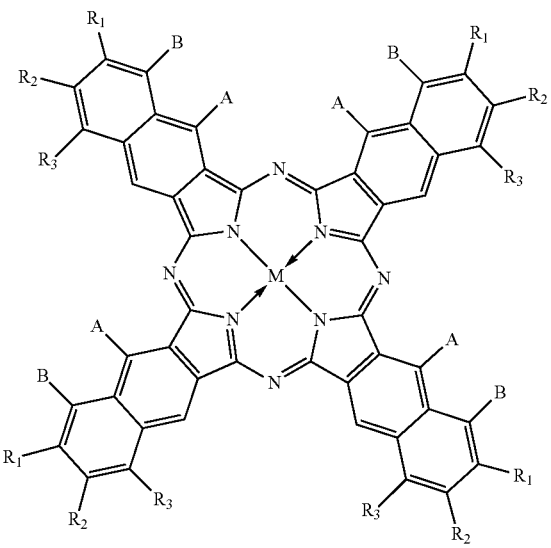
(1)-c

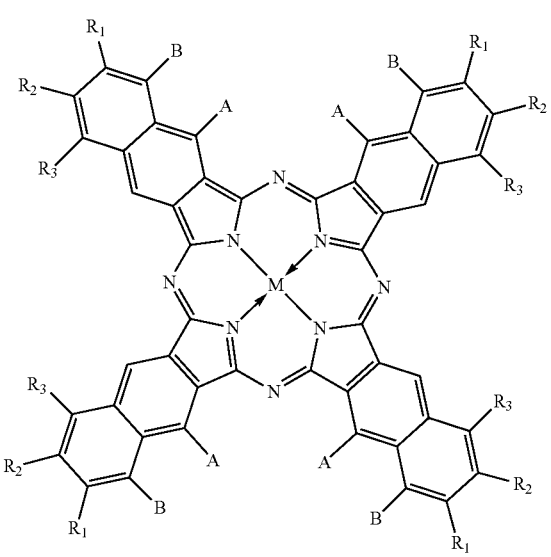
(1)-d wherein, in Formulae (1)-a to (1)-d, M, $R_1$ to $R_3$, A, and B have the same definition as M, $R_1$ to $R_3$, A, and B in General Formula (1).

3. The naphthalocyanine compound according to claim 1 that is represented by General Formula (1)-a,

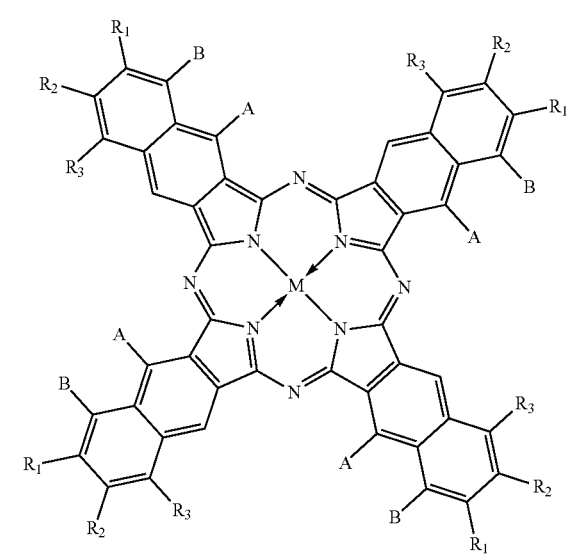
(1)-a wherein, in Formula (1)-a, M, $R_1$ to $R_3$, A, and B have the same definition as M, $R_1$ to $R_3$, A, and B in General Formula (1).

4. The naphthalocyanine compound according to claim 1, wherein M represents two hydrogen atoms, Pd, Cu, Zn, Pt, Ni, TiO, Co, Fe, Mn, Sn, Al—Cl, VO, or In—Cl.

5. The naphthalocyanine compound according to claim 2, wherein M represents two hydrogen atoms, Pd, Cu, Zn, Pt, Ni, TiO, Co, Fe, Mn, Sn, Al—Cl, VO, or In—Cl.

6. The naphthalocyanine compound according to claim 3, wherein M represents two hydrogen atoms, Pd, Cu, Zn, Pt, Ni, TiO, Co, Fe, Mn, Sn, Al—Cl, VO, or In—Cl.

7. A process for producing the naphthalocyanine compound according to claim 1, comprising:
reacting at least one kind of compounds selected from a naphthalene-2,3-dicarbonitrile compound represented by General Formula (4) and a 1,3-diiminobenzisoindoline compound represented by General Formula (5) with a metal or a metal derivative,

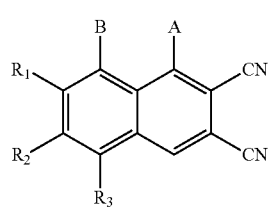
(4)

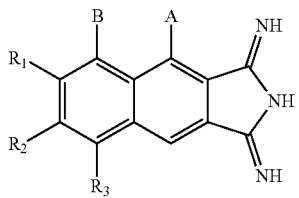
(5)

wherein, in Formulae (4) and (5), $R_1$ to $R_3$, A, and B have the same definition as $R_1$ to $R_3$, A, and B in General Formula (1).

8. A naphthalene-2,3-dicarbonitrile compound represented by General Formula (4),

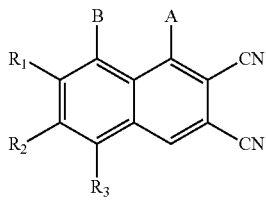
(4)

wherein, in Formula (4), $R_1$ to $R_3$, A, and B have the same definition as $R_1$ to $R_3$, A, and B in General Formula (1).

9. A 1,3-diiminobenzisoindoline compound represented by General Formula (5),

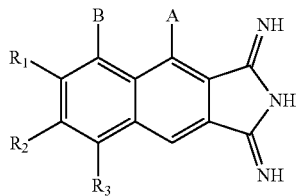
(5)

wherein, in Formula (5), $R_1$ to $R_3$, A, and B have the same definition as $R_1$ to $R_3$, A, and B in General Formula (1).

10. A near-infrared absorbing material comprising:
the naphthalocyanine compound according to claim 1.

11. A heat ray shielding material comprising:
the naphthalocyanine compound according to claim 1.

12. The heat ray shielding material, according to claim 11 that is a heat ray shielding film.

13. The heat ray shielding material according to claim 11 that is an interlayer for laminated glass.

* * * * *